US011261426B2

(12) United States Patent
Dezawa et al.

(10) Patent No.: US 11,261,426 B2
(45) Date of Patent: *Mar. 1, 2022

(54) PLURIPOTENT STEM CELL THAT CAN BE ISOLATED FROM BODY TISSUE

(71) Applicants: Mari Dezawa, Miyagi (JP); Yoshinori Fujiyoshi, Kyoto (JP); Youichi Nabeshima, Kyoto (JP)

(72) Inventors: Mari Dezawa, Miyagi (JP); Yoshinori Fujiyoshi, Kyoto (JP); Youichi Nabeshima, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/189,215

(22) Filed: Jun. 22, 2016

(65) Prior Publication Data

US 2016/0369232 A1  Dec. 22, 2016

Related U.S. Application Data

(63) Continuation of application No. 13/435,703, filed on Mar. 30, 2012, now Pat. No. 9,399,758, which is a continuation-in-part of application No. 12/836,264, filed on Jul. 14, 2010, now Pat. No. 9,550,975.

(60) Provisional application No. 61/213,788, filed on Jul. 15, 2009, provisional application No. 61/290,159, filed on Dec. 24, 2009.

(30) Foreign Application Priority Data

Mar. 30, 2011  (JP) .............................. JP2011-076635
Mar. 30, 2011  (JP) .............................. JP2011-076643

(51) Int. Cl.
| | | |
|---|---|---|
| *A61K 35/28* | (2015.01) | |
| *C12N 5/074* | (2010.01) | |
| *C12N 5/073* | (2010.01) | |
| *C12N 5/0775* | (2010.01) | |
| *A61K 35/51* | (2015.01) | |
| *A61K 35/12* | (2015.01) | |
| *A61K 35/50* | (2015.01) | |

(52) U.S. Cl.
CPC ............ *C12N 5/0607* (2013.01); *A61K 35/28* (2013.01); *C12N 5/0605* (2013.01); *C12N 5/0663* (2013.01); *C12N 5/0665* (2013.01); *C12N 5/0667* (2013.01); *A61K 35/12* (2013.01); *A61K 35/50* (2013.01); *A61K 35/51* (2013.01); *A61K 2035/124* (2013.01); *C12N 5/0662* (2013.01); *C12N 2500/02* (2013.01); *C12N 2500/84* (2013.01); *C12N 2500/90* (2013.01); *C12N 2501/06* (2013.01); *C12N 2501/734* (2013.01); *C12N 2501/998* (2013.01); *C12N 2502/025* (2013.01)

(58) Field of Classification Search
CPC .............................. C12N 5/0607; A61K 35/28
See application file for complete search history.

(56) References Cited

U.S. PATENT DOCUMENTS

| | | |
|---|---|---|
| 7,060,492 B2 | 6/2006 | Vacanti et al. |
| 9,730,965 B2 * | 8/2017 | Soo ........................ A61P 19/00 |
| 2004/0057942 A1 | 3/2004 | Vacanti et al. |
| 2006/0216821 A1 | 9/2006 | Totey et al. |
| 2009/0068742 A1 | 3/2009 | Yamanaka |
| 2009/0155225 A1 | 6/2009 | Ratajczak et al. |
| 2009/0175832 A1 | 7/2009 | Zhao et al. |
| 2011/0070647 A1 | 3/2011 | Dezawa et al. |

FOREIGN PATENT DOCUMENTS

| | | |
|---|---|---|
| EP | 2455452 A1 | 5/2012 |
| JP | 5852503 B2 | 2/2016 |
| WO | WO 01/11011 A2 | 2/2001 |
| WO | WO 01/11011 A3 | 2/2001 |
| WO | WO-2005/017117 A2 | 2/2005 |
| WO | WO-2007/047581 A2 | 4/2007 |
| WO | WO-2007/069666 A1 | 6/2007 |
| WO | WO-2008/080200 A1 | 7/2008 |

OTHER PUBLICATIONS

Fauza et al (Best Practice & Research Clinical Obstetrics and Gynaecology vol. 18, No. 6, pp. 877-891, 2004).*
D'Ippolito et al (Journal of Cell Science, 117(14): 2971-2981, 2004).*
Gafni et al (Nature, 504: 282-286, 2013).*
Zhang et al (Stem Cells and Development, 18(9): 1299-1308, 2009 (Year: 2009).*
Yi-Hua et al (Chinese Journal of Agricultural Biotechnology 5(3); 237-244, 2008). (Year: 2008).*
Sikkema-Raddatz et al (Prenat Diagn, 26: 855-860, 2006). (Year: 2006).*
Rojewski et al, (Transfus Med Hemother 2008;35:168-184) (Year: 2008).*
Colter et al, (Proc. Natl. Acad. Sci. USA 98, 7841-7845, 2001). (Year: 2001).*
Gimble et al, (Circ Res, 100:1249-1260, 2007) . (Year: 2007).*
Gang ((Blood. 2007; 109:1743-1751 (Year: 2007).*
Battula et al., "Human placenta and bone marrow derived MSC cultured in serum-free, b-FGF-containing medium, express cell surface frizzled-9 and SSEA-4 and give rise to multilineage differentiation", Differentiation, 2007, vol. 75, pp. 279-291.
Brooke et al., "Molecular Trafficking Mechanisms of Multipotent Mesenchymal Stem Cells Derived from Human Bone Marrow and placenta", Stem Cells and Development, 2008, vol. 17, pp. 929-940.
Chan et al., "Antigen-Presenting property of mesenchymal stem cells occurs during a narrow window at low levels of interferon-gamma", Blood, 2006, vol. 107, pp. 4817-4824.

(Continued)

*Primary Examiner* — Anoop K Singh
*Assistant Examiner* — Magdalene K Sgagias
(74) *Attorney, Agent, or Firm* — Oblon, McClelland, Maier & Neustadt, L.L.P.

(57) ABSTRACT

Objects of the present invention are to provide a method for directly obtaining pluripotent stem cells which do not have tumorigenic property from body tissue and the thus obtained pluripotent stem cells. The present invention relates to SSEA-3 (+) pluripotent stem cells that can be isolated from body tissue.

8 Claims, 74 Drawing Sheets

Specification includes a Sequence Listing.

(56) References Cited

OTHER PUBLICATIONS

Chen et al., "Differentiation of rat marrow mesenchymal stem cells into pancreatic islet beta-cells", World J. Gastroenterology, 2004, vol. 10, pp. 3016-3020.
Chen et al., "Engraftment potential of human placenta-derived mesenchymal stem cells after in utero transplantation in rats", Human reproduction, 2009, vol. 24, pp. 154-165.
Communication dated Jan. 11, 2013 in EP Patent Application No. 10799956.7.
Dezawa, Mari, "Skin/Bone Marrow-Derived Stem Cell, 'Muse'," Rinsho Hyoka:Clinical Evaluation, Mar. 1, 2011, 38(4):749-760, with English translation.
Draper J., et al., "Surface antigens of human embryonic stem cells: changes upon differentiation in culture", J. Anat. (2002) 200, pp. 249-258.
EP Application No. 10799956.7 Search Report dated Oct. 24, 2013.
Ferro et al., "Isolation and Characterization of Human Dental Pulp Derived Stem Cells by Using Media Containing Low Human Serum Percentage as Clinical Grade Substitutes for Bovine Serum", PLOS, 2012, vol. 7, e48945.
Gang et al., "SSEA-4 identified mesenchymal stem cells from bone marrow", Blood, Feb. 15, 2007, vol. 109, No. 4, pp. 1743-1751.
Henderson, J.K. et al., "Preimplantation Human Embryos and Embryonic Stem Cells Show Comparable Expression of Stage-Specific Enbryonic Antgens", Stem Cells 2002;20:329-337.
Huang et al., "Isolation of Mesenchymal Stem Cells from Human Placental Decidua Basalis and Resistance to Hypoxia and Serum Deprivation", Stem Cell Review and Rep., 2009, vol. 5, pp. 247-255.
International Search Report dated Jun. 12, 2012 in PCT/JP2012/059422.
International Search Report dated May 22, 2012 in PCT/JP2012/059431.
Iohara et al., "Novel Stem Cell Source for Vasculogenesis in Ischemia: Subfraction of Side Population Cells from Dental Pulp", Stem Cells, 2008. vol. 26, pp. 2408-2418.
Iohara et al., "Side Population Cells Isolated from Porcine Dental Pulp Tissue with Self-Renewal and Multipotency for Dentinogenesis, Chondrogenesis, Adipogenesis, and Neurogenesis", Stem Cells, 2006, vol. 24, pp. 2493-2503.
Jo et al., "Fetal mesenchymal stem cells derived from human umbilical cord sustain primitive characteristics during extensive expansion", Cell Tissue Res (2008) 334:423-433.
Kerkis et al., "Isolation and Characterization of a Population of Immature Dental Pulp Stem Cells Expressing OCT-4 and Other Embryonic Stem Cell Markers," Cells Tissues Organs, 2006, vol. 184, pp. 105-116.
Kubis et al., "Adult fast myosin pattern and Ca21-induced slow myosin pattern in primary skeletal muscle culture," PNAS, 1997, 94:4205-4210.
Kuroda et al., "Unique multipotent cells in adult human mesenchymal cell populations", PNAS, May 11, 2010, vol. 107, No. 19, pp. 8639-8643.
Liu et al., "Culture and exogenous gene expression of adipose tissue-derived multipotent stem cells", Chinese Journal of Experimental Surgery, Feb. 2003, vol. 20, No. 2, pp. 162-163.
Liu et al., "Dental Pulp Stem Cells," Methods in Enzymology, 2006, vol. 419, pp. 99-113, Elsevier Ltd.
Mauney et al., "Matrix-mediated retention of in vitro osteogenic differentiation potential and in vivo bone-forming capacity by human adult bone marrow-derived mesenchymal stem cells during ex vivo expansion", Journal of Biomedical Material Research Part A DOI 10.1002, 2006, pp. 464-475.
McGukin, C.P. et al., "Production of Stem Cells With Embryonic Characteristics From Human Umbilical Cord Blood", Cell Proliferation, (2005) vol. 38, No. 4, pp. 245-255.
McKenna et al., "Isolation and Characterization of Umbilical Cord Blood-Derived Multipotent Stem Cells Arising from Adherent CD45+/CD34+ Cell Subset," Blood, 2005, 106(11):310A, Abstract 1064.

Moon, J.H., et al., Successful vitrification of human amnion-derived mesenchymal stem cells, Human Reproduction, 2008, vol. 23, No. 8 pp. 1760-1770.
Moriscot et al., "Human Bone Marrow Mesenchymal Stem Cells Can Express Insulin and Key Transcription Factors of the Endocrine Pancreas Developmental Pathway upon Genetic and/or Microenvironmental Manipulation In Vitro", Stem Cells 2005; 23:594-604.
Nakashima et al., "Human dental pulp stem cells with highly angiogenic and neurogenic potential for possible use in pulp regeneration", Cytokine & Growth Factors, 2009, vol. 20, pp. 435-440.
Office Action dated Aug. 7, 2013 in U.S. Appl. No. 12/836,264.
Office Action dated Dec. 5, 2012, in U.S. Appl. No. 12/836,264.
Office Action dated Jun. 24, 2014, in CN 201280017087.2.
Office Action dated Mar. 22, 2012, in U.S. Appl. No. 12/836,264.
Office Action dated May 21, 2013 in CA Application No. 2,768,238.
Office Action dated May 22, 2013 in CN Application No. 201080041908.7.
Office Action dated Sep. 13, 2013 in Australian Application No. 2010271722.
Rezapour et al., "Telomere length and telomerase expression in human dental pulp cells," British Society for Dental Research, Sep. 1-4, 2009, Abs. 228.
Schwartz et al., "Multipotent adult progenitor cells from bone marrow differentiate into functional hepatocyte-like cells," Clinical Invest., 2002, vol. 109, No. 10, pp. 1291-1302.
Sebastien Start et al., "Ear mesenchymal stem cells: An efficient adult multipotent cell population fit for rapid and scalable expansion", Journal of Biotechnology 139 (2009) 291-299.
Sung et al., "Stemness Evaluation of Mesenchymal Stem Cells from Placentas According to Developmental Stage: Comparison to those from Adult Bone Marrow", Journal of Korean Medical Science, 2010, vol. 25, pp. 1418-1426.
Thomson et al., "Isolation of a primate embryonic stem cell line", Proc. Natl. Acad. Sci. USA, vol. 92, pp. 7844-7848, Aug. 1995.
Yamanaka, "Elite and stochastic models for induced pluripotent stem cell generation", Nature, vol. 460, No. 7251, Jul. 2, 2009 (Jul. 2, 2009), pp. 49-52, XP055083198.
Yoon et al., "Clonally expanded novel multipotent stem cells from human bone marrow regenerate myocardium after myocardial infarction", The Journal of Clinical Investigation vol. 115, No. 2, Feb. 2005, pp. 325-338.
Zhang et al. "Isolation and Culture If Bone Marrow Mesenchymal Stem Cells From Human Fetus and Their Biological Properties", Chinese Journal of Agricultural Biotechnology (2008), 5(3), 237-244.
Notice of opposition to a European patent issued in European Patent No. EP2455452, dated Jun. 6, 2018, 27 pages.
Notice of opposition to a European patent issued in European Patent No. EP2455452, dated Jun. 6, 2018, 22 pages.
English translation of the U.S. Appl. No. 61/213,788, filed Jul. 15, 2009, 307 pages.
English translation of the U.S. Appl. No. 61/290,159, filed Dec. 24, 2009, 28 pages.
R Wolkowicz, "Fluorescence-Activated Cell Sorting", Brenner's Encyclopedia of Genetics, 2nd edition, vol. 3, 2013 doi:10.1016/B978-0-12-374984-0.00511-8.
Fisch et al., "Pluripotent nontumorigenic multilineage differentiating stress enduring cells (Muse cells): a seven-year retrospective", Stem Cell research & Therapy (2017) 8:227, DOI 10.1186/s13287-017-0674-3.
Kerkis et al., "Isolation and Characterization of a Population of Immature Dental Pulp Stem Cells Expressing OCT-4 and Other Embryonic Stem Cell Markers", Cells Tissues Organs 2006,184:105-116 (12 pages).
Huang et al., "Isolation of Mesenchymal Stem Cells from Human Placental Decidua Basalis and Resistance to Hypoxia and Serum Deprivation", Stem CeU Rev and Rep (2009) 5:247-255 (9 pages).
Byrne et al., "Enhanced Generation of Induced Pluripotent Stem Cells from a Subpopulation of Human Fibroblasts", PLoS One, Sep. 2009, vol. 4, Issue 9, e7118 (9 pages).

(56) References Cited

OTHER PUBLICATIONS

Kuroda et al., "Unique multipotent cells in adult human mesenchymal cell populations", PNAS, May 11, 2010, vol. 107, No. 19, 8639-8643.
Gimble et al., "Adipose-Derived Stem Cells for Regenerative Medicine", Circulation Research, 2007;100:1249-1260. (12 pages).
Terai et al., "An In Vivo Model for Monitoring Trans-Differentiation of Bone Marrow Cells into Functional Hepatocytes", J. Biochem. 134.561-668 (2003) (11 pages).
Wakao et al., "Multilineage-differentiating stress-enduring (Muse) cells are a primary source of induced pluripotent stem cells in human fibroblasts", PNAS, Jun. 14, 2011, vol. 108, No. 24, 9875-9880 (6 pages).
Yamauchi et al,, "A quantitative analysis of multilineage-differentiating stress-enduring (Muse) cells in human adipose tissue and efficacy of melanocytes induction", Journal of Dermatological Science 86 (2017) 198-205 (8 pages).
Ogura et al., "Human Adipose Tissue Possesses a Unique Population of Pluripotent Stem Cells with Nontumorigenic and Low Telomerase Activities: Potential Implications in Regenerative Medicine", Stem Cells and Development, vol. 23, No. 7, 2014 (12 pages).
Wakao et al., "Muse cells, newly found non-tumorigenic pluripotent stem cells, reside in human mesenchymai tissues", Pathology International 2014, 64: 1-9 (9 pages).
Dezawa, "Muse Cells Provide the Pluripotency of Mesenchymal Stem Cells: Direct Contribution of Muse Cells to Tissue Regeneration", Cell Transplantation, vol. 25, pp. 849-861, 2016 (13 pages).
Kuroda et al., "Isolation, culture and evaluation of multilineage-differentiating stress-enduring (Muse) cells", Nature Protocols, vol. 8 No. 7, 2013 (25 pages).
Kuroda et al., "Unique multipotent cells in adult human mesenchymal cell populations", PNAS, May 11, 2010, vol. 107, No. 19, 8639-8643 (14 pages).
Kerkis et al., "Isolation and Characterization of a Population of Immature Dental Pulp Stem Cells Expressing OCT-4 and Other Embryonic Stem Cell Markers", Cells Tissues Organs 2006,184:105-116 (13 pages).
Yamauchi et al., "A quantitative analysis of multilineage-differentiating stress-enduring (Muse) cells in human adipose tissue and efficacy of melanocytes induction", Journal of Dennatological Science 86 (2017) 198-205 (8 pages).
Wright et al., "Surface marker antigens in the characterization of human embryonic stem cells", Stem Cell Research (2009) 3, 3-11 (9 pages).
Barry et al., "Mesenchymal stem cells: clinical applications and biological characterization", The International Journal of Biochemistry & Cell Biology 36 (2004) 568-584 (17 pages).
Kinoshita et al., "Therapeutic Potential of Adipose-Derived SSEA-3-Positive Muse Cells forTreating Diabetic Skin Ulcers", Stem Cells Translational Medicine Feb. 2015; 4(2): 146-155, doi: 10.5966/sctm.2014-0181.
Gang et al., "SSEA-4 identifies mesenchymal stem cells from bone marrow", Blood, Feb. 15, 2007, vol. 109, No. 4, 1743-1751.
Kushida et al., "Muse Cells Are Endogenous Reparative Stem Cells", M. Dezawa (Ed.), Muse Cells, Advances in Experimental Medicine and Biology, pp. 43-68, 2018.
Shimerman et al., "Muse Cells: Nontumorigenic Pluripotent Stem Cells Present in Adult Tissues—A Paradigm Shift in Tissue Regeneration and Evolution", Stem Cells International, 8 pages, 2016.
Yamada et al., "S1P-S1PR2 Axis Mediates Homing of Muse Cells Into Damaged Heart for Long-Lasting Tissue Repair and Functional Recovery After Acute Myocardial Infarction", Circulation Research, pp. 1069-1083, 2018.
Hua et al., "Characterization of mesenchymal stem cells (MSCs) from human fetal lung: Potential differentiation of germ cells", Tissue and Cell, pp. 448-455, 2009.
Zheng et al., "Human Multipotent Mesenchymal Stromal Cells From Fetal Lung Expressing Pluripotent Markers and Differentiating Into Cell Types of Three Germ Layers", Cell Transplantation, vol. 18, pp. 1093-1109, 2009.
Lee et al., "Potential application of mesenchymal stem cells in acute lung injury", Exprt Opin Biol Ther, pp. 1259-1270, 2009.
Non-Final Office Action dated Mar. 6, 2020 issued in corresponding U.S. Appl. No. 16/104,224.
Office Action dated Jan. 19, 2021 in corresponding Japanese Patent Application No. 2019-2139248, 5 pages.
Nishihara, Shoko: "The Function of Glycan Structures Expressed on Embryonic Stem Cells", Trends In Glycoscience and Glycotechnology , vol. 21, No. 120, (2009) pp. 207-218.
Muramatsu, Takashi et al., "Carbohydrnte markers of ES cells", Trends In Glycoscience and Glycotechnology , vol. 21, No. 120, (2009) pp. 197-206.

\* cited by examiner

Fig. 3

| Gene Symbol | Total | D24 EB body/D24 Native | NHDF EB body/NHDF Native | Gene Title |
|---|---|---|---|---|
| THBD | 1267.42467 | 42.96487494 | 1224.459795 | thrombomodulin |
| IL1RN | 960.4457022 | 12.0038603 | 948.4418419 | interleukin 1 receptor antagonist |
| FOS | 954.4076469 | 88.7202031 | 865.6874438 | v-fos FBJ murine osteosarcoma viral oncogene homolog |
| SLC16A6 | 849.437506 | 715.7799818 | 133.6575242 | solute carrier family 16, member 6 (monocarboxylic acid transporter 7) |
| TYRP1 | 768.3374259 | 11.67216252 | 756.6652634 | tyrosinase-related protein 1 |
| CACNA1A | 685.5302732 | 3.084442121 | 682.445831 | Calcium channel, voltage-dependent, P/Q type, alpha 1A subunit |
| C16orf81 | 531.0858738 | 528.3969782 | 2.688895627 | chromosome 16 open reading frame 81 |
| CHI3L1 | 489.924397 | 373.8511267 | 116.0732704 | chitinase 3-like 1 (cartilage glycoprotein-39) |
| PRSS35 | 441.7622409 | 371.6403738 | 70.12186703 | protease, serine, 35 |
| KYNU | 420.8532931 | 182.1885786 | 238.6647145 | kynureninase (L-kynurenine hydrolase) |
| SLC16A6 | 407.4159044 | 315.8163678 | 91.59953662 | solute carrier family 16, member 6 (monocarboxylic acid transporter 7) |
| APOE | 357.4991884 | 105.5807107 | 251.9184778 | apolipoprotein E |
| THBD | 347.7592226 | 34.12473279 | 313.6344898 | thrombomodulin |
| SYTL5 | 320.0330513 | 15.80876986 | 304.2242814 | synaptotagmin-like 5 |
| CHI3L1 | 299.4142542 | 260.1989748 | 39.21527948 | chitinase 3-like 1 (cartilage glycoprotein-39) |
| ABCA13 | 290.3969665 | 271.9782856 | 18.41868089 | ATP-binding cassette, sub-family A (ABC1), member 13 |
| ANGPTL4 | 284.3113469 | 11.53113972 | 272.7802072 | angiopoietin-like 4 |
| PTGS2 | 273.0706903 | 201.4865123 | 71.58417805 | prostaglandin-endoperoxide synthase 2 (prostaglandin G/H synthase and cyclooxygenase) |
| STC1 | 255.0878156 | 29.28287475 | 225.8049409 | stanniocalcin 1 |
| CCDC102B | 253.1960755 | 37.22467468 | 215.9714008 | coiled-coil domain containing 102B |

Fig. 4

| Gene Symbol | Total | D24 EB/hES | NHDF EB/hES | Gene Title |
|---|---|---|---|---|
| MMP1 | 36528.90821 | 6836.563387 | 29692.34482 | matrix metallopeptidase 1 (interstitial collagenase) |
| EREG | 19813.4402 | 18961.45781 | 851.9823837 | epiregulin |
| CHI3L1 | 9641.34444 | 8842.305483 | 799.038957 | chitinase 3-like 1 (cartilage glycoprotein-39) |
| ——— | 7940.341316 | 7298.64809 | 641.6932268 | Transcribed locus |
| CHI3L1 | 5714.359227 | 5385.877946 | 328.4812811 | chitinase 3-like 1 (cartilage glycoprotein-39) |
| SRGN | 4655.28423 | 4636.821662 | 18.46256778 | serglycin |
| ——— | 4397.855874 | 3959.205654 | 438.6502206 | MRNA full length insert cDNA clone EUROIMAGE 1913076 |
| RIN2 | 3611.379317 | 859.9132609 | 2751.466056 | Ras and Rab interactor 2 |
| LUM | 3396.245648 | 1797.976375 | 1598.269272 | lumican |
| CLCA2 | 3331.259662 | 747.5657674 | 2583.693895 | CLCA family member 2, chloride channel regulator |
| IL8 | 3143.389365 | 2638.045747 | 505.3436182 | interleukin 8 |
| LOC401097 | 3012.485859 | 1860.366679 | 1152.119181 | Similar to LOC166075 |
| DPT | 2807.405266 | 56.39203934 | 2751.013226 | dermatopontin |
| ELTD1 | 2658.65006 | 1751.976082 | 906.6739784 | EGF, latrophilin and seven transmembrane domain containing 1 |
| IGFBP1 | 2423.035758 | 2405.299722 | 17.73603586 | insulin-like growth factor binding protein 1 |
| SLC16A4 | 2305.561138 | 1826.823338 | 478.7378001 | solute carrier family 16, member 4 (monocarboxylic acid transporter 5) |
| SRGN | 2293.730946 | 2279.537455 | 14.19349126 | serglycin |
| GREM2 | 2053.928699 | 159.813291 | 1894.115408 | gremlin 2, cysteine knot superfamily, homolog (Xenopus laevis) |
| IGFBP5 | 1960.755393 | 1915.425977 | 45.3294163 | insulin-like growth factor binding protein 5 |
| SQRDL | 1918.477233 | 1217.387684 | 701.0895492 | sulfide quinone reductase-like (yeast) |

Fig. 7F 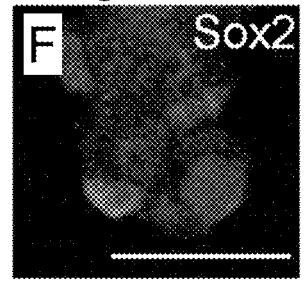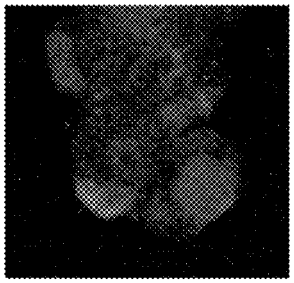

Fig. 8A
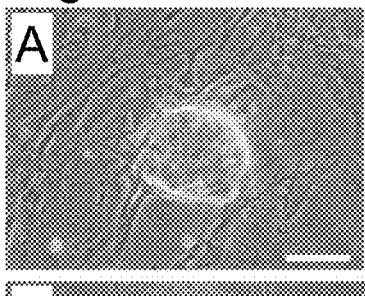
Fig. 8B
Fig. 8C
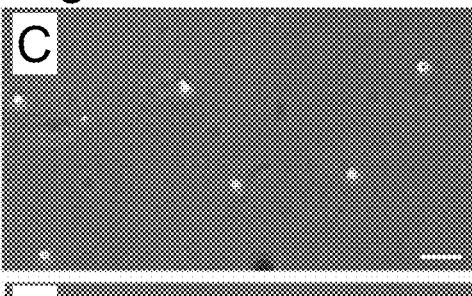
Fig. 8D
Fig. 8E
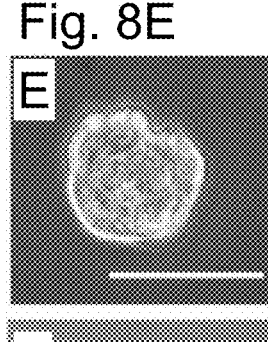
Fig. 8F

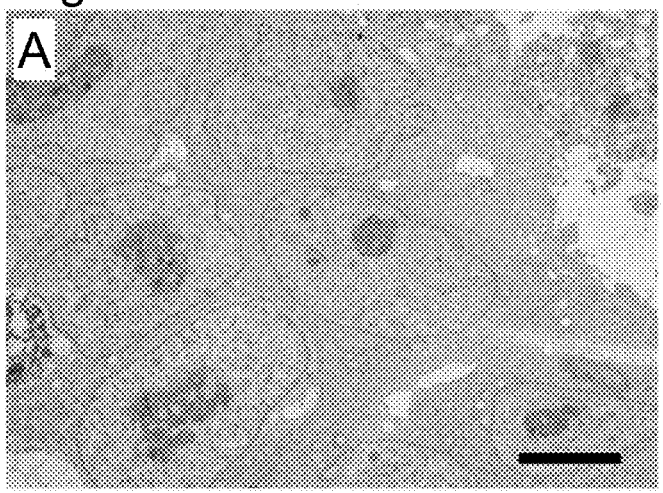
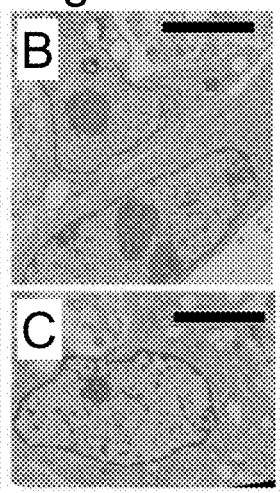
Fig. 11A
Fig. 11B
Fig. 11C

Fig. 15A
Fig. 15B
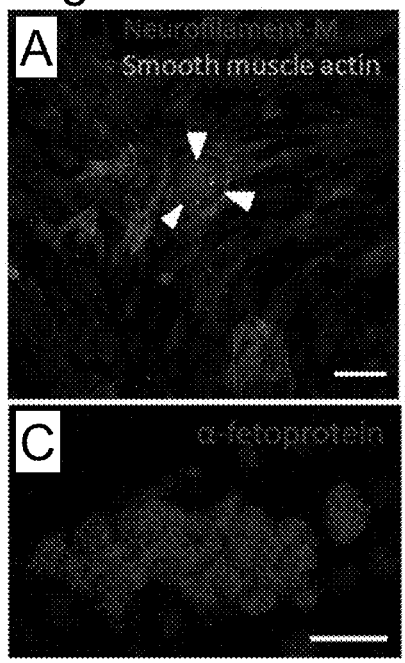
Fig. 15C

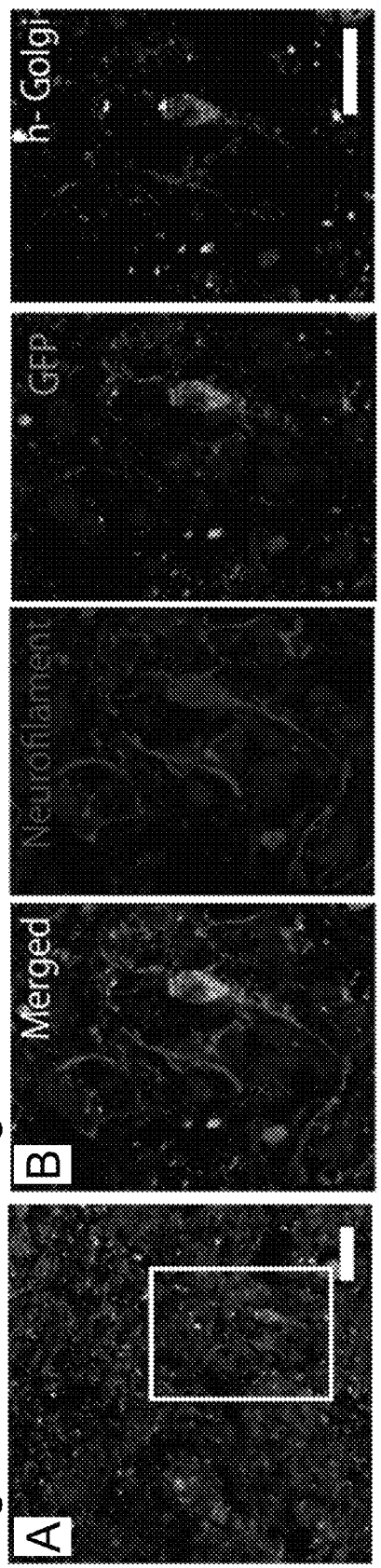
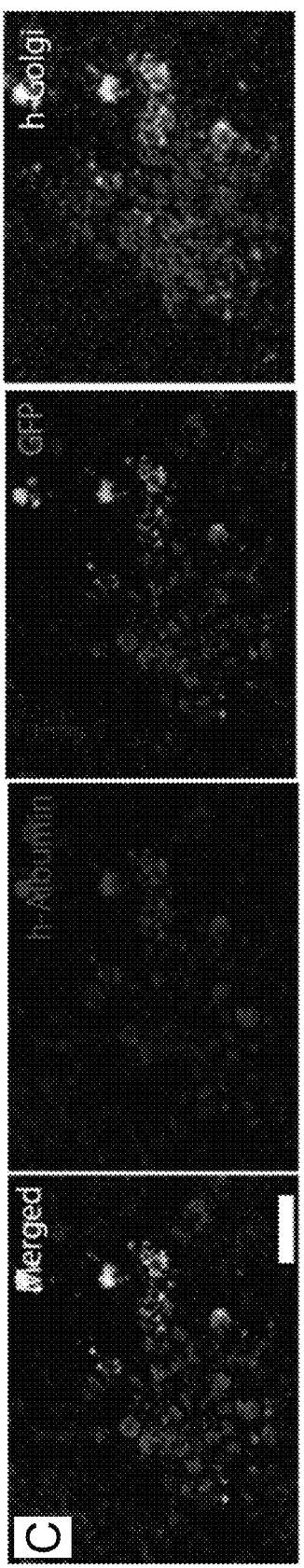
Fig. 28A  Fig. 28B  Fig. 28C

Fig. 34A  Fig. 34B  Fig. 34C
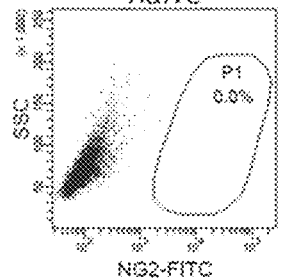
A NG2 naive
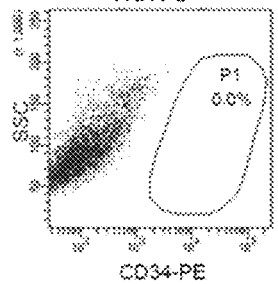
B CD34 naive
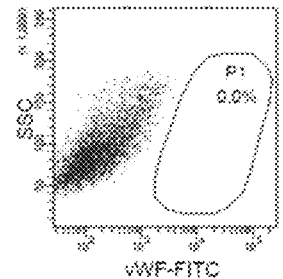
C vWF naive
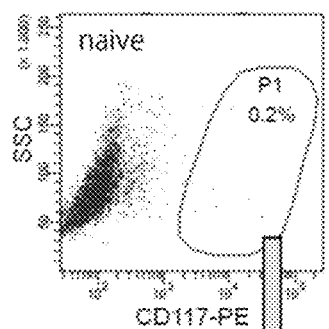
D CD117
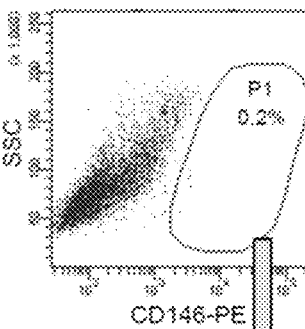
E CD146
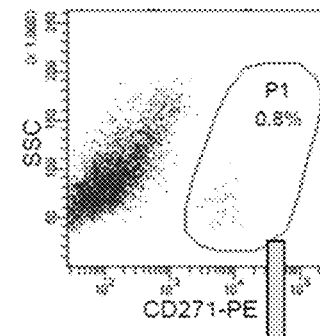
F CD271
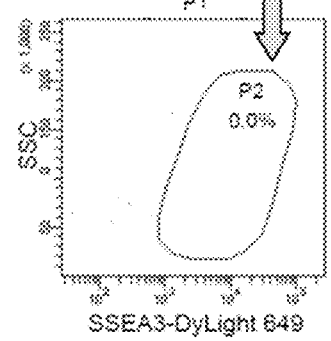
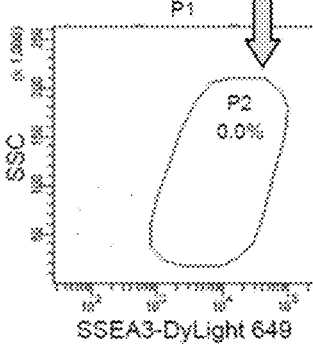
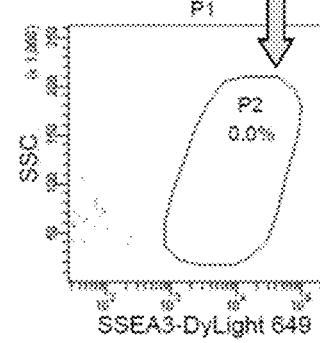
Fig. 34D  Fig. 34E  Fig. 34F

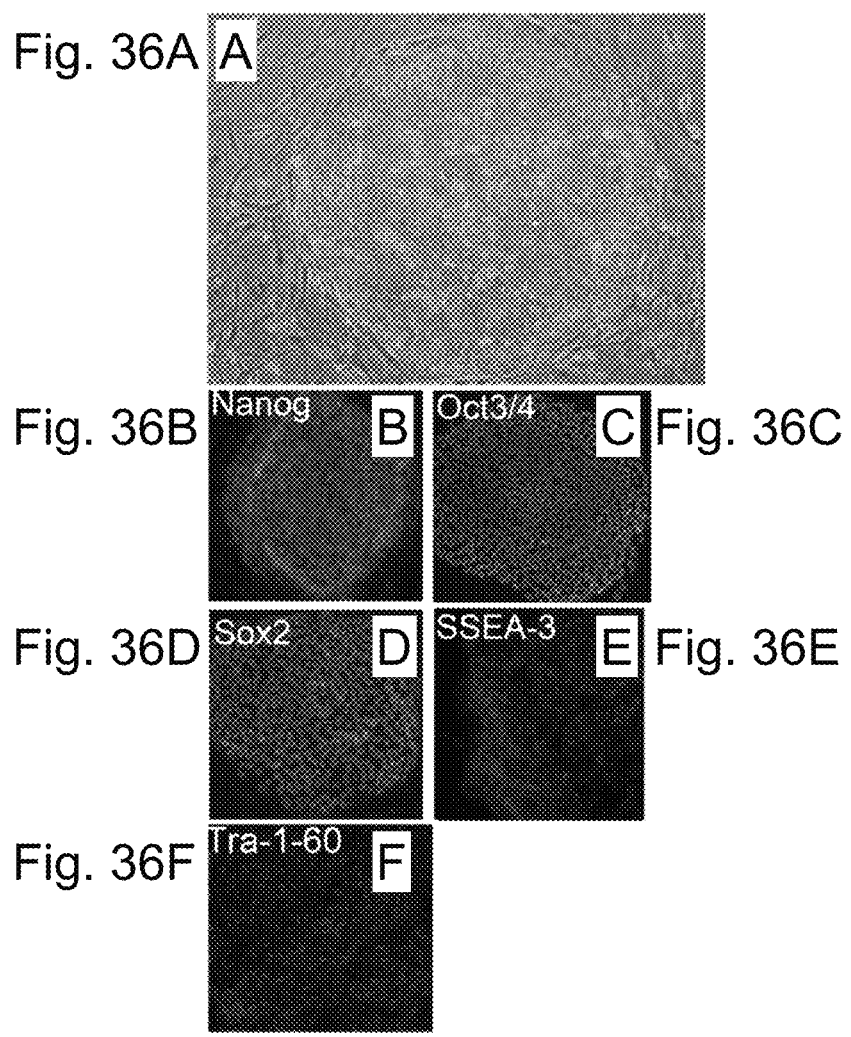

Fig. 41A
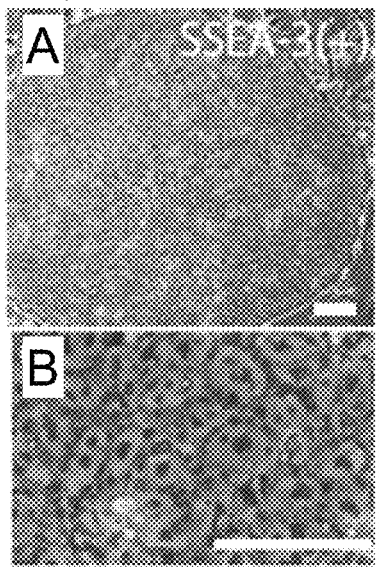
Fig. 41B
Fig. 41C
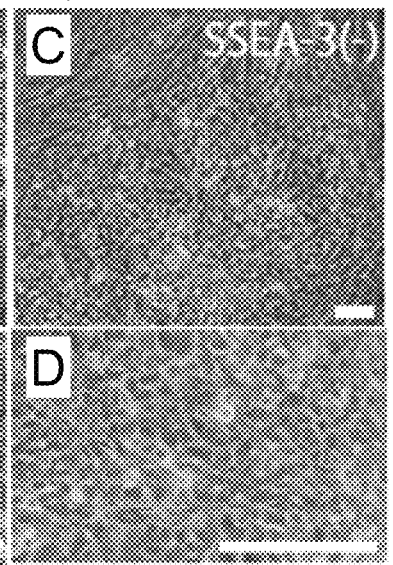
Fig. 41D

| Symbol | Description | /Naive Cluster | /Naive iPS | /iPS Cluster |
|---|---|---|---|---|
| ABL1 | C-abl oncogene 1, receptor tyrosine kinase | | | 1.2E+00 |
| ANAPC2 | Anaphase promoting complex subunit 2 | | | 8.5E-01 |
| ANAPC4 | Anaphase promoting complex subunit 4 | | ■ | 5.0E-01 |
| ATM | Ataxia telangiectasia mutated | | ■ | 1.7E+00 |
| ATR | Ataxia telangiectasia and Rad3 related | | | 9.5E-01 |
| BRCA1 | Breast cancer 1, early onset | | ■ | 1.3E-01* |
| CCNB1 | Cyclin B1 | | ■ | 5.9E-02* |
| CCNB2 | Cyclin B2 | | ■ | 6.6E-02* |
| CCNC | Cyclin C | | ■ | 2.2E-01* |
| CCND1 | Cyclin D1 | | ▨ | 3.7E+00** |
| CCND2 | Cyclin D2 | ▨ | ■ | 3.7E-02* |
| CCNE1 | Cyclin E1 | | ■ | 1.0E-01* |
| CCNF | Cyclin F | | ■ | 1.1E-01* |
| CCNG1 | Cyclin G1 | | | 4.1E-01 |
| CCNG2 | Cyclin G2 | ■ | ▨ | 1.1E+01** |
| CCNH | Cyclin H | | | 6.6E-01 |
| CCNT1 | Cyclin T1 | | ■ | 5.8E-01 |
| CCNT2 | Cyclin T2 | | ■ | 4.0E-01 |
| CDC16 | Cell division cycle 16 homolog (S. cerevisiae) | | | 3.3E-01* |
| CDC2 | Cell division cycle 2, G1 to S and G2 to M | | | 6.4E-02* |
| CDC20 | Cell division cycle 20 homolog (S. cerevisiae) | ▨ | | 3.3E-02* |
| CDC34 | Cell division cycle 34 homolog (S. cerevisiae) | | | 4.7E-01 |
| CDK2 | Cyclin-dependent kinase 2 | | ■ | 3.0E-01* |
| CDK4 | Cyclin-dependent kinase 4 | | ■ | 6.4E-01 |
| CDK5R1 | Cyclin-dependent kinase 5, regulatory subunit 1 (p35) | | ■ | 2.2E-01* |
| CDK5RAP1 | CDK5 regulatory subunit associated protein 1 | | ■ | 3.2E-01* |
| CDK6 | Cyclin-dependent kinase 6 | ▨ | | 5.7E-01 |
| CDK7 | Cyclin-dependent kinase 7 | | ■ | 3.5E-01 |
| CDK8 | Cyclin-dependent kinase 8 | | ■ | 4.7E-01 |
| CDKN1A | Cyclin-dependent kinase inhibitor 1A (p21, Cip1) | | ▨ | 8.3E+01** |
| CDKN1B | Cyclin-dependent kinase inhibitor 1B (p27, Kip1) | | | 8.2E-01 |
| CDKN2A | Cyclin-dependent kinase inhibitor 2A (melanoma, p16, inhibits CDK4) | ■ | ▨ | 3.7E+02** |
| CDKN2B | Cyclin-dependent kinase inhibitor 2B (p15, inhibits CDK4) | ■ | ▨ | 7.8E+01** |
| CDKN3 | Cyclin-dependent kinase inhibitor 3 (CDK2-associated dual specificity phosphatase) | ▨ | | 1.3E-01* |
| CHEK1 | CHK1 checkpoint homolog (S. pombe) | | ■ | 1.7E-01* |
| CHEK2 | CHK2 checkpoint homolog (S. pombe) | | ■ | 7.7E-02* |
| CUL1 | Cullin 1 | | | 4.2E-01 |
| E2F4 | E2F transcription factor 4, p107/p130-binding | | | 4.8E-01 |
| GADD45A | Growth arrest and DNA-damage-inducible, alpha | | ▨ | 5.1E+00** |
| MAD2L1 | MAD2 mitotic arrest deficient-like 1 (yeast) | | ■ | 4.4E-02* |
| MAD2L2 | MAD2 mitotic arrest deficient-like 2 (yeast) | | ■ | 8.2E-02* |
| MCM2 | Minichromosome maintenance complex component 2 | | ■ | 5.6E-02* |
| MCM3 | Minichromosome maintenance complex component 3 | | ■ | 5.7E-02* |
| MCM4 | Minichromosome maintenance complex component 4 | ■ | | 2.2E-01* |
| MCM5 | Minichromosome maintenance complex component 5 | | ■ | 3.3E-02* |
| MNAT1 | Menage a trois homolog 1, cyclin H assembly factor (Xenopus laevis) | | | 6.8E-01 |
| MRE11A | MRE11 meiotic recombination 11 homolog A (S. cerevisiae) | | ■ | 3.7E-01 |
| PCNA | Proliferating cell nuclear antigen | | | 2.0E-01* |
| RAD51 | RAD51 homolog (RecA homolog, E. coli) (S. cerevisiae) | | ■ | 7.0E-02* |
| RB1 | Retinoblastoma 1 (including osteosarcoma) | | ▨ | 4.0E+00** |
| RBBP8 | Retinoblastoma binding protein 8 | | | 1.8E-01* |
| RBL1 | Retinoblastoma-like 1 (p107) | | | 2.3E-01* |
| RBL2 | Retinoblastoma-like 2 (p130) | | ▨ | 5.5E+00** |
| RPA3 | Replication protein A3, 14kDa | | | 1.3E-01* |
| SKP2 | S-phase kinase-associated protein 2 (p45) | ▨ | | 1.2E-01* |
| TERT | Telomerase reverse transcriptase | | ■ | 0.0E+00* |
| TFDP1 | Transcription factor Dp-1 | | | 8.4E-01 |
| TFDP2 | Transcription factor Dp-2 (E2F dimerization partner 2) | | ■ | 6.6E-01 |
| TP53 | Tumor protein p53 | | ■ | 3.3E-01* |

Fig. 47

| Symbol | Description | /Naive Cluster | /Naive iPS | /iPS Cluster |
|---|---|---|---|---|
| ABCA13 | ATP-binding cassette, sub-family A (ABC1), member 13 | | | 4.1E-01 |
| ALPL | Alkaline phosphatase, liver/bone/kidney | | | 2.9E-03* |
| ATRX | Alpha thalassemia/mental retardation syndrome X-linked (RAD54 homolog, S. cerevisiae) | | | 9.9E-01 |
| BMP4 | Bone morphogenetic protein 4 | | | 1.4E-01* |
| BMPR1A | Bone morphogenetic protein receptor, type IA | | | 6.6E-01 |
| CBX7 | Chromobox homolog 7 | | ▨ | 5.5E+00** |
| CTR9 | Ctr9, Paf1/RNA polymerase II complex component, homolog (S. cerevisiae) | | | 6.2E-01 |
| DAZL | Deleted in azoospermia-like | | | 5.8E-02* |
| DDX4 | DEAD (Asp-Glu-Ala-Asp) box polypeptide 4 | | | 5.0E-01 |
| DNMT1 | DNA (cytosine-5-)-methyltransferase 1 | | | 2.1E-01* |
| DNMT3B | DNA (cytosine-5-)-methyltransferase 3 beta | | | 6.2E-04* |
| DPPA2 | Developmental pluripotency associated 2 | | | 1.6E-03* |
| DPPA3 | Developmental pluripotency associated 3 | | | 1.1E-02* |
| DPPA4 | Developmental pluripotency associated 4 | | | 1.1E-04* |
| EPC1 | Enhancer of polycomb homolog 1 (Drosophila) | | | 8.2E-01 |
| ERAS | ES cell expressed Ras | | | 1.1E-01* |
| F11R | F11 receptor | | | 2.0E-03* |
| FGFR1 | Fibroblast growth factor receptor 1 (fms-related tyrosine kinase 2, Pfeiffer syndrome) | | | 5.8E-01 |
| FOXD3 | Forkhead box D3 | | | 4.2E-04* |
| GDF3 | Growth differentiation factor 3 | | | 0.0E+00* |
| GRB7 | Growth factor receptor-bound protein 7 | | | 1.8E-03* |
| HAND1 | Heart and neural crest derivatives expressed 1 | | | 1.9E-02* |
| HES1 | Hairy and enhancer of split 1, (Drosophila) | | | 1.4E+00 |
| HEXIM1 | Hexamethylene bis-acetamide inducible 1 | | | 2.8E+00 |
| HOXB1 | Homeobox B1 | | | 4.7E-02* |
| ID1 | Inhibitor of DNA binding 1, dominant negative helix-loop-helix protein | | | 3.3E+00** |
| ID3 | Inhibitor of DNA binding 3, dominant negative helix-loop-helix protein | | | 3.0E+00** |
| IFITM1 | Interferon induced transmembrane protein 1 (9-27) | | | 1.7E-01* |
| KCNK3 | Potassium channel, subfamily K, member 3 | | | 3.4E+00** |
| KITLG | KIT ligand | | ▨ | 1.2E+01** |
| KLF4 | Kruppel-like factor 4 (gut) | | | 1.0E+00 |
| LIN28 | Lin-28 homolog (C. elegans) | | | 3.5E-04* |
| MSX2 | Msh homeobox 2 | | | 3.8E-01 |
| MYC | V-myc myelocytomatosis viral oncogene homolog (avian) | | | 7.6E-01 |
| NANOG | Nanog homeobox | | | 4.0E-04* |
| NAT1 | N-acetyltransferase 1 (arylamine N-acetyltransferase) | | | 9.4E-01 |
| NKX1-2 | NK1 homeobox 2 | | | 2.3E-03* |
| NR0B1 | Nuclear receptor subfamily 0, group B, member 1 | | | 2.4E+01** |
| OCT3/4 | POU class 5 homeobox 1 | | | 1.8E-02* |
| OTX2 | Orthodenticle homeobox 2 | | | 0.0E+00* |
| PAN3 | PAN3 polyA specific ribonuclease subunit homolog (S. cerevisiae) | | | 4.5E-01 |
| PODXL | Podocalyxin-like | | | 3.8E-02* |
| PRDM1 | PR domain containing 1, with ZNF domain | | | 1.0E+01** |
| RAG1AP1 | Recombination activating gene 1 activating protein 1 | | | 8.6E-01 |
| SALL4 | Sal-like 4 (Drosophila) | | | 6.4E-04* |
| SIX4 | SIX homeobox 4 | | | 9.9E-01 |
| SOX2 | SRY (sex determining region Y)-box 2 | | | 7.4E-04* |
| SPAG9 | Sperm associated antigen 9 | | | 1.3E+00 |
| SPRY1 | Sprouty homolog 1, antagonist of FGF signaling (Drosophila) | | | 5.1E-01 |
| SPRY2 | Sprouty homolog 2 (Drosophila) | | | 1.9E+00 |
| SSBP2 | Single-stranded DNA binding protein 2 | | | 1.7E+00 |
| STAT3 | Signal transducer and activator of transcription 3 (acute-phase response factor) | | | 1.6E+00 |
| TDGF1 | Teratocarcinoma-derived growth factor 1 | | | 3.8E-05* |
| TFE3 | Transcription factor binding to IGHM enhancer 3 | | | 1.1E+00 |
| TRDMT1 | TRNA aspartic acid methyltransferase 1 | | | 7.3E-01 |
| UTF1 | Undifferentiated embryonic cell transcription factor 1 | | | 0.0E+00* |
| VIM | Vimentin | | ▨ | 1.4E+02** |

Fig. 48

| Animal | Reprogramming factor [b] | Cell type | Time (week) | Efficiency |
|---|---|---|---|---|
| Mouse | Viral-integrating vectors | | | |
| | O, K, S, M | MEFs | 2-3 | 0.01-0.50% |
| | O, K, S, M | Hepatocyte | 2-3 | 1-3% |
| | O, K, S, M | Gastric epithelial cell | 2-3 | 1-3% |
| | O, K, S, M | B cell | 2-3 | 0.01-0.10% |
| | O, K, S, M | β cell | 3-4 | 0.1-0.2% |
| | O, K, S, M | Neural stem cell | 1-2 | 3-5% |
| | O, K, S | MEFs | 3-4 | 0.001-0.010% |
| | O, K, S | Hepatocyte | 2-3 | 0.5-1.0% |
| | O, K, M | Neural stem cell | 1-2 | 0.1-1.0% |
| | O, K, | Neural stem cell | 2-3 | 0.1-1.0% |
| | O, M, S | Neural stem cell | 3-4 | 0.1-1.0% |
| | O, K | Neural stem cell | 2-3 | 0.1-0.2% |
| | O, M | Neural stem cell | 3-4 | 0.1-0.2% |
| | Non-integrating viral vectors [c] | | | |
| | O, K, S, M | Hepatocyte | 4-5 | 0.0001 to 0.0010% |
| | Plasmid-based vedtros [c] | | | |
| | O, K, S, M | MEFs | 3-4 | 0.0001 to 0.0010% |
| Human | Viral-integrating vectors | | | |
| | O, K, S, M | Dermal fibroblast | 4-5 | 0.001-0.002% |
| | O, K, L, N | Dermal fibroblast | 2-3 | N.D. |
| | O, K, S, M | Bone marrow stromal cell | 2-3 | N.D. |
| | O, K, N | Dermal fibroblast | 2-3 | N.D. |
| | O, K, L | Dermal fibroblast | 2-3 | N.D. |
| | O, S, K [d] | Dermal fibroblast | 4 | 0.1-1.0% |
| | O, S [d] | Dermal fibroblast | 4 | 0.001-0.010% |
| | O, S, L, N [e] | Dermal fibroblast | | 0.002% |
| | O, K, S, M, T, LT | Dermal fibroblast | | 0.0417% |
| | O, K, S, M, p, U | Dermal fibroblast | | N.D. |

MEFs, Mouse embryonic fibroblast ; N.D., not determined.

[b] O, Oct4; S, Sox2; M, c-Myc; K, Klf4; N, Nanog; L, Lin28; T, hTERT; LT, Large T antigen; p, p53RNAi; U, Utf1
[c] Integration-free clones.
[d] Valpronic acid (VPA) used in association
[e] CHIR99021, PD0325901, A-83-01

Fig. 50

| Name | | 5'-sequence-3' | |
|---|---|---|---|
| β-actin | sense | AGGCGGACTATGACTTAGTTGCGTTACACC | (SEQ ID NO:1) |
| | antisense | AAGTCCTCGGCCACATTGTGAACTTTG | (SEQ ID NO:2) |
| Nkx2.5 | sense | GGGACTTGAATGCGGTTCAG | (SEQ ID NO:3) |
| | antisense | CTCCACAGTTGGGTTCATCTGTAA | (SEQ ID NO:4) |
| AFP | sense | CCACTTGTTGCCAACTCAGTGA | (SEQ ID NO:5) |
| | antisense | TGCAGGAGGGACATATGTTTCA | (SEQ ID NO:6) |
| MAP-2 | sense | ACTACCAGTTTCACACCCCCTTT | (SEQ ID NO:7) |
| | antisense | AAGGGTGCAGGAGACACAGATAC | (SEQ ID NO:8) |
| GATA6 | sense | CCTGCGGGCTCTACAGCAAGATGAAC | (SEQ ID NO:9) |
| | antisense | CGCCCCTGAGGCTGTAGGTTGTGTT | (SEQ ID NO:10) |

| Name | negative control | positive control |
|---|---|---|
| Nkx2.5 | Human adult liver | Human whole embryo |
| AFP | Human adult brain | Human fetus liver |
| MAP-2 | Human adult liver | Human whole embryo |
| GATA6 | Human adult brain | Human whole embryo |

Bar=50μm

Fig. 55A
Fig. 55B
Fig. 55C
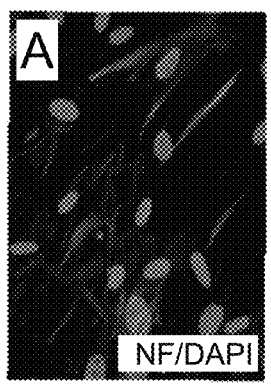
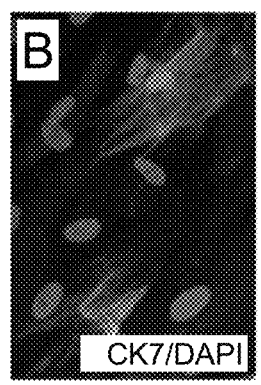
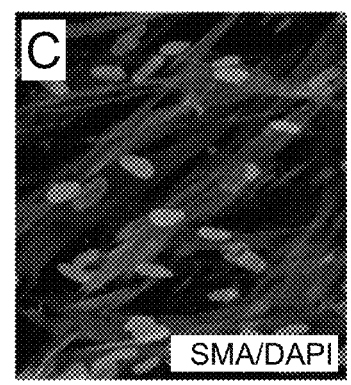

Bar=10mm

Fig. 59A
Fig. 59B
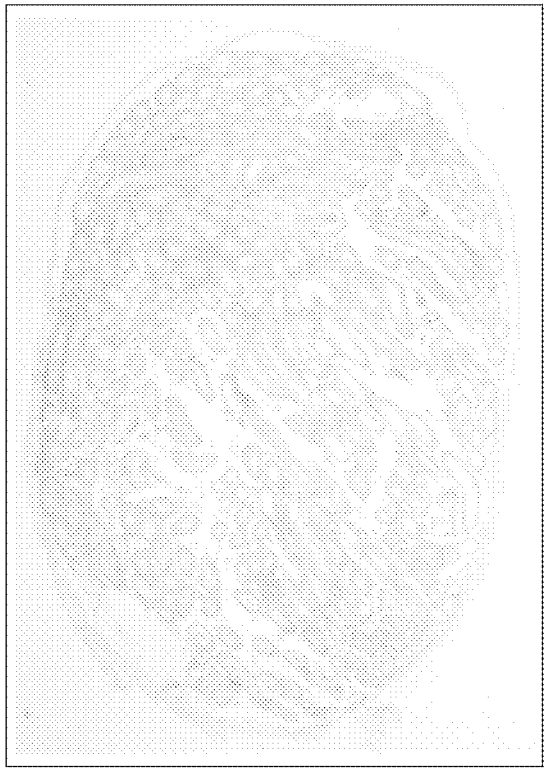

Fig. 62
hUC-T3 (p=8) DMEM
1. No stain
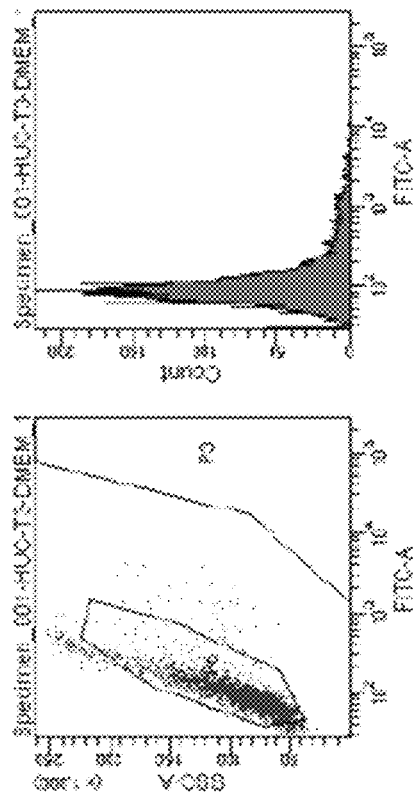
2. Only 2nd antibody
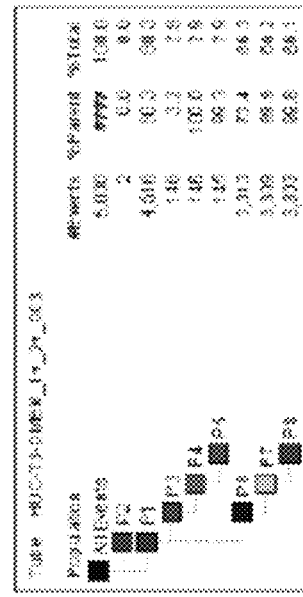
3. Stain
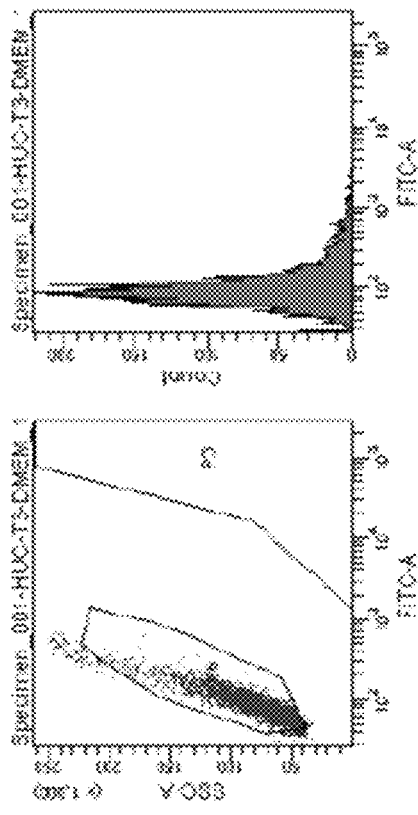
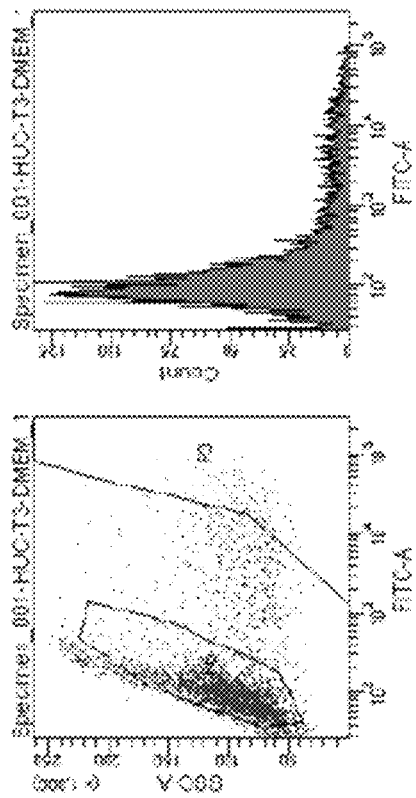

Fig. 71A 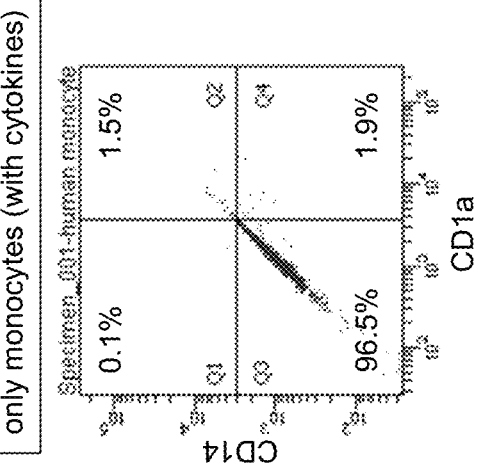 Fig. 71E 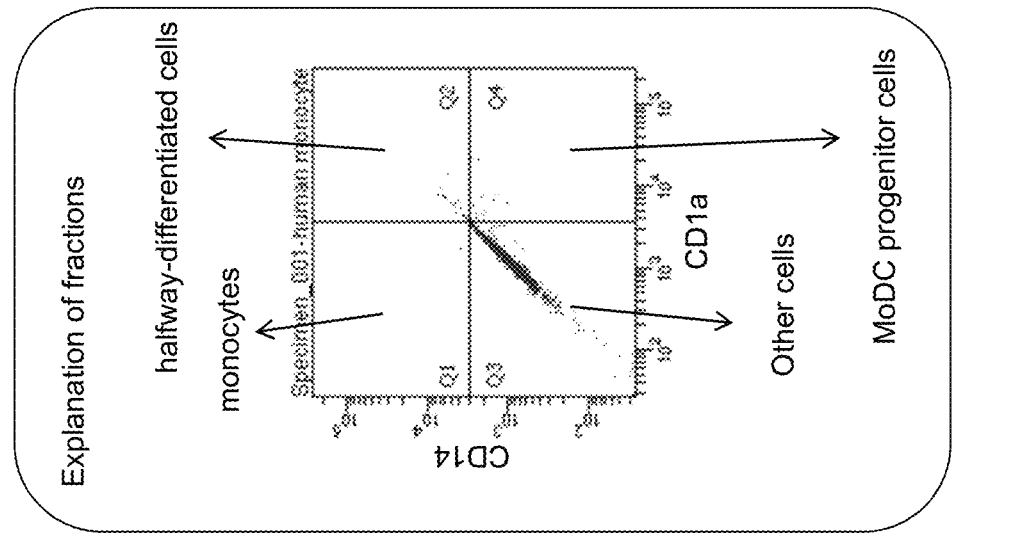
Fig. 71B

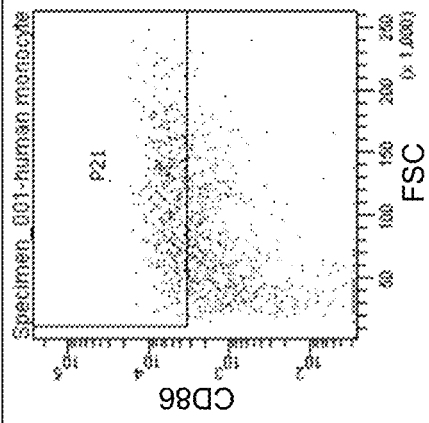
Fig. 73A (i) only MoDC progenitors (without cytokines)
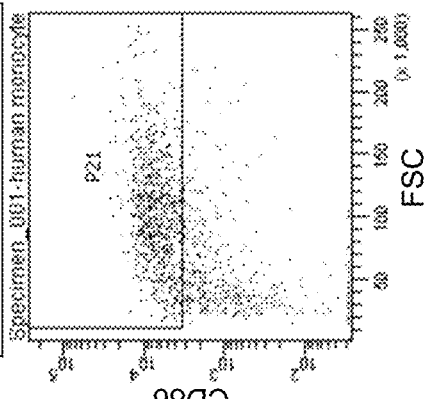
Fig. 73B (ii) only MoDC progenitors (with cytokines)
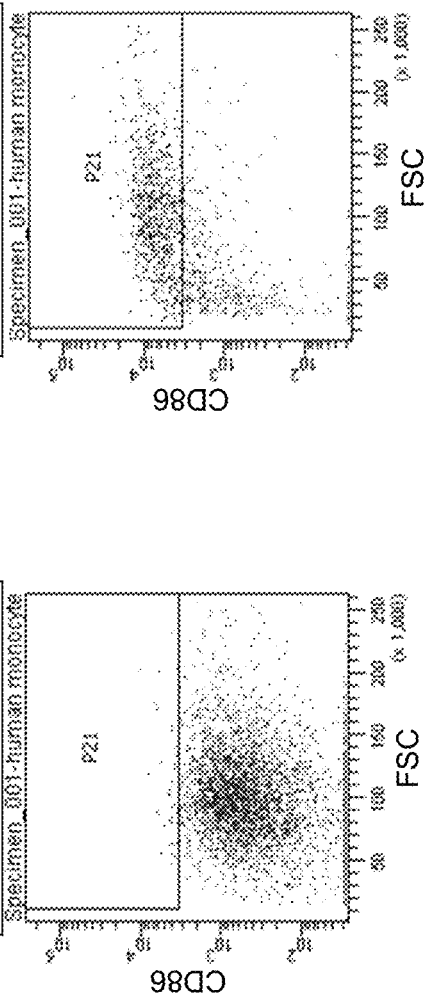
Fig. 73C (iii) only MoDC progenitors (with cytokines + CyclosporineA)
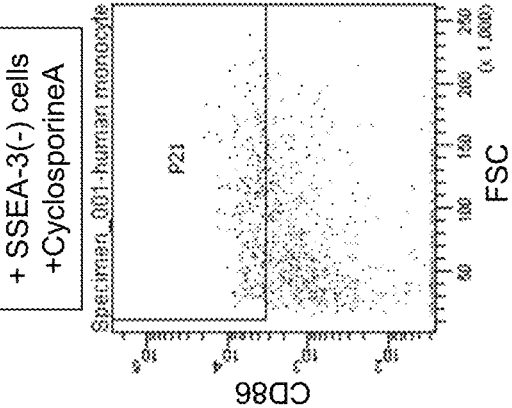
Fig. 73D (iv) MoDC progenitors + SSEA-3(+) cells
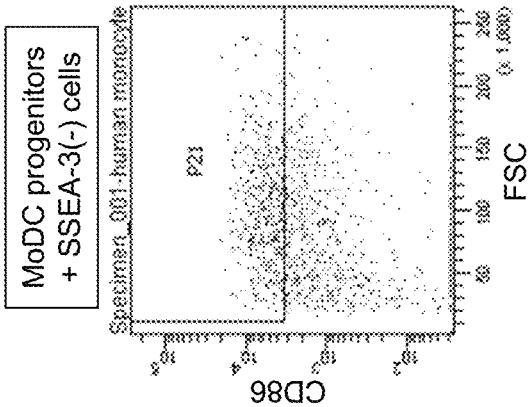
Fig. 73E (v) MoDC progenitors + SSEA-3(+) cells +CyclosporineA
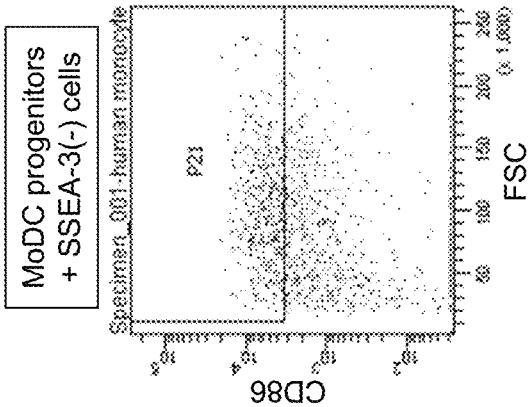
Fig. 73F (vi) MoDC progenitors + SSEA-3(-) cells
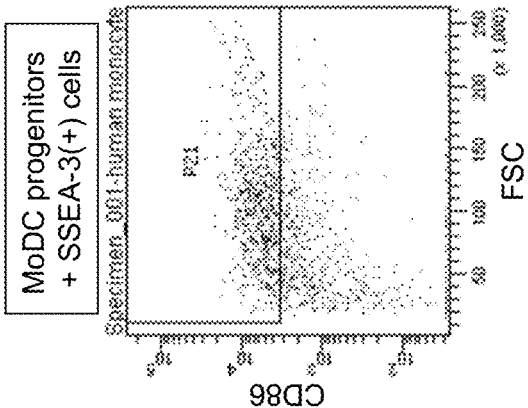
Fig. 73G (vii) MoDC progenitors + SSEA-3(-) cells +CyclosporineA

```
SEQUENCE LISTING

<160> NUMBER OF SEQ ID NOS: 10

<210> SEQ ID NO 1
<211> LENGTH: 30
<212> TYPE: DNA
<213> ORGANISM: Artificial
<220> FEATURE:
<223> OTHER INFORMATION: primer

<400> SEQUENCE: 1
aggcggacta tgacttagtt gcgttacacc                                          30

<210> SEQ ID NO 2
<211> LENGTH: 27
<212> TYPE: DNA
<213> ORGANISM: Artificial
<220> FEATURE:
<223> OTHER INFORMATION: primer

<400> SEQUENCE: 2
aagtcctcgg ccacattgtg aactttg                                             27

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
gggacttgaa tgcggttcag                                                     20

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
```
ctccacagtt gggttcatct gtaa                     24

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
ccacttgttg ccaactcagt ga                       22

<210> SEQ ID NO 6
<211> LENGTH: 22
<212> TYPE: DNA
<213> ORGANISM: Artificial
<220> FEATURE:
<223> OTHER INFORMATION: primer

<400> SEQUENCE: 6
tgcaggaggg acatatgttt ca                       22

<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
actaccagtt tcacaccccc ttt                      23

<210> SEQ ID NO 8
<211> LENGTH: 23
<212> TYPE: DNA
<213> ORGANISM: Artificial
<220> FEATURE:
<223> OTHER INFORMATION: primer

<400> SEQUENCE: 8
aagggtgcag gagacacaga tac                      23

<210> SEQ ID NO 9
<211> LENGTH: 26
<212> TYPE: DNA
<213> ORGANISM: Artificial
<220> FEATURE:
<223> OTHER INFORMATION: primer

<400> SEQUENCE: 9
cctgcgggct ctacagcaag atgaac                   26

<210> SEQ ID NO 10
<211> LENGTH: 25
<212> TYPE: DNA
<213> ORGANISM: Artificial
<220> FEATURE:
<223> OTHER INFORMATION: primer

<400> SEQUENCE: 10
cgcccctgag gctgtaggtt gtgtt                    25

PLURIPOTENT STEM CELL THAT CAN BE ISOLATED FROM BODY TISSUE

BACKGROUND OF THE INVENTION

Field of the Invention

The present invention relates to body tissue-derived Pluripotent stem cells.

Background Art

Planarians and newts can regenerate their entire bodies even after their bodies have been cut. Such high regenerative capacity of planarians and newts depends on the presence of pluripotent stem cells existing in the mesenchymal tissues. However, in the case of higher organisms such as humans, the tissue regenerative capacity is far lower than that of those animals. Cells of inner cell mass in a mammalian blastocyst is recognized as pluripotent stem cells that is capable of differentiating into cells of ectodermal, mesodermal, and endodermal cell lineages. However, such broad spectrum of differentiation ability becomes limited as development proceeds, followed by cell differentiation for specialization resulting in each type of tissue, and thus, unlike planarians and newts, pluripotent stem cell are not considered to be residing in the living body of higher mammals.

Bone marrow stromal cell (MSC) fractions are known to having the ability to differentiate into bone, cartilage, adipocytes, neuronal cells and skeletal muscles by induction, and the like have been reported as cells having differentiation potency obtained from an adult (see Non-Patent Documents 1 and 2). However, bone marrow stromal cells (MSCs) are comprised of various cell kinds, and thus cells responsible for the differentiation of MSC fraction are not clearly understood. Furthermore, induction of MSCs requires stimulation with a specific compound, gene transfer, or the like for differentiation of MSCs into specific cells. Specifically, there is a need to construct a system for inducing differentiation.

Furthermore, there have been reported that when MSCs are infused into living body, a small part of MSC fractions are known to home into damaged tissues and differentiate into tissue specific cells and contribute to repair. Such tissue repair was observed in tissues and organs of endodermal-, ectodermal- and mesodermal origins. However, the cells responsible for the repair remained an enigma.

iPS cells (induced pluripotent stem cells) (see Patent document 1, Patent document 2, Non-patent document 3, and the like) have been reported as adult-derived pluripotent stem cells. However, establishment of iPS cells requires an artificial operation using a specific substance, such as introduction of a specific gene into mesenchymal cell fraction (for example, a dermal fibroblast fraction) or introduction of a specific compound into somatic cells. While iPS can generate cell of all three germ layers, their tumorigenicity pose limitation for clinical application.

Patent document 1 JP Patent No. 4183742

Patent document 2 JP Patent Publication (Kokai) No. 2008-307007 A

Non-patent document 1 M. DEZAWA et al., The Journal of Clinical Investigation, 113, 12, pp. 1701-1710, (2004)

Non-patent document 2 M. DEZAWA et al., SCIENCE, 2005 Jul. 8, 309, pp. 314-317, (2005)

Non-patent document 3 Okita K. et al. SCIENCE, 2008 Nov. 7, 322 (5903), pp. 949-953

SUMMARY OF THE INVENTION

An object of the present invention is to provide a method for directly obtaining pluripotent stem cells from body tissue and pluripotent stem cells obtained by the method. As described in "Background Art", there are pluripotent stem cells existing in mesenchymal tissues in some lower animals. The present inventors newly found that the novel type of pluripotent stem cells can be isolated from body tissues of a living animals without artificial manipulation such as introduction of exogenous genes. The expressed antigens of the novel pluripotent stem cells differ from those of the conventionally reported pluripotent stem cells. The pluripotent stem cells can self-renew and can differentiate into endodermal, ectodermal, and mesodermal cells whereas they do not have tumorigenicity. Accordingly, the present invention enables that pluripotent stem cells with higher safety can be isolated from body tissues of a human.

The present inventors have discovered that in the research process of culturing bone marrow stromal cell (MSC: bone marrow stromal cell) fractions in ordinary adherent culture, characteristic cell clusters are spontaneously formed at very low frequency from untreated (naive) human and rodent MSC cells. The appearance of initial cell clusters closely resembles that of ES cell-derived embryoid body. However, unlike ES cells, the cell clusters do not undergo infinite growth. They stop growth when they reach a size within a certain period and then they form heterogeneous populations containing various cells such as hair cells and pigment cells. Together with hairs and pigment cells, cells positive for ectodermal, endodermal, and mesodermal markers were shown to be contained in a single cell cluster by immunocytochemistry. The present inventors considered from the results the possible presence of cells equivalent to pluripotent cells in untreated (naive) human MSC cell fractions that are generally maintained and cultured. The present inventors then further intensively studied the matter.

The present inventors have discovered that SSEA-3 is expressed as a surface antigen of the above pluripotent stem cells and that the above pluripotent stem cells can also be isolated from body tissue using SSEA-3 expression as a marker. The present inventors further found that the pluripotent stem cells can also be isolated from body tissue using both of SSEA-3 and CD105 expressions as markers. SSEA-3 is a pluripotent stem cell marker and CD105 is a mesenchymal marker. The pluripotent stem cells of the present invention can be isolated by using SSEA-3 only as a marker. However, when the pluripotent stem cells are isolated from tissues which contain elements other than mesenchymal lineage, combine use of SSEA-3 and CD105 is effective.

When isolated SSEA-3(+) were cultured in suspension either in single cell suspension culture or in methylcellulose (MC)-containing medium (called "MC culture"), single SSEA-3(+) cells start to proliferate, form characteristic cell cluster (from 25 μm to up to a maximum diameter of 150 μm) resembling embryoid body of human ES cells. The cluster express pluripotency markers such as Nanog, Oct3/4 and Sox2, was positive for alkaline phosphatase reaction. Importantly, the cluster formed from a single SSEA-3(+) cell generated ectodermal-, endodermal- and mesodermal-lineage cells when transferred onto gelatin culture to induce spontaneous differentiation, demonstrating that SSEA-3(+) cell has the ability to generate cells representative of all three germ layers. Furthermore, SSEA-3(+) cell showed the ability to self-renew. A "pluripotent stem cell" is defined as that having the ability to give rise to cell types of all three embryonic germ layers, namely endodermal, mesodermal, and ectodermal cells from a single cells, and that having the ability to self-renew, the invented cell is pluripotent stem cell.

It is known that when a body is exposed to stress or injured, tissue stem cells in a dormant state are activated, contributing to tissue regeneration. The present inventors have provided stimulation stress to mesenchymal cells such as bone marrow stromal cell (MSC) fractions and dermal fibroblast fractions while culturing them according to various methods (e.g., serum free culture, culture using Hank's Balanced Salt Solution (HBSS), low oxygen culture, a total of 3 hours of intermittent short-time trypsin culture, and 8 or 16 hours of long-time trypsin incubation), collected surviving cells, and then performed suspension culture in MC culture. As a result, formation of embryoid body-like cell clusters (up to a maximum diameter of 150 μm) was confirmed as described above. In particular, embryoid body-like cell cluster formation was confirmed at the highest frequency in human dermal fibroblast fractions and human MSC fractions subjected to long-term trypsin incubation. The property of formed cluster by stress stimulation was identical to those of SSEA-3(+) cells, thus the stress stimulation is found to be effective method to enrich the pluripotent stem cells.

The present inventors have also discovered that the above pluripotent stem cells are novel type of pluripotent stem cells that differ from conventionally reported pluripotent stem cells such as ES cells and iPS cells. Specifically, the present inventors have discovered that the pluripotent stem cells can be directly obtained from body tissue without any induction operation. The present inventors have also discovered that the pluripotent stem cells show low or no telomerase activity and do not show tumorigenic proliferative activity.

The present inventors have further discovered that cells in the obtained embryoid body-like cell clusters had properties which were not possessed by the pluripotent stem cells which have been previously reported. The present inventors have further examined proteins expressed by cells in the obtained cell clusters, and thus they have discovered that the cells exert expression patterns differing from those exerted by conventionally reported pluripotent stem cells such as ES cells and iPS cells.

Thus, the present inventors have completed the present invention. The present inventors have designated the pluripotent stem cells Muse cells (Multilineage-differentiating Stress Enduring cells).

The present invention is as follows.
[1] A SSEA-3-positive pluripotent stem cell, which can be isolated from body tissue.

The pluripotent stem cells can be isolated from a culture product of body tissue such as cultured fibroblasts and myeloid stem cells and can also be isolated in the form of single cells.
[2] The pluripotent stem cell according to [1], which is positive for mesenchymal marker CD105.
[3] The pluripotent stem cell according to [1] or [2], which is negative for CD117 (c-Kit) and negative for CD146.
[4] The pluripotent stem cell according to [1] or [2], which is negative for CD117, negative for CD146, negative for NG2, negative for CD34, negative for vWF, and negative for CD271.
[5] The pluripotent stem cell according to [1] or [2], which is negative for CD34, negative for CD117, negative for CD146, negative for CD271, negative for NG2, negative for vWF, negative for Sox10, negative for Snail, negative for Slug, negative for Tyrp1, and negative for Dct.
[6] The pluripotent stem cell according to any one of [1] to [5], which has low or no telomerase activity.
[7-1] The pluripotent stem cell according to any one of [1] to [6], which is capable of differentiating into the three germ layers.

The pluripotent stem cells of the present invention are capable of differentiating into the three germ layers through in vitro adherent culture. Specifically, the pluripotent stem cells can differentiate into cells representative of the three germ layers, skin, liver, nerve, muscle, bone, fat, and the like through in vitro induction culture. Also, the pluripotent stem cells are capable of differentiating into cells characteristic of the three germ layers when transplanted in vivo; the pluripotent stem cells are capable of surviving and differentiating into organs (e.g., skin, spinal cord, liver, and muscle) when transplanted to the damaged organs via intravenous injection into a living body.
[7-2] The pluripotent stem cells can act as tissue repairing cells. They integrate as functional cells into damaged tissue and differentiate into ectodermal-, endodermal-, and mesodermal-lineage cells according to the site of integration, and contribute to tissue reconstruction.
[8] The pluripotent stem cell according to any one of [1] to [7], which does not undergo tumorigenic proliferation.

The pluripotent stem cells of the present invention have a property such that they grow at a growth rate of about 1.3 days/cell division by suspension culture but stop the growth within about 10 days and also have a property such that when transplanted into the testis, they do not become tumorigenic for at least a half year.
[9] The pluripotent stem cell according to any one of [1] to [8], which has self-renewal capability.

The pluripotent stem cells of the present invention can be grown through adherent culture. The pluripotent stem cells of the present invention can also be grown through repetition of suspension culture and adherent culture.
[10] The pluripotent stem cell according to any one of [1] to [9], which is resistant to stress.
[11] The pluripotent stem cell according to any one of [1] to [10], which has high phagocytic ability.
[12] The pluripotent stem cell according to any one of [1] to [11], which is positive for at least one of the 22 following odorant receptors:
olfactory receptor, family 8, subfamily G, member 2 (OR8G2);
olfactory receptor, family 7, subfamily G, member 3 (OR7G3);
olfactory receptor, family 4, subfamily D, member 5 (OR4D5);

olfactory receptor, family 5, subfamily AP, member 2 (OR5AP2);
olfactory receptor, family 10, subfamily H, member 4 (OR10H4);
olfactory receptor, family 10, subfamily T, member 2 (OR10T2);
olfactory receptor, family 2, subfamily M, member 2 (OR2M2);
olfactory receptor, family 2, subfamily T, member 5 (OR2T5);
olfactory receptor, family 7, subfamily D, member 4 (OR7D4);
olfactory receptor, family 1, subfamily L, member 3 (OR1L3);
olfactory receptor, family 4, subfamily N, member 4 (OR4N4);
olfactory receptor, family 2, subfamily A, member 7 (OR2A7);
guanine nucleotide binding protein (G protein), alpha activating activity polypeptide, olfactory type (GNAL);
olfactory receptor, family 6, subfamily A, member 2 (OR6A2);
olfactory receptor, family 2, subfamily B, member 6 (OR2B6);
olfactory receptor, family 2, subfamily C, member 1 (OR2C1);
olfactory receptor, family 52, subfamily A, member 1 (OR52A1);
olfactory receptor, family 10, subfamily H, member 3 (OR10H3);
olfactory receptor, family 10, subfamily H, member 2 (OR10H2);
olfactory receptor, family 51, subfamily E, member 2 (OR51E2);
olfactory receptor, family 5, subfamily P, member 2 (OR5P2); and olfactory receptor, family 10, subfamily P, member 1 (OR10P1).
[13] The pluripotent stem cell according to any one of [1] to [12], which is positive for at least one of the 5 following chemokine receptors:
chemokine (C-C motif) receptor 5 (CCR5);
chemokine (C-X-C motif) receptor 4 (CXCR4);
chemokine (C-C motif) receptor 1 (CCR1);
Duffy blood group, chemokine receptor (DARC); and
chemokine (C-X-C motif) receptor 7 (CXCR7).
[14] The pluripotent stem cell according to any one of [1] to [13], which is derived from mesodermal tissue or mesenchymal tissue.
[15] A cell cluster or a cell fraction, which contains the pluripotent stem cell according to any one of [1] to [14].
[16] A method for isolating a pluripotent stem cell or a pluripotent cell fraction from body tissue, which uses at least one of the following properties (i) to (vi) as an index:
(i) being positive for SSEA-3;
(ii) being positive for CD105;
(iii) being negative for CD117 and negative for CD146;
(iv) being negative for CD117, negative for CD146, negative for NG2, negative for CD34, negative for vWF, and negative for CD271;
(v) being negative for CD34, negative for CD117, negative for CD146, negative for CD271, negative for NG2, negative for vWF, negative for Sox10, negative for Snail, negative for Slug, negative for Tyrp1, and negative for Dct; and
(vi) having low or no telomerase activity.

[17] A method for enrichment of a pluripotent stem cell or a pluripotent cell fraction, which comprises exposing body tissue-derived cells to cellular stress and then collecting surviving cells.
[18] The method for enrichment of a pluripotent stem cell or a pluripotent cell fraction according to [17], wherein cellular stress is selected from among protease treatment, culture under low-oxygen conditions, culture under low phosphate conditions, culture under serum starvation conditions, culture in a sugar starvation state, culture under exposure to radiation, culture under exposure to heat shock, culture in the presence of a toxic substance, culture in the presence of active oxygen, culture under mechanical stimulation, and culture under pressure treatment.
[19] The method for enrichment of a pluripotent stem cell or a pluripotent cell fraction according to [18], wherein the cellular stress is trypsin incubation.
[20] A pluripotent stem cell, which is a cell derived or induced from the pluripotent stem cell according to any one of [1] to [14].
Examples of the derived cell or the induced cell include cells induced by gene transfer or addition of a compound. Another example thereof is an iPS cell from the stem cell of the present invention.
[21] A differentiated cell, which is a cell derived or induced from the pluripotent stem cell according to any one of [1] to [14].
[22] A pharmaceutical composition, which comprises the pluripotent stem cell according to any one of [1] to [14] and [20].
[23] A pharmaceutical composition, which comprises the differentiated cell according to [21].
[24] A pharmaceutical composition, which comprises the differentiated cell according to [21].
[25] The pluripotent stem cell according to [1], which is derived from umbilical cord or fat tissue of a living body.
[26] A cell therapy composition for allo-transplantation comprising the pluripotent stem cell according to [1], in which the pulipotent stem cell does not express HLA class II antigen.
[27] A method for regenerate a tissue in a subject, which comprises administering the pluripotent stem cell according to [1], in which the pulipotent stem cell does not express HLA class II antigen.

The specification includes part or all of the contents as disclosed in the specifications and/or drawings of U.S. Provisional Application No. 61/213,788 and U.S. Provisional Application No. 61/290,159, which are priority documents of the present application.

BRIEF DESCRIPTION OF THE DRAWINGS

As shown in FIG. 1, SSEA-3-positive cells are directly separated and then cultured by suspension culture without exposure to long-term stress, so that M-clusters can be obtained. M-cluster generates ectodermal, endodermal and mesodermal cells on gelatin culture.
FIG. 3 shows factors, the ratio of the expression level thereof in a M-cluster to that in a naive cell fraction was high.
FIG. 4 shows factors, the ratio of the expression level thereof in a M-cluster to that in human ES cells was high.

FIGS. 7A, 7B, 7C, 7D, 7E, 7F and 7G show photos of various cells. FIG. 7A shows a single cell (Bar=10 μm) in a Muse-enriched cell fraction, FIG. 7B shows a human ES cell-derived embryoid body cell cluster (Bar=25 μm), FIG. 7C shows a M-cluster (Bar=25 μm) with a diameter of about 25 μm, FIG. 7D shows a human ES-derived cell cluster (on day 4) stained by alkaline phosphatase staining (Bar=25 μm), and FIGS. 7E-7G show immunologically stained images of Oct3/4(e), Sox2(f), and PAR4(g) in M-clusters.

FIGS. 8A, 8B, 8C, 8D, 8E and 8F show photos showing the characteristics of cell clusters formed from general adherent culture of H-fibroblasts and human MSCs (H-MSCs). FIGS. 8A and 8B show cell clusters (Bar=100 μm) spontaneously formed by general adherent culture for naive human MSCs. FIGS. 8C and 8D show the state of an H-fibroblast-1 fraction on day 0 (c) and day 7 (d) subjected to long-term trypsin incubation followed by MC culture (Bar=100 μm). An arrow head in FIG. 8D indicates a M-cluster. FIGS. 8E and 8F show M-clusters formed from an H-fibroblast-1 fraction on day 7 of MC culture (Bar=50 μm).

FIGS. 9A-9F show the results of immunostaining; that is, show the localization of Nanog (FIGS. 9A and 9D), Oct3/4 (FIG. 9B), SSEA-3 (FIG. 9C), PAR4 (FIG. 9E), and Sox2 (FIG. 9F) in M-clusters (FIGS. 9A, C, and 9E) formed from H-fibroblasts and M-clusters (FIGS. 9B, D, and 9F) formed from H-MSCs (Bar=50 μm).

FIGS. 10A-C show the results of alkaline phosphatase staining for human ES cells (FIG. 10A), M-clusters (FIG. 10B) from H-fibroblasts, and naive H-fibroblast-1 in adherent culture (FIG. 10C) (Bar=50 μm).

FIGS. 11A, 11B and 11C show electron micrographs showing the characteristics of cell clusters from H-fibroblasts and human MSCs (H-MSCs). FIGS. 11A-C show electron microscopic images of human ES cell embryoid bodies (FIG. 11A, on day 3 of MC culture), H-fibroblast-1-derived M-clusters (FIGS. 11B and 11C, on day 5 of MC culture) (Bar=5 μm).

FIG. 12 shows the outline of an experiment conducted for determination of the clonality and self-renewal of Muse cells.

FIGS. 15A, 15B and 15C show the differentiation of M-clusters. FIGS. 15A-15C show immunologically stained images showing the localization of α smooth muscle actin and neurofilaments (FIGS. 15A and 15B) and α-fetoprotein (FIG. 15C) in differentiated M-clusters from H-fiboroblast-1 (Bar=500 μm in FIG. 15A; Bar=50 μm in FIGS. 15B and 15C). Arrow heads in FIG. 15A indicate adhered M-cluster.

FIG. 17 shows a control intact testis, a testis obtained via administration of mouse ES cells (mES cells) (week 8), a testis obtained via administration of MEF (feeder cells) (week 8), a testis obtained via administration of a M-cluster (M-clusters) (month 6), and a testis obtained via administration of a Muse-enriched cell fraction (Muse) (month 6).

FIG. 21A shows M-clusters formed by performing MC culture (7 days) for mononuclear cell fractions isolated from human bone marrow (Bar=100 μm). FIG. 21B shows an alkaline phosphatase-stained image of M-cluster (Bar=50 μm).

FIGS. 28A, 28B and 28C show photos showing the differentiation of GFP-labeled SSEA-3 (+) Muse cell fractions in damaged tissue of severely immunodeficient mice (Nog mice). FIGS. 28 A and B show GFP (+) cells of a spinal cord damaged due to compression (4 weeks later), expressing neurofilaments (red) and human golgi complexes (white). FIG. 28 B shows an enlarged image of a part enclosed by a square in FIG. 28 A. FIG. 28 C shows GFP (+) target cells of a damaged liver (4 weeks later), expressing human albumin (red) and human golgi complexes (white).

FIGS. 31 A-D show the results of neural induction. FIG. 31A shows the thus formed neurospheres. Furthermore, as immunostaining data for neurospheres, FIG. 31B shows the expression of nestin, FIG. 31C shows the expression of Musashi, and FIG. 31D shows the expression of NuroD. FIG. 31E shows MAP-2 (+) cells obtained by further causing these spheres to differentiate into neural cells. FIGS. 31F-G show the results of osteocyte induction and specifically show the expression of osteocalcin (F) and alkalinephosphatase (G). FIGS. 31H and I show the results of adipocyte induction. FIG. 31H shows cells containing lipid droplets and FIG. 31I shows the result of oil red staining. FIG. 31J shows the result of hepatocyte induction; that is, α-fetoprotein (+) cells.

FIGS. 34A, 34B, 34C, 34D, 34E and 34F show the expression of NG2, CD34, vWF, CD117, CD146, and CD271, as analyzed by FACS. In naive human dermal fibroblasts, NG2 that is a pericyte marker and CD34 and vWF that are endothelial progenitor cell markers were found to be negative. They were also found to be negative in SSEA-3 (+) cells. Few naive human dermal fibroblasts were found to be positive for CD117 that is a melanoblast marker, CD146 that is a pericyte marker, and CD271 that is a NCSC marker (0.2%, 0.2%, and 0.8%, respectively), but were not thought to be Muse cells since they were SSEA-3 (−) cells.

FIGS. 36A, 36B, 36C, 36D, 36E and 36F show photos showing the formation of iPS cells prepared from Muse cells. FIG. 36A shows a state of human iPS cells induced from dermal fibroblast-derived Muse cells. FIGS. 36B-F show the expression of pluripotent cell markers ("b" shows the expression of Nonog, "c" shows the expression of Oct3/4, "d" shows the expression of Sox2, "e" shows the expression of SSEA-3, and "f" shows the expression of Tra-1-60).

FIGS. 41A, 41B, 41C and 41D show photos showing iPS cell colony (Muse cell-derived iPS cells) (FIGS. 41A and B) and non-iPS cell colony generated from SSEA-3 (−) cells (FIGS. 41C and D).

FIG. 42A shows the expression of α-fetoprotein (green) that is an endodermal marker and smooth muscle actin (red (blue indicates DNA)) that is a mesodermal marker. FIG. 42B shows the expression of neurofilament (green) that is an ectodermal marker.

FIG. 43 specifically shows the expression of markers for the 3 germ layers.

FIGS. 44A, 44B, 44C, 44D, 44E and 44F show photos showing tissue structures of teratomas formed from iPS cells induced from dermal fibroblast-derived Muse cells. FIG. 44 specifically shows differentiation of iPS cells into various types of tissue, as revealed by HE (Hematoxylin and eosin) staining. FIG. 44B shows cartilage, FIG. 44C shows muscle, FIG. 44D shows neural epithelium, FIG. 44E shows pigmented epithelium, and FIG. 44F shows columnar epithelium.

FIG. 46 shows the results of quantitative PCR for factors involved in the cell cycle of naive fibroblasts (Naive), M-clusters (Cluster), and iPS cells (iPS). Among columns denoted with "/Naive," open columns indicate that the ratio of Muse fractions or M-clusters to naive cells is less than 2 (2:1) and higher than ½ (1:2). Also, filled columns indicate that the same ratio is higher than 2 (2:1). Columns shaded with oblique lines indicate that the same ratio is lower than 1/2 (1:2). Among columns denoted with "/iPS," Symbol "*" indicates that the gene expression level in M-clusters is higher than that in iPS cells. Symbol "**" indicates that the gene expression level in iPS cells is higher than that in M-clusters.

FIG. 47 shows the results of quantitative PCR for factors involved in pluripotency and the undifferentiated cell state of naive fibroblasts (Naive), M-clusters (Cluster), and iPS cells (iPS). The meaning of each column is as defined in FIG. 46.

FIG. 48 shows the summary of a research report concerning the induction efficiency of iPS cell lines prepared in human and mouse models. FIG. 48 shows combinations of transcription factors inducing nuclear reprogramming.

FIG. 50 shows the sequence of primers used for RT-PCR and positive and negative control for each factor.

FIG. 53A shows the morphology of M-cluster obtained from commercially available human adipose-derived stem cell (HADSC) and FIG. 53B shows the morphology of M-cluster obtained from the established mesenchymal cell derived from human subcutaneous adipose tissue.

FIGS. 55A, 55B and 55C are photographs of immunostaining which shows that M-cluster formed from human adipose-derived stem cell (HADSC) differentiates into cells of three germ layers (tridermic cells). NF; neurofilament, ectodermal, CK7; cytokeratin7, endodermal, SMA; smooth muscle actin, mesodermal.

FIGS. 59A and 59B are photographs of mouse testis to which Muse cells were transplanted (4 months after transplantation). No sign of tumor formation was observed.

FIG. 62 shows the expression of SSEA-3 on mesenchymal cells obtained from human umbilical cord. 1: No stain, 2: Second antibody only, 3: SSEA-3 staining.

FIGS. 71A, 71B, 71C, 71D and 71E show the results of FACS analysis of cells obtained by the induction of differentiation from monocytes to monocyte-derived dendritic cell (MoDC) progenitor cells.

FIGS. 73A, 73B, 73C, 73D, 73E, 73F and 73G show the results of FACS analysis of cells obtained by the induction of differentiation from monocyte-derived dendritic cell (MoDC) progenitor cells to dendritic cells.

DETAILED DESCRIPTION OF THE PREFERRED EMBODIMENTS

Figure 1:
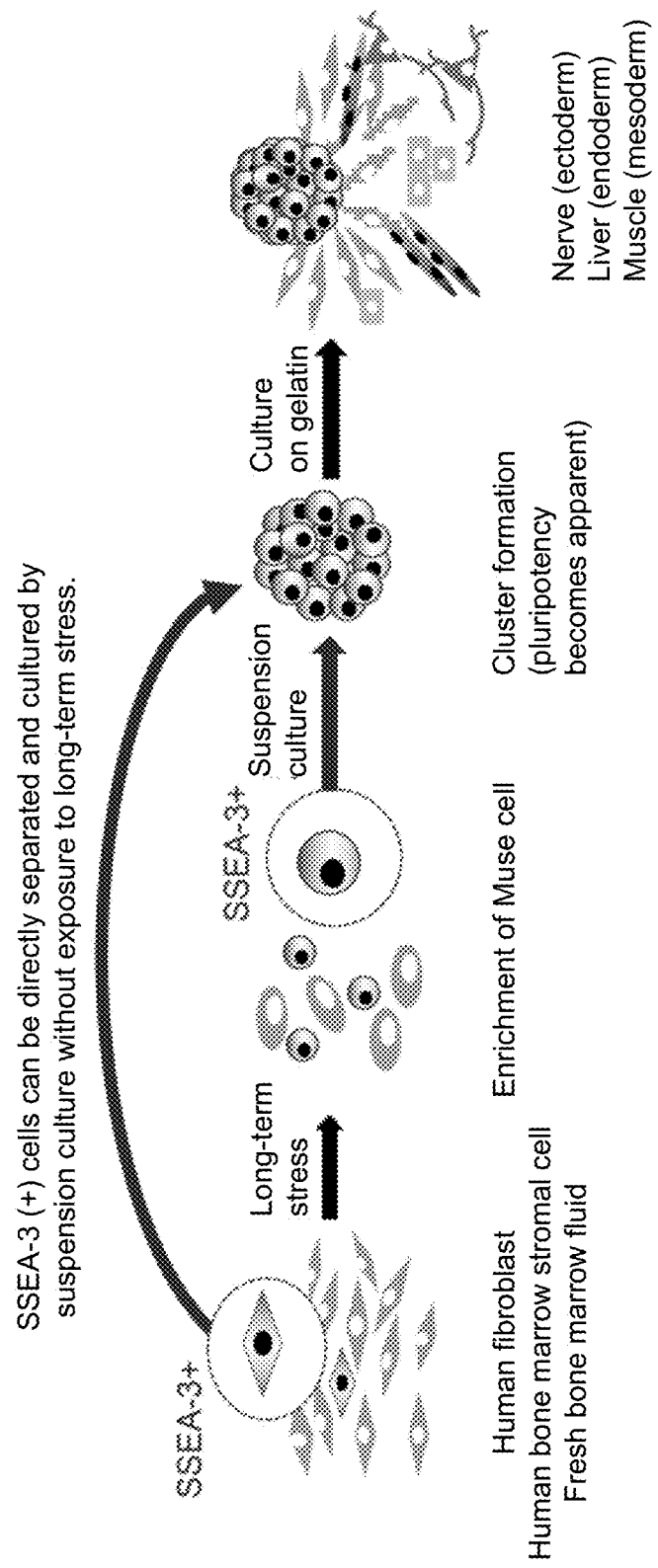
FIG. 1 shows the relationship among mesenchymal cell fractions, Muse cells, and M-clusters (Muse cell-derived embryoid body-like cell clusters).

The present invention will be described in detail as follows.

The present invention relates to pluripotent stem cells or pluripotent stem cell fractions that can be directly obtained from body tissue of a living body (in vivo), a method for isolating the pluripotent stem cells or the pluripotent stem cell fractions, and the body tissue-derived pluripotent stem cells or pluripotent stem cell fractions obtained by the method. The pluripotent stem cells of the present invention are referred to as Muse cells (multilineage-differentiating stress enduring cells).

In the present invention, the term "cell fraction" refers to a cell population containing at least a given amount of a cell to be isolated. For example, the term "pluripotent stem cell fraction" refers to a cell population containing a pluripotent stem cell in an amount corresponding to 1% or more thereof, 10% or more thereof, 30% or more thereof, 50% or more thereof, 70% or more thereof, 90% or more thereof, or 95% or more thereof. Examples thereof include cell clusters obtained via culture of pluripotent stem cells and cell populations obtained via enrichment of pluripotent stem cells. Also, the cell fraction may also be referred to as a substantially homogenous cell fraction.

The term "living body" refers to a living mammalian body, and it specifically refers to an animal body that undergoes development to some extent. In the present invention, examples of such living body do not include fertilized eggs or embryos at development stages before the blastula stage, but include embryos at development stages on and after the blastula stage, such as fetuses and blastulae. Examples of mammals include, but are not limited to, primates such as humans and monkeys, rodents such as mice, rats, rabbits, and guinea pigs, cats, dogs, sheep, pigs, cattle, horses, donkeys, goats, and ferrets. The pluripotent stem cells of the present invention are clearly distinguished from embryonic stem cells (ES cells) or embryonic germ stem cells (EG cells) in that they are from living body tissue.

The term "mesodermal tissue" refers to tissue of mesodermal origin that appears in the course of initial development of an animal. Examples of mesodermal tissue include tissue of the muscular system, connective tissue, tissue of the circulatory system, tissue of the excretory system, and tissue of the genital system. For example, the pluripotent stem cells of the present invention can be obtained from bone marrow aspirates or skin tissue such as dermal connective tissue.

The term "mesenchymal tissue" refers to tissue such as bone, cartilage, fat, blood, bone marrow, skeletal muscle, dermis, ligament, tendon, dental pulp and umbilical cord. For example, the pluripotent stem cells of the present invention can be obtained from the bone marrow or skin. Pluripotent cells derived from adipose tissue can be isolated from adipose-derived stem cells (ADSCs) or adipose-derived mesenchymal cells which are obtained from adipose tissue. Commercially available ADSCs can be used. Adipose-derived stem cells are mesenchymal stem cells included in fat tissue (adipose tissue). Adipose-derive stem cell fraction can be obtained from pannicular tissue or subcutaneous aspirate by the known method. For example, mesenchymal cells (ADSC) established from adipose tissue according to Estes B T., et al. Nat Protoc. 2010 Jul.: 5(7):1294-1311 can be used. For cell surface antigens, adipose-derived stem cells are CD13 positive, CD29 positive, CD44 positive, CD73 positive, CD90 positive, CD105 positive, CD166 positive, CD14 negative, CD31 negative and CD45 negative. Adipose-derived stem cells are commercially available. For example, human adipose-derived stem cells purchased from Lonza Group Ltd. Also, the pluripotent stem cells can be obtained from the umbilical cord. Umbilical cord is umbilical cord mesenchymal tissue of mammals. Umbilical cord is comprised of epidermis, vessel, blood, and mesenchymal tissue. Mesenchymal tissue is origin of mesenchymal cells from umbilical cord.

Both of Umbilical cord and fat tissue can be frozen for preservation before use.

The expression "cells can be directly obtained from tissue" means that cells can be isolated from tissue without any artificial induction operation such as introduction of a foreign gene or a foreign protein or treatment with a compound (e.g., administration of a compound). Such foreign gene may be, but is not limited to, a gene capable of reprogramming the nucleus of a somatic cell, for example. Examples of such foreign gene include Oct family genes such as an Oct3/4 gene, Klf family genes such as a Klf gene, Myc family genes such as a c-Myc gene, and Sox family genes such as a Sox2 gene. Also, examples of a foreign protein include proteins encoded by these genes and cytokines. Furthermore, examples of a compound include a low-molecular-weight compound capable of inducing the expression of the above gene that can reprogram the nucleus of a somatic cell, DMSO, a compound that can function as a reducing agent, and a DNA methylating agent. The pluripotent stem cells of the present invention are clearly distinguished from iPS cells (induced pluripotent stem cells) and ES cells in that the pluripotent stem cells of the present invention can be directly obtained from living bodies or tissue. In addition, in the present invention, cell culture, isolation of a cell or a cell fraction using a cell surface marker as an index, exposure of cells to cellular stress, and provision of a physical impact on cells are not included in examples of artificial induction operation. Also, the pluripotent cells of the present invention may also be characterized in that they can be obtained without requiring reprogramming or induction of dedifferentiation.

The pluripotent stem cells of the present invention are thought to be present in mesodermal tissue or mesenchymal tissue, or the like of a living body. In the present invention, cells or cell fractions existing in these types of tissue are isolated. The pluripotent stem cells of the present invention are present in the bone marrow, for example, so that they may be supplied from the bone marrow to each tissue of a living body via blood or the like. Hence, the pluripotent stem cells can be isolated from the bone marrow, each tissue of a living body, such as skin, and even blood.

The term "pluripotent stem cell(s)" refers to cells having pluripotency and having the following properties.
(1) The pluripotent stem cells express pluripotency markers such as Nanog, Oct3/4, SSEA-3, PAR-4, and Sox2.
(2) The pluripotent stem cells exhibit clonality by which they expand from a single cell and keep producing clones of themselves.
(3) The pluripotent stem cells exhibit self-renewal capability.
(4) The pluripotent stem cells can differentiate in vitro and in vivo into the three germ layers (endodermal cell lineage, mesodermal cell lineage, and ectodermal cell lineage).
(5) The pluripotent stem cells differentiate into the three germ layers when transplanted into the testis or subcutaneous tissue of a mouse.
(6) The pluripotent stem cells are found to be positive through alkaline phosphatase staining.

The pluripotent stem cells of the present invention are clearly distinguished from adult stem cells and tissue stem cells in that pluripotent stem cells of the present invention have pluripotency. Also, the pluripotent stem cells of the present invention are clearly distinguished from cell fractions such as bone marrow stromal cells (MSC) in that pluripotent stem cells of the present invention are isolated in the form of a single cell or a plurality of cells having pluripotency.

Moreover, the pluripotent stem cells of the present invention have the following properties.
(i) The growth rate is relatively gentle and the division cycle takes 1 day or more, such as 1.2-1.5 days. However, the pluripotent stem cells do not exert infinite proliferation in a manner similar to ES cells or iPS cells.
(ii) When transplanted into an immunodeficient mouse, the pluripotent stem cells differentiate into an endodermal cell lineage, a mesodermal cell lineage, and an ectodermal cell lineage. The pluripotent stem cells are characterized in that they do not become tumorigenic cells for a half year or longer, unlike ES cells or iPS cells, whereby teratomas are formed within a short time period such as 8 weeks.

(iii) The pluripotent stem cells form embryoid body-like cell clusters as a result of suspension culture.

(iv) The pluripotent stem cells form embryoid body-like cell clusters as a result of suspension culture and stop growth within about 10-14 days. Subsequently, when the clusters are transferred for adherent culture, they start to grow again.

(v) Asymmetric division is associated with growth.

(vi) The karyotypes of the cells are normal.

(vii) The pluripotent stem cells have no or low telomerase activity. The expression " . . . have no or low telomerase activity" refers to no or low telomerase activity being detected when such activity is detected using a TRAPEZE XL telomerase detection kit (Millipore), for example. The term "low telomerase activity" refers to a situation in which cells have telomerase activity to the same degree as that of human fibroblasts or have telomerase activity that is $1/5$ or less and preferably $1/10$ or less that of Hela cells.

(viii) Regarding methylation state, methylation levels in Nanog and Oct3/4 promoter regions are low in iPS cells induced from Muse cells.

(ix) The pluripotent stem cells exhibit high phagocytic ability.

(x) The pluripotent stem cells exhibit no tumorigenic proliferation. Here, the expression " . . . cells exhibit no tumorigenic proliferation" refers to a situation in which, when suspension culture is performed, the cells stop their growth at the time when their clusters reach a predetermined size and do not undergo infinite growth. Moreover, such expression refers to a situation in which, when such cells are transplanted into the testis of an immunodeficient mouse, no teratoma is formed. In addition, the above (i) to (iv) and the like also relate to the fact that the relevant cells (clusters) do not undergo tumorigenic proliferation.

Specifically, the cells of the present invention are the following pluripotent stem cells, for example:

(A) pluripotent stem cells that are obtained from mesodermal tissue, mesenchymal tissue, or the like of a living body and can be directly obtained without introduction of a chemical substance, a foreign gene, or a foreign protein into such cells;

(B) pluripotent stem cells having the property of (1) above, wherein mesodermal tissue or mesenchymal tissue of a living body is selected from the group consisting of bone marrow, skin, blood, umbilical cord, and fat;

(C) the pluripotent stem cells of (A) or (B) above that can be obtained without reprogramming or induction of dedifferentiation;

(D) the pluripotent stem cells of (A) or (B) above that do not become tumorigenic at least within half a year after being transplanted into the testis;

(E) the pluripotent stem cells of (A) or (B) above that do not undergo infinite growth, unlike ES cells and iPS cells; or (F) pluripotent stem cells from mesodermal tissue or mesenchymal tissue of a living body, which survive when treated with protease and thus are resistant to protease.

Moreover, the pluripotent stem cells of the present invention can be enriched by placing cellular stress on the cells of mesodermal tissue or mesenchymal tissue of a living body and then collecting surviving cells. Here, the term "cellular stress" refers to external stress. Specifically, cells are exposed to such stress via protease treatment, culture under low-oxygen conditions, culture under low phosphate conditions, culture under serum starvation conditions, culture in a sugar starvation state, culture under exposure to radiation, culture under exposure to heat shock, culture in the presence of a toxic substance, culture in the presence of active oxygen, culture under mechanical stimulation, culture under pressure treatment, or the like. Of these examples, protease treatment, and specifically, culture in the presence of protease, is preferred. Protease is not limited. Serine protease such as trypsin and chymotrypsin, aspartic protease such as pepsin, cysteine protease such as papain and chymopapain, metalloprotease such as thermolysin, glutamic protease, N-terminal threonine protease, and the like can be used. The concentration of protease to be added for culture is not limited. In general, concentrations to be employed for removal of adherent cells that are cultured in petri dishes or the like may be employed herein. The pluripotent stem cells of the present invention can be said to be stem cells having resistance to the above-mentioned external stresses, such as cells having resistance to trypsin.

Examples of mesodermal tissue and mesenchymal tissue of a living body include, but are not limited to, bone-marrow mononuclear cells, fibroblast fractions such as skin cells, pulp tissue, eyeball tissue, and hair root tissue. As cells, both cultured cells and cells collected from tissue can be used. Among these cells, bone marrow cells and skin cells are desired. Examples of such cells include a human bone marrow stromal cell (MSC) fraction and a human dermal fibroblast fraction. A bone marrow stromal cell (MSC) fraction can be obtained by culturing a bone marrow aspirate for 2 to 3 weeks.

Most cells of tissue subjected to the various above stresses will die. Surviving cells include the pluripotent stem cells of the present invention. After stress is placed on cells, dead cells should be removed. However, when protease is used, these dead cells are lysed via the effects of protease.

Also, after stress is placed on cells, a physical impact is provided to the cells to make dead or dying cells become easily disrupted, and then those cells may be removed. A physical impact can be provided by rigorous pipetting, rigorous stirring, vortexing, or the like.

Cellular stress is placed on cells, a physical impact is provided if necessary, and then the resulting cell populations are subjected to centrifugation. The resulting surviving cells are obtained and collected as pellets, so that the pluripotent stem cells of the present invention can be isolated. Also, from the thus obtained cells, the pluripotent stem cells or pluripotent cell fractions of the present invention can be isolated using the following surface markers as indices.

The pluripotent stem cells or pluripotent cell fractions of the present invention can also be enriched by culturing mesodermal tissue, mesenchymal tissue, or the like (in vivo) of a body subjected to stress such as trauma or a burn and then collecting cells that have migrated. Cells of damaged tissue are exposed to stress. Hence, in the present invention, the expression "culture of mesodermal tissue or mesenchymal tissue (in vivo) of a damaged body" also refers to placing cellular stress on cells of mesodermal tissue, mesenchymal tissue, or the like of a living body.

As an example, a method for treating such cells with trypsin is as described below. The concentration of trypsin at this time is not limited. For example, in general culture of adherent cells, the concentrations of trypsin may be concentrations that are employed for removal of adherent cells adhering to a culture vessel, ranging from 0.1% to 1% and preferably ranging from 0.1% to 0.5%, for example. For example, cells can be exposed to external stress by incubating cells (100,000-500,000 cells) from mesodermal tissue, mesenchymal tissue, or the like of a living body in 5 ml of a trypsin solution with the above concentration. The time for trypsin incubation ranges from about 5 to 24 hours and preferably ranges from about 5 to 20 hours. In the present invention, 8 or more hours of trypsin incubation, such as 8 hours or 16 hours of treatment, is long-term trypsin incubation.

After trypsin incubation, a physical impact is desirably provided by pipetting, stirring, vortexing, or the like, as described above. This is performed to remove dead cells or dying cells.

When suspension culture is performed after trypsin incubation, incubation is desirably performed in gel such as methylcellulose gel, in order to prevent cell-to-cell aggregation. Also, a cell culture vessel is desirably coated in advance with poly(2-hydroxyethyl methacrylate) or the like in order to prevent adhesion of cells to the culture vessel and maintain the state of suspension.

When cells exposed to external stress, collected by centrifugation, and then cultured, cells form cell clusters. The size of such a cell cluster ranges in diameter from about 25 µm to 150 µm. The pluripotent stem cells (Muse cells) of the present invention are included in an enriched state within a cell fraction that has survived after exposure to external stress. Such cell fraction is referred to as Muse-enriched cell fractions (Muse enriched populations). The percentage of Muse cells in such a Muse-enriched cell fraction differs depending on method of stress treatment.

The fact that the pluripotent stem cells or the pluripotent stem cell fractions of the present invention survive after exposure to stress suggests that the pluripotent stem cells or the pluripotent stem cell fractions of the present invention are resistant to such stress.

Regarding the medium to be used for culturing cells from mesodermal tissue, mesenchymal tissue, or the like of a living body and culture conditions, any medium and culture conditions generally used for culturing animal cells may be employed. Also, a known medium for culturing stem cells may be used. A medium may be appropriately supplemented with serum such as fetal calf serum, antibiotics such as penicillin and streptomycin, and various bioactive substances.

Furthermore, the present invention also encompasses pluripotent stem cells which are derived cells or induced cells of the pluripotent stem cells of the present invention that can be directly obtained from the mesodermal tissue, mesenchymal tissue, or the like of a living body. The term "derived cells or induced cells" refers to cells or cell fractions obtained by culturing the pluripotent stem cells or cells obtained by subjecting the pluripotent stem cells to an artificial induction operation such as introduction of a foreign gene. Progeny cells are also included herein. In addition, it is said that iPS cells that had been reported at the time of the present invention are induced from pluripotent stem cells as a result of reprogramming (e.g., introduction of foreign genes into somatic cells, such as dermal fibroblasts). Cells obtained by subjecting cells of the present invention (that can be directly obtained from the tissue of the present invention and already have properties as pluripotent stem cells) to an artificial induction operation such as introduction of a foreign gene are distinguished from iPS cells.

Embryoid body-like (EB body-like) cell clusters are obtained through suspension culture of the pluripotent stem cells of the present invention. The present invention also encompasses such embryoid body-like cell clusters and cells contained in such embryoid body-like cell clusters. Embryoid bodies are formed as cell clusters through suspension culture of the pluripotent stem cells such as ES cells. At this time, in the present invention, such an embryoid body-like cell clusters obtained by culturing the pluripotent stem cells of the present invention is also referred to as a M-cluster (Muse cell-derived embryoid body-like cell cluster). Examples of a method for suspension culture for the formation of embryoid body-like cell clusters include culture using medium containing a water soluble polymer such as methylcellulose (Nakahata, T. et al., Blood 60, 352-361 (1982)) and hanging drop culture (Keller, J. Physiol. (Lond) 168: 131-139, 1998). The present invention also encompasses embryoid body-like cell clusters obtained via self-renewal from the embryoid body-like cell clusters, cells contained in such embryoid body-like cell clusters, and pluripotent stem cells. Here, the term "self-renewal" refers to a situation in which cells contained in embryoid body-like cell clusters are cultured so as to cause the formation of embryoid body-like cell clusters again. Self-renewal may be performed by repeating a cycle once to several instances. Also, the present invention also encompasses cells and tissue, which differentiate from either the above embryoid body-like cell clusters or cells contained in such embryoid body-like cell clusters.

FIG. 1 shows the relationship among mesenchymal cell (human fibroblast, human bone marrow stromal cell (MSC), and fresh bone marrow fluid) fractions, Muse cells, and M-clusters. When stress stimulation (e.g., long-term trypsin incubation (LTT)) is imposed upon mesenchymal cell-like cell clusters, Muse cells are enriched, and then cell fractions containing many Muse cells (referred to as a Muse-enriched cell fraction) are obtained. Through suspension culture of Muse cells in the cell fraction, an embryoid body-like cell cluster (M-cluster) is obtained. When embryoid body-like cell clusters are cultured in a culture dish coated with gelatin, cells differentiate into cells of the 3 germ layers. Also, as shown in FIG. 1, SSEA-3 (+) cells are directly separated and then suspension culture is performed without exposing cells to long-term stress, so that M-clusters can be obtained.

Figure 2:
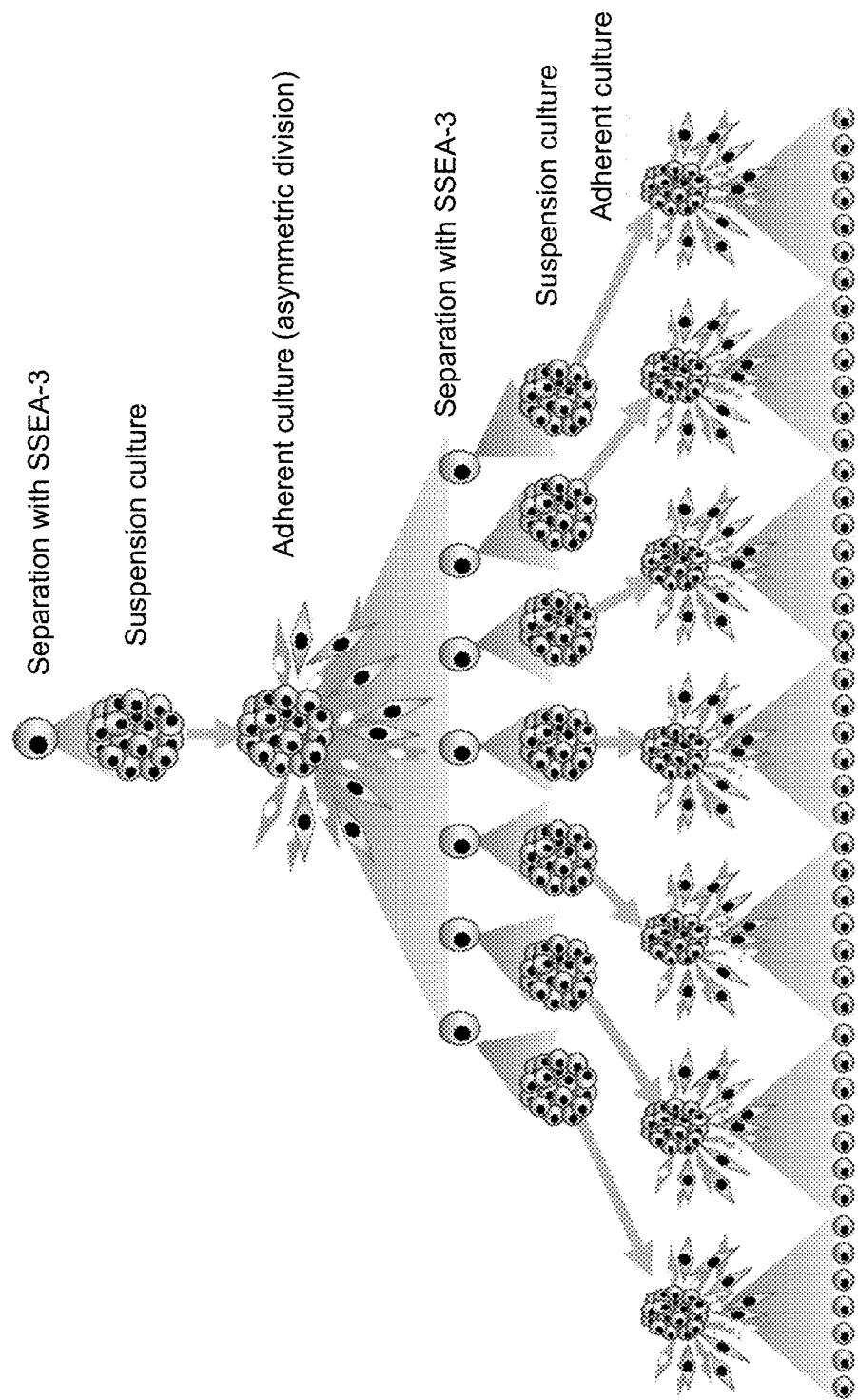
FIG. 2 shows a method for causing the growth of Muse cells in large amounts.

When the growth of Muse cells is stopped once via suspension culture, Muse cells initiate growth when transferred for adherent culture. Through repetition of separation using suspension culture-adherent culture-SSEA-3 expression as an index, Muse cells can be grown in large amounts (FIG. 2).

Furthermore, the pluripotent stem cells or pluripotent cell fractions of the present invention can also be directly isolated from body tissue without exposure to cellular stress. Specifically, the pluripotent stem cells or the pluripotent stem cell fractions of the present invention can be isolated from mesodermal tissue, mesenchymal tissue, or the like of a living body by the following method without an induction operation such as introduction of a foreign gene.

Examples of body tissue include, but are not limited to, mesodermal tissue and mesenchymal tissue of a living body such as bone marrow, skin, and umbilical cord tissue. When bone marrow is used, a mononuclear cell fraction of the bone marrow can be used. Isolation can be performed using a cell surface marker that is expressed richly on the surface of Muse cells. For example, isolation can be performed using SSEA-3 expression as an index. The pluripotent stem cells of the present invention may also be referred to as SSEA-3 (+) Muse cells. Moreover, Muse cells express CD105, which is a mesenchymal marker. Muse cells are positive for SSEA-3, and positive for CD105. Therefore, Muse cells can be isolated using the expression of both SSEA-3 and CD105 as an index. With the use of these cell surface markers, the pluripotent stem cells of the present invention can be isolated in the form of single cells. The thus isolated single cells can be grown by culture. In addition, the present invention encompasses pluripotent stem cells that can be isolated from body tissue of a mammal other than a human using a marker SSEA-3 or markers corresponding to SSEA-3. For example, 40 to 70% of cells isolated from HADSC using SSEA-3 as a maker are Muse cells which can form M-cluster.

Meanwhile, Muse cells are negative for NG2, CD34, vWF (von Willebrand factor), c-kit (CD117), CD146, and CD271 (NGFR). Moreover, Muse cells are negative for Sox10, Snail, Slug, Tyrp1, and Dct.

Whether or not cells are negative for surface antigens such as NG2, CD34, vWF, CD117, CD146, and CD271 or whether or not the expression thereof is weak can be determined by microscopically observing whether or not cells are stained with antibodies (against these antigens) labeled with a chromogenic enzyme, a fluorescent compound, or the like. For example, cells are immunostained with these antibodies, so that the presence or the absence of a surface antigen can be determined. The presence or the absence of the same can also be determined using antibody-conjugated magnetic beads. Also, the presence or the absence of a surface antigen can be determined using FACS or a flowcyte meter. As a flowcyte meter, FACSAria (Becton Dickinson), FACS vantage (Becton Dickinson), FACS Calibur (Becton Dickinson), MACS (magnetic cell sorting) or the like can be used, for example.

Regarding transcription factors such as Sox10, Snail, Slug, Tyrp1, and Dct, the expression thereof can also be examined by a technique such as RT-PCR.

The expression " . . . are negative for these surface antigens" refers to that a situation in which, when FACS analysis is conducted as described above, cells are not sorted as positive cells or when expression is examined by RT-PCR, no expression thereof is confirmed. Even if such surface antigens are expressed to a degree such that they are undetectable by such techniques, cells are designated as negative in the present invention. Also, at the same time, measurement is performed with cells such as hematopoietic stem cells known to be positive for the above markers. When almost no expression is detected or the expression level is significantly lower compared with such positive cells, cells may be designated as negative.

Cells of the present invention can be isolated based on the properties of the aforementioned cell surface antigens.

As described above, Muse cells can be isolated using "being positive for SSEA-3" as an index. Moreover, Muse cells can be isolated using the expression of CD105 as an index. Muse cells can be further isolated using non-expression of at least 1, such as 2, 3, 4, 5, 6, 7, 8, 9, 10, or 11, markers selected from the group consisting of NG2, CD34, vWF (von Willebrand factor), c-kit (CD117), CD146, CD271 (NGFR), Sox10, Snail, Slug, Tyrp1, and Dct, as an index. For example, isolation is possible using non-expression of CD117 and CD146. Furthermore, isolation can be performed using non-expression of CD117, CD146, NG2, CD34, vWF, and CD271 as an index. Furthermore, isolation can be performed using non-expression of the above 11 markers as an index.

When isolation is performed using a surface marker(s), 1 or a plurality of pluripotent stem cells of the present invention can be directly isolated from mesodermal tissue, mesenchymal tissue, or the like of a living body without culture or the like. Also, the pluripotent stem cells of the present invention can be identified and isolated by visually observing the cell morphology using a microscope or the like.

After provision of a cellular stress to mesodermal tissue, mesenchymal tissue, or the like of a living body, isolation may also be performed from a surviving cell group using a surface marker.

Also, the pluripotent stem cells or the pluripotent cell fractions of the present invention can be characterized by high-level expression of another specific factor, in addition to the use of the above markers.

Muse cells that are the pluripotent stem cells of the present invention can be obtained from naive bone marrow stromal cell (MSC) fractions or dermal fibroblast fractions. Muse cells are further cultured, so that Muse cell-derived embryoid body (EB)-like cell clusters (M-clusters) are obtained. Through comparison and examination of factors expressed in Muse cells, naive cells, Muse-derived embryoid body-like cell clusters, and human ES cells, a factor expressed at high levels in Muse cells can be detected. Examples of such factors include gene transcription products, proteins, lipids, and saccharides.

FIG. 3 shows factors for which the ratio of the expression level in M-clusters to the same in naive cells is high. In particular, the ratio is high for the following 18 factors.
(i) SSEA-3
(ii) v-fos FBJ murine osteosarcoma viral oncogene homolog
(iii) solute carrier family 16, member 6 (monocarboxylic acid transporter 7) (iv) tyrosinase-related protein 1
(v) Calcium channel, voltage-dependent, P/Q type, alpha 1A subunit
(vi) chromosome 16 open reading frame 81
(vii) chitinase 3-like 1 (cartilage glycoprotein-39)
(viii) protease, serine, 35
(ix) kynureninase (L-kynurenine hydrolase)
(x) solute carrier family 16, member 6 (monocarboxylic acid transporter 7)
(xi) apolipoprotein E
(xii) synaptotagmin-like 5
(xiii) chitinase 3-like 1 (cartilage glycoprotein-39)
(xiv) ATP-binding cassette, sub-family A (ABC1), member 13
(xv) angiopoietin-like 4
(xvi) prostaglandin-endoperoxide synthase 2 (prostaglandin G/H synthase and cyclooxygenase)
(xvii) stanniocalcin 1
(xviii) coiled-coil domain containing 102B The pluripotent stem cells or the pluripotent stem cell fractions of the present invention are characterized in that at least 2, 3, 4, 5, 6, 7, 8, 9, 10, 11, 12, 13, 14, 15, 16, 17, or 18 factors above are expressed at high levels. Hence, the pluripotent stem cells or the pluripotent stem cell fractions can be isolated using high-level expression of at least 2 factors as an index.

FIG. 4 shows factors for which the ratio of the expression level in M-clusters to the same in human ES cells is high. In particular, the ratio is high in the following 20 factors.
(a) matrix metallopeptidase 1 (interstitial collagenase)
(b) epiregulin
(c) chitinase 3-like 1 (cartilage glycoprotein-39)
(d) Transcribed locus
(e) chitinase 3-like 1 (cartilage glycoprotein-39)
(f) serglycin
(g) MRNA full length insert cDNA clone EUROIMAGE 1913076
(h) Ras and Rab interactor 2
(i) lumican
(j) CLCA family member 2, chloride channel regulator (k) interleukin 8
(l) Similar to LOC166075
(m) dermatopontin
(n) EGF, latrophilin and seven transmembrane domain containing 1
(o) insulin-like growth factor binding protein 1
(p) solute carrier family 16, member 4 (monocarboxylic acid transporter 5)
(q) serglycin
(r) gremlin 2, cysteine knot superfamily, homolog (*Xenopus laevis*)
(s) insulin-like growth factor binding protein 5
(t) sulfide quinone reductase-like (yeast)

The pluripotent stem cells or the pluripotent stem cell fractions of the present invention are characterized in that at least 2, 3, 4, 5, 6, 7, 8, 9, 10, 11, 12, 13, 14, 15, 16, 17, 18, 19, or 20 factors above are expressed at high levels. Hence, the pluripotent stem cells or the pluripotent stem cell fractions can be isolated using high-level expression of at least 2 factors as an index.

Furthermore, in the pluripotent stem cells or the pluripotent stem cell fractions of the present invention, at least 2 of the above factors (i)-(xviii) and at least 2 of the above factors (a)-(t) may be simultaneously expressed at high levels. Hence, the pluripotent stem cells or the pluripotent stem cell fractions can be isolated using high-level expression of these genes as an index.

Furthermore, the pluripotent stem cells or the pluripotent stem cell fractions of the present invention are characterized in that: factors of an odorant receptor (olfactory receptor) group and factors of a chemokine receptor group, other than pluripotency markers, are expressed; that is, they are positive for specific odorant receptors or chemokine receptors.

Examples of odorant receptors that are expressed in the pluripotent stem cells or the pluripotent stem cell fractions of the present invention include the following 22 receptors.
olfactory receptor, family 8, subfamily G, member 2 (OR8G2);
olfactory receptor, family 7, subfamily G, member 3 (OR7G3);
olfactory receptor, family 4, subfamily D, member 5 (OR4D5);
olfactory receptor, family 5, subfamily AP, member 2 (OR5AP2);
olfactory receptor, family 10, subfamily H, member 4 (OR10H4);
olfactory receptor, family 10, subfamily T, member 2 (OR10T2);
olfactory receptor, family 2, subfamily M, member 2 (OR2M2);
olfactory receptor, family 2, subfamily T, member 5 (OR2T5);
olfactory receptor, family 7, subfamily D, member 4 (OR7D4);
olfactory receptor, family 1, subfamily L, member 3 (OR1L3);
olfactory receptor, family 4, subfamily N, member 4 (OR4N4);
olfactory receptor, family 2, subfamily A, member 7 (OR2A7);
guanine nucleotide binding protein (G protein), alpha activating activity polypeptide, olfactory type (GNAL);
olfactory receptor, family 6, subfamily A, member 2 (OR6A2);
olfactory receptor, family 2, subfamily B, member 6 (OR2B6);
olfactory receptor, family 2, subfamily C, member 1 (OR2C1);
olfactory receptor, family 52, subfamily A, member 1 (OR52A1);
olfactory receptor, family 10, subfamily H, member 3 (OR10H3);
olfactory receptor, family 10, subfamily H, member 2 (OR10H2);
olfactory receptor, family 51, subfamily E, member 2 (OR51E2);
olfactory receptor, family 5, subfamily P, member 2 (OR5P2); and
olfactory receptor, family 10, subfamily P, member 1 (OR10P1)

Examples of a chemokine receptor that is expressed in the pluripotent stem cells or pluripotent stem cell fractions of the present invention include the 5 following receptors.
chemokine (C-C motif) receptor 5 (CCR5);
chemokine (C-X-C motif) receptor 4 (CXCR4);
chemokine (C-C motif) receptor 1 (CCR1);
Duffy blood group, chemokine receptor (DARC); and
chemokine (C-X-C motif) receptor 7 (CXCR7).

The pluripotent stem cells or the pluripotent stem cell fractions of the present invention express at least one of the above olfactory receptors or express at least one of the above chemokine receptors.

Because of the effects of these odorant receptors or chemokine receptors and migratory factors that bind to the receptors, the pluripotent stem cells of the present invention migrate to damaged tissue and then survive and differentiate at the tissue. For example, when the liver, skin, spinal cord, or muscle is damaged, a specific migratory factor and an odorant receptor expressed on the cell surfaces function to cause the pluripotent stem cells to migrate to the relevant tissue, survive at the tissue, and then differentiate into liver (endoderm), skin (ectoderm), spinal cord (ectoderm), or muscle (mesoderm) cells, so that the tissue can be regenerated.

In a Muse-enriched cell fraction richly containing Muse cells that are the pluripotent stem cells of the present invention, Rex1, Sox2, KLF-4, c-Myc, DPPA2, ERAS, GRB7, SPAG9, TDGF1, and the like are upregulated. In a cell cluster of Muse cells, DAZL, DDX4, DPPA4, Stella, Hoxb1, PRDM1, SPRY2, and the like are upregulated.

Also, in pluripotent stem cells or the pluripotent stem cell fractions of the present invention, the expression of CD34 and CD117 hematopoietic stem cell markers is never observed or is observed at an extremely low level.

The present invention encompasses not only Muse cells, but also a cell fraction resulting from enrichment of Muse cells, a cell fraction resulting from growth of Muse cells, and a cell fraction resulting from differentiation of Muse cells. The present invention further encompasses a research kit, a cell chip, and a therapeutic device containing Muse cells or cells derived from Muse cells.

The pluripotent stem cells of the present invention have pluripotency and thus are able to differentiate into all types of tissue. The pluripotent stem cells or the pluripotent cell fractions can be used for regeneration medicine and the like. For example, such cells and cell fractions can be used for regeneration of various types of tissue, various organs, and the like. Specific examples thereof include skin, cerebrospinal cord, liver, and muscle. The pluripotent stem cells or the pluripotent stem cell fractions of the present invention are administered directly to or to an area in the vicinity of injured or damaged tissue, organs, and the like, so that the pluripotent stem cells enter the tissue or organ and differentiate into cells unique to the relevant tissue or organ. In this manner, the pluripotent stem cells can contribute to the regeneration or reconstruction of tissue and organs. Also, the systemic administration of the pluripotent stem cells or pluripotent stem cell fractions is possible by intravenous administration or the like. In this case, the pluripotent stem cells are directed by homing or the like to a damaged tissue or organ, reach and enter the tissue or organ, and then differentiate into cells of the tissue or organ, so as to be able to contribute to tissue or organ regeneration and reconstruction.

Administration can be performed via parenteral administration such as subcutaneous injection, intravenous injection, intramuscular injection, and intraperitoneal injection, oral administration, or intrauterine injection into an embryo, for example. Also, local administration or systemic administration may be performed herein. Local administration can be performed using a catheter, for example. The dose can be appropriately determined depending on an organ to be regenerated, a tissue type, or a size.

Examples of an organ to be regenerated include, but are not limited to, bone marrow, spinal cord, blood, spleen, liver, lungs, bowel, eyes, brain, immune system, circulatory system, bone, connective tissue, muscle, heart, blood vessel, pancreas, central nervous system, peripheral nervous system, kidney, bladder, skin, epithelial appendages, breast-mammary gland, adipose tissue, and mucous membranes of mouth, esophagus, vagina, and anus, for example. Also, examples of diseases to be treated therein include, cancer, cardiovascular disease, metabolic disease, hepatic disease, diabetes mellitus, hepatitis, haemophilia, blood system disease, degenerative or traumatic neurologic disorder such as spinal cord injury, autoimmune disease, genetic defects, connective tissue disease, anemia, infectious disease, graft rejection, ischaemia, inflammation, and damage to skin or muscle.

Cells may be administered with a pharmaceutically acceptable base material. Such base material may be made of a substance with high bio-compatibility, such as collagen or a biodegradable substance. They may be in the form of particles, plates, tubes, vessels, or the like. Cells may be administered after binding thereof to a base material or after causing a base material to contain cells therein.

Also, in vitro differentiation induction is performed for pluripotent stem cells of the present invention, tissue is constructed using cells that have further differentiated, and then the differentiated cells or tissue may be transplanted. Since the pluripotent stem cells of the present invention do not undergo tumorigenic transformation, a probability of tumor formation of the cells is low and can be said to be safe, even when the undifferentiated pluripotent stem cells of the present invention are contained in the above transplanted differentiated cells or tissue. To prevent rejection of transplanted cells or tissue by a recipient in such regeneration medicine, it is desired that mesodermal tissue, mesenchymal tissue, or the like is collected from a patient to be subjected to regeneration medicine, and then pluripotent stem cells or pluripotent cell fractions of the present invention are isolated from the relevant tissue for use. Furthermore, the pluripotent stem cells or the pluripotent stem cell fractions of the present invention can be used for treatment of diseases due to tissue degeneration or dysfunction. In this case, for example, the pluripotent stem cells or the pluripotent stem cell fractions of the present invention are enriched ex vivo, grown, or caused to differentiate and then returned into the body. For example, the pluripotent stem cells are caused to differentiate into specific tissue cells and then the cells are transplanted into tissue to be treated. Also, in situ cell therapy can be performed by transplantation of such cells. In this case, examples of target cells include hepatic cells, neural cells such as neuronal cells or glial cells, skin cells, and muscle cells such as skeletal muscle cells. The pluripotent stem cells of the present invention are caused to differentiate into these cells, the differentiated cells are transplanted, and then treatment can be performed in situ. Through such treatment, Parkinson's disease, brain infarction, spinal cord injury, myodystrophy, and the like can be treated, for example. Since the pluripotent stem cells of the present invention do not undergo tumorigenic transformation, they unlikely become tumors and safe even if used for such treatment.

Also, the pluripotent stem cells of the present invention are caused to differentiate to form blood or blood components, so that blood or blood components can be formed ex vivo or in vitro. Examples of such blood components include erythrocytes, leukocytes, and blood platelets. The thus formed blood or blood components can be used for autologous transfusion or cross transfusion.

As described above, when the pluripotent stem cells or the pluripotent stem cell fractions of the present invention are used for treatment, their differentiation may be caused ex vivo, in vivo, or in vitro. The pluripotent stem cells of the present invention differentiate into osteoblasts, chondrocytes, adipocyte, fibroblasts, bone-marrow stroma, skeletal muscle, smooth muscle, myocardium, eyes, endothelium, epithelium, liver, pancreas, hematopoietic system, glia, neuronal cells, or oligodendroglial cell, for example. Differentiation of the pluripotent stem cells of the present invention can be achieved by culturing them in the presence of a differentiation factor. Examples of a differentiation factor include a basic fibroblast growth factor (bFGF), a vascular endothelium growth factor (VEGF), a dimethyl sulfoxide (DMSO), and isoproterenol; or a fibroblast growth factor 4 (FGF4) and a hepatocyte growth factor (HGF). The present invention also encompasses cells that have differentiated from the pluripotent stem cells of the present invention.

When the pluripotent stem cells of the present invention are used for treatment, a gene encoding a protein antitumor substance, a bioactive substance, or the like may be introduced. Therefore, it can be said that the pluripotent stem cells of the present invention have a function for the delivery of a therapeutic agent. Examples of such substance include antiangiogenic agents.

The present invention encompasses materials for cell transplantation therapy or compositions for cell transplantation therapy, or materials for regeneration medicine or compositions for regeneration medicine, which contain Muse cells, embryoid body-like cell clusters formed of Muse cells, and cells or tissue/organs obtained via differentiation from Muse cells or the above embryoid body-like cell clusters. Such a composition contains a pharmaceutically acceptable buffer, diluent, or the like in addition to Muse cells, an embryoid body-like cell cluster formed of Muse cells, or cells or tissue and/or organ obtained through differentiation from Muse cells or the above embryoid body-like cell cluster.

Moreover, cells are collected from a patient, Muse cells are isolated, and then the Muse cells can be used for various diagnoses. For example, a patient's genes are collected from Muse cells and then the gene information is obtained, so that precise diagnosis reflecting the information becomes possible. For example, cells of each tissue and/or organ having the same characteristics (e.g., genetic background) as those of a subject can be obtained by causing differentiation of patient's cell-derived Muse cells. Hence, regarding disease diagnosis, elucidation of pathological conditions, diagnosis for the effects or adverse reactions of drugs, or the like, appropriate diagnosis can be made according to the characteristics of each subject. Specifically, Muse cells, embryoid body-like cell clusters formed of Muse cells, and cells or tissue and/or organs obtained through differentiation of Muse cells or the above embryoid body-like cell clusters can be used as diagnostic materials. For example, the present invention encompasses a method for diagnosing the disease or the like of a subject using Muse cells isolated from the subject or using tissue or an organ (obtained via differentiation from the Muse cells) having the same genetic background as that of the subject.

Also, somatic cells can be obtained in large amounts via differentiation of Muse cells. Hence, basic research such as elucidation of a disease mechanism, development of a therapeutic agent, screening for the effects of a drug or toxicity, drug evaluation, and the like can be performed. Specifically, Muse cells, embryoid body-like cell clusters formed of Muse cells, and cells or tissue and/or organs obtained through differentiation of Muse cells or the above embryoid body-like cell clusters can be used as materials for drug evaluation or drug screening. For example, the present invention encompasses a method for screening for a drug or evaluating a drug, comprising causing differentiation and/or growth of Muse cells, obtaining somatic cells, administering a candidate drug to the somatic cells, and then examining the response of somatic cells.

Also, a Muse cell bank is constructed by constructing a library of various (e.g., various types of HLA) Muse cells, so that a system capable of providing Muse cells to Muse cell application sites according to need can be realized. For example, in addition to the above listed purposes, provision of cells with no (or little) rejections to urgently required cell transplantation therapy can be performed. Specifically, the present invention encompasses a method for constructing a Muse cell library; that is, a Muse cell bank, having different genetic properties, comprising isolating and collecting Muse cells having various genetic properties. Also, a library or a bank can also be constructed using not only Muse cells, but also an embryoid body-like cell cluster formed from Muse cells, and cells or tissue and/or organ obtained through differentiation from Muse cells or the above embryoid body-like cell clusters. In the present invention, libraries or banks that are constructed by obtaining embryoid body-like cell clusters formed of these Muse cells, and cells or tissue and/or organs obtained through differentiation of Muse cells or the above embryoid body-like cell clusters are also referred to as cell libraries or cell banks. The present invention encompasses the thus constructed cell libraries or cell banks. Such cell libraries or cell banks comprise vessels such as a plurality of tubes containing cells and the like having different genetic characteristics. Such cells may also be frozen. For example, when tissue or an organ is transplanted into a subject or regeneration thereof is required, cells appropriate in terms of genetic background or the like of the subject are selected from the above cell library or cell bank. Thus, transplantation or regeneration therapy can be performed using the cells.

The present invention encompasses a therapeutic method, comprising administering, for treatment of a disease, a therapeutically effective dose of the pluripotent stem cells, a cell fraction thereof of the present invention, or cells derived or induced from such cells to a patient who needs treatment. The effective dose can be specified based on the number of cells to be administered, for example, and appropriately determined depending on disease types or severity. In the above therapeutic method, the pluripotent stem cells of the present invention do not form any teratoma, so that no tumor is formed in a patient. Also, when autologous cell-derived Muse cells are administered, there is no need to cause bone marrow dysfunction by subjecting a patient to radiation exposure, chemotherapy, or the like. When Muse cells that are not autologous cells are used, the above treatment is performed.

Furthermore, Muse cells can be a source of iPS cells (induced pluripotent stem cells). Efficiency for preparation of iPS cells using Muse cells as a source is much higher (at least higher by 25 or more folds) than that of a case of using another type of cells (e.g., dermal fibroblasts not fractioned using SSEA-3 expression as an index) as a source.

iPS cells can be prepared by introducing a specific gene or a specific compound into Muse cells so as to alter cytoplasms. Alterations of cytoplasms include reprogramming or tumorigenesis, for which currently known methods or all methods that will be established in the future can be employed.

For example, a gene is introduced into Muse cells according to the description of JP Patent No. 4182742 or the description in FIG. 48, so that iPS cells can be established from Muse cells. Also, in addition to the method described in FIG. 48, it can be said that iPS cells can be established through introduction of a chemical substance, a foreign gene, or a foreign protein. Establishment of iPS cells from Muse cells can be performed by methods described in Examples described later, for example.

The iPS cells obtained as described above from Muse cells may also be referred to as "Muse-derived iPS cells (Muse-iPSC)." The present invention encompasses such Muse-derived iPS cells. Muse-derived iPS cells can be said to be pluripotent stem cells which were derived from Muse cell-derived and had proliferative ability.

The present invention further encompasses a cell therapy composition for allotransplantation which comprises SSEA-3 positive pluripotent stem cell derived from body tissue, which are Muse cells.

Alloplantation means the plantation of cell or tissue of another person (another individual).

Muse cells expresses HLA class I antigen among HLA (Human Lymphocyte antigen) on their surface, but do not express HLA class II antigen. When cell or tissue which has HLA class II antigen is allotransplanted, cellular immunity is activated by antigen presentation by HLA class II antigen of donor cell or tissue and transplanted cell or tissue is rejected. Therefore, when Muse cells which do not express HLA class II antigen is allotransplanted, the rejection is difficult to occur and Muse cells can be engrafted. Thus, it is not required to use immune suppressant when transplantation is carried out.

Further, Muse cells have immuno suppressive effect. That is, Muse cells can suppress the induction of differentiation of monocyte to monocyte-derived dendritic cell (MoDC) progenitor cell and the induction of differentiation of monocyte-derived dendritic cell (MoDC) progenitor cell to dendritic cell. Further Muse cells can suppress the activation of T cells. These facts show that when Muse cells are allotransplanted, Muse cells suppresses immune reaction of a donor and are not rejected by immune system of the donor. Accordingly, Muse cells can be engrafted and differentiate to many tissues and organs.

Muse cells can be used for cell therapy for allotransplantation. Muse cells are useful for regeneration medicine as described above.

Hereafter, the present invention is described in greater detail with reference to the following examples, although the present invention is not limited to these examples Example 1

Preparation and Characterization of Muse-Enriched Cell Fractions and M-Clusters

Materials and Methods

The following cells are used in Examples.

Two strains of human dermal fibroblast fractions (H-fibroblasts) and four strains of human MSC (bone marrow stromal cell) fractions (H-MSC fractions) were used as mesenchymal cells. Human fibroblast fractions were (1) H-fibroblast-1 (normal human fibroblast cells (NHDF), Lonza), and (2) H-fibroblast-2 (adult human dermal fibroblasts (HDFA, ScienCell, Carlsbad, Calif.)). Human MSC fractions, H-MSC-1, -2 and -3 were obtained from Lonza, and H-MSC-4 was obtained from ALLCELLS. Human MSC fractions are specifically described in Pittenger, M. F. et al. Science 284, 143-147 (1999); Dezawa, M. et al. J Clin Invest 113, 1701-1710 (2004); and Dezawa, M. et al. Science 309, 314-317 (2005).

Cells were cultured at 37° C. in α-MEM (alpha-minimum essential medium) containing 10% FBS and 0.1 mg/ml kanamycin with 5% $CO_2$. Cells cultured directly after their shipment were considered to be the $1^{st}$ culture. When cells reached 95% confluence, cells were expanded at a ratio of 1:2 (cell culture solution: medium). In this study cells from the $4^{th}$ to $10^{th}$ subcultures were used.

Human ES cells (hESC) used herein were kyoto hESC-1 (KhES-1) obtained from Kyoto University.

Mouse ES cells (TT2 cells) and human ES cells (KhES-1) were maintained on mouse embryonic feeder (MEF) cells established from 12.5-day embryos of C57BL/6 mice.

Experiments were conducted by the following methods.

1. Stress Conditions for Mesenchymal Cells

To perform exposure to stress conditions including culture under poor nutrition, culture under low serum, culture under low $O_2$, repetitive-trypsin incubations and long-term trypsin incubation, the following six conditions were employed:
1) culture in non-serum containing medium (STEMPRO MSC SFM, Invitrogen) for 2 days (serum free);
2) culture in Hanks' Balanced Salt Solution (HBSS) buffer (Invitrogen) for 2 days (HBSS);
3) culture in 10% FBS in α-MEM combined with low $O_2$ (1% $O_2$) for 2 days (10% FBS+Low $O_2$);
4) three consecutive 1-hr incubations (a total of 3 hours of trypsin incubation) (Try 3×1 hr) in trypsin (0.25% trypsin-HBSS);
5) long-term trypsin-incubation (LTT) for 8 hrs (LTT 8 hr); and
6) LTT for 16 hrs (LTT 16 hr).

For negative controls, human peripheral mononuclear cell fractions were used.

For conditions 4), 5) and 6), approximately $1\times10^5$ to $5\times10^5$ cells were suspended in 5 ml trypsin solution, and incubated. Cells from stress conditions 1) through 3) were collected by a 5-min trypsin incubation, and cells from stress conditions 4) to 6) were transferred directly to tubes.

Large numbers of dead cells resulting from stress conditions were disrupted by vortexing. Specifically, 5 ml medium containing a maximum of 500,000 cells was transferred into a 15-ml Falcon tube, followed by 3 min of vortexing at 1800-2200 rpm/min using a vortex mixer (IKA Works, Inc.). Centrifugation was performed at 2000 rpm for 15 min, so as to remove the supernatant. Collection efficiency of live cells after vortexing ranged from approximately 70% to 80%.

2. MC Culture

In the Examples, cells were subjected to suspension culture in methylcellulose-containing medium. Culture in methylcellulose-containing medium is referred to as "MC culture." MC culture is as described in Nakahata, T. et al., Blood 60, 352-361 (1982).

Culture dishes were first coated with poly-HEMA (poly (2-hydroxyethyl methacrylate)) to avoid attachment of cells to the bottom of the dish. In brief, 600 mg of poly-HEMA (SIGMA) was dissolved in 40 ml of 95% EtOH by stirring at 37° C., added to the dish (e.g., 40 μl/well for 96-well culture dish and 200 μl/well for 12-well culture dish), and the dish was air-dried overnight.

MC (MethoCult H4100, StemCell Technologies) was suspended in 20% FBS+α-MEM to a final concentration of 2%. The cell concentration in the semisolid MC medium was adjusted to be $8\times10^3$ cells/ml at this concentration, so that the cell-to-cell distance was sufficiently large to minimize cell aggregation. Cells and MC medium were mixed thoroughly by gentle pipetting, and the mixture was transferred to a polyHEMA-coated dish. To prevent drying, a volume equal to one tenth of the initial MC culture of 10% FBS in α-MEM was gently added to the dish every 3 days.

Cell clusters (referred to as Muse cell-derived embryoid body-like cell cluster=M-clusters since cell clusters were clusters from the pluripotent stem cells, Muse cells, of the present invention) were cloned on day 7. 0.01 M PBS was added to the medium, the cells centrifuged at 2000 rpm for 20 min, and the supernatant discarded. This procedure was repeated three times to wash the cells. The collected cell pellet was finally suspended in 10 μl of 0.01 M PBS containing Trypan Blue, applied to a glass slide, and the entire area was automatically imaged using phase contrast microscopy. Only multicellular clusters larger than 25 μm that were negative for Trypan Blue and had an appearance similar to hES cells were counted as M-clusters. The frequency of M-cluster formation was calculated as the number of M-clusters divided by the number of all live cells (all the Trypan Blue-negative cells). Since determination of the precise number of cells in each M-cluster was difficult, each aggregate was counted as one cell, irrespective of its size.

For making cell clusters from hES cells, they were carefully isolated from feeder cells so as not to include feeder cells, transferred to MC culture as described above, and imaged by phase contrast microscopy on day 3 of culture.

3. Single-Cell Suspension Culture

A 96-well dish was coated with polyHEMA as described above. Following a limiting dilution of cells with 10% FBS in α-MEM, single cells were plated into each well. After plating, the actual number of cells deposited in each well was determined by visual inspection using a phase contrast microscope. Empty wells or wells with more than one cell were marked and excluded from the analysis. The calculation of M-cluster formation was performed on day 10 of culture. The frequency of M-cluster formation was calculated from 3 experiments for each strain with a minimum of 250 wells per experiment.

4. Alkaline Phosphatase Staining

M-clusters from H-fibroblast and H-MSC were washed several times with a sufficient volume of saline. Staining was performed using the Leukocyte Alkaline Phosphatase kit (Sigma).

5. In Vitro Differentiation of M-Cluster

After 7 to 10 days of MC culture or single-cell suspension culture, single M-clusters from H-fibroblast fractions and H-MSC fractions were picked up with a glass micropipette and transferred onto a gelatin-coated culture dish or cover glass. After another 7 days of incubation, cells were dispersed from cell clusters. Cells were subjected to immunohistochemical and RT-PCR analyses to determine the presence or the absence of differentiation of the cells.

6. Immunohistochemistry

Cells were fixed with 4% paraformaldehyde in 0.01 M PBS. Muse-enriched cell fractions and M-clusters both from H-fibroblasts and H-MSC fractions were collected by centrifugation, embedded in OCT compound, and 8 µm thick cryo-sections were cut. Cell clusters were fixed on gelatin-coated cover glasses and then subjected to immunohistochemical analysis.

The following primary antibodies against: Nanog (1:500, Chemicon), Oct3/4 (1:800, kindly provided by Dr. H. Hamada, Osaka University, Japan), Sox2 (1:1000, Abcam), PAR4 (1:100, Santa Cruz), SSEA-3 (1:20, DSHB), smooth muscle actin (1:100, Lab Vision), neurofilament M (1:200, Chemicon), α-fetoprotein (1:100, DAKO), mouse Numb-like (1:500, kindly provided by Dr. Yuh-Nung Jan, University of California San Francisco), type 1 collagen (1:20, Southern Biotech), Musashi, Nestin, Neuro D, MAP2, and Osteocalcin were used. Alexa 488- or Alexa 568-conjugated anti-rabbit IgG, anti-mouse IgG or anti-mouse IgM antibodies (Molecular Probes, Carlsbad, Calif.) were used as secondary antibodies for immunohistochemical analysis.

7. Determination of Karyotypes

Karyotypes of cells clonally expanded from M-clusters (obtained through repetition (1 to 3 times) of a cycle of collecting single cells from M-clusters and then causing cells to form cell clusters again) both from H-fibroblast fractions and H-MSC fractions were determined by quinacrine-Hoechst staining.

8. Injection of Cells into the Testes of Immunodeficient Mice

Naive cell fractions and Muse-enriched cell fractions and M-clusters both from H-fibroblast fractions and H-MSC fractions were used. Muse-enriched cell fractions were prepared by adding serum to the cells after LTT and followed by three washes with 0.01 M PBS. M-clusters were collected from MC cultures and also washed three times with PBS. $1 \times 10^5$ cells were suspended in PBS and injected using glass microtubes into the testes of NOG mice (Registered trademark, mouse NOD/Shi-scid, IL-2RγKO Jic, 8 weeks old, International Council for Laboratory Animal Science (ICLAS) Monitoring Center Japan). The average volume of the cells in M-clusters was measured using the 3D-graphic analysis software provided with the laser confocal microscope (50 M-clusters were measured and the total volumes of the clusters were divided by the number of nuclei), which resulted in $1.5 \times 10^5$ cells per 1 µl volume of collected M-cluster pellet. Each testis of a NOG mouse was then injected with the volume corresponding to $1 \times 10^5$ cells, and the mice were subjected to the experiment for analysis 6 months after the injection.

As controls, $1 \times 10^6$ mouse ES cells (for positive control, n=3) and mitomycin C-treated MEF cells (mouse embryonic feeder cells for negative control, n=3) were injected into SCID mice testes, and the mice were subjected to the experiment 8 weeks after the injection.

9. High-Resolution Analysis of Cells by Optical Microscope

Muse cells and M-clusters from H-fibroblast fractions and H-MSC fractions were observed using a stable high-resolution optical microscope for cell types such as human MSC, fibroblasts, and neuronal cells.

10. Ultrathin Sectioning for Electron Microscopy

M-clusters, SSEA-3(+) and SSEA-3(−) cells both from H-fibroblast fractions and H-MSC fractions as well as cell clusters formed by hES cells were centrifuged. The pellets were fixed with 2.5% glutaraldehyde in 100 mM phosphate buffer (pH 7.2) for 30 min. The fixed samples were embedded in 1% agar. The embedded samples were trimmed to 1 $mm^3$, washed with PBS, and stained with 2% $OsO_4$ in 100 mM phosphate buffer (pH 7.2) for 10 minutes at 4° C. The samples were washed with distilled water and then stained with 5 drops of 2% uranyl acetate (UA) for 20 min at 4° C. After washing with distilled water, the stained samples were incrementally dehydrated with 50%, 70% and 90% ethanol for 10 min each at 4° C., and then completely dehydrated with three exchanges of 100% ethanol. The samples were incubated with propylene oxide for 5 min (for exchange) and embedded in 50% epoxy resin in propylene oxide for 60 min, followed by embedding in 100% epoxy resin and hardening at 60° C. overnight. Ultrathin sections were cut with a thickness of 70-80 nm and observed in a 100 kV electron microscope using a CCD camera.

11. Growth Rate of M-Clusters

To calculate the fraction doubling time for cells in the M-clusters from both H-fibroblast fractions and H-MSC fractions, the clusters were each transferred to 96-well plates and treated with trypsin for 15 min followed by pipetting with a glass micropipette. The number of cells in each well was counted. At least 20-30 M-clusters were analyzed at predetermined time points (day 1, 3, 5, 7, 9, 10, 11, 12, 13 and 14).

12. RT-PCR

Naive cell fractions (about 10,000 cells per well of a 24-well plate) and cells in vitro differentiated from single M-clusters (1 to 3 cycles) both from H-fibroblast fractions and H-MSC fractions (about 10,000 cells per well of a 24-well plate) were used. Total RNA was extracted and purified using NucleoSpin RNA XS (Macherey-Nagel). First-strand cDNA was generated using the SuperScript VILO cDNA Synthesis Kit (Invitrogen). The PCR reactions were performed using appropriate primers designed and Ex Taq DNA polymerase (TaKaRa Bio Inc.). The used primers were as follows.

Total RNA was extracted and purified using NucleoSpin RNA XS (Macherey-Nagel). First-strand cDNA was generated using the SuperScript VILO cDNA Synthesis Kit (Invitrogen). The PCR reactions were performed using appropriate primers designed and Ex Taq DNA polymerase (TaKaRa Bio Inc.). As positive controls, human fetal liver (Clonetech) was used for α-fetoprotein primers and human complete embryos were used for others.

13. Quantitative-PCR (Q-PCR)

Total RNA was collected from naive cell fractions, Muse-enriched cell fractions and M-clusters from H-fibroblast-1, H-fibroblast-2, H-MSC-1, and H-MSC-2 using the RNeasy Mini Kit (Qiagen GmbH) and cDNA was synthesized using the $RT^2$ First Strand Kit (SA Biosciences). Customized primers were purchased from SA Biosciences and the DNA was amplified by quantitative PCR with the 7300 real-time PCR system (Applied Biosystems). The data were processed using the $\Delta \Delta C_T$ method (Livak K J et al., Methods 25: 402-408, 2001).

14. DNA Microarray Analysis

Naive cell fractions, Muse-enriched cell fractions and M-clusters from H-fibroblast-1, H-fibroblast-2, H-MSC-1, and H-MSC-2, as well as the mixture of human peripheral mononuclear cells obtained from 4 healthy volunteers were used. Total RNA was collected using the RNeasy Mini Kit (Qiagen) and analyzed by DNA microarray (TaKaRa Bio Inc.). Array signals were processed and normalized using the Affymetrix Expression Console V1.1 software. Pathway Studio 6.0 (Ariadne Genomics) was used to assign the differentially expressed genes to functional categories in the Gene Ontology. Hierarchical clustering was performed at a Euclidean distance based on differentially expressed genes with average linkage clustering by MeV4 (Saeed A I et al., Biotechniques 34(2): 374-378, 2003).

15. Detection of Telomerase Activity

Muse-enriched cell fractions and M-clusters from H-fibroblast fractions and H-MSC fractions, and Hela cells were used. Telomerase activity was detected using the TRAPEZE XL telomerase detection kit (Millipore) and Ex Taq polymerase (TaKaRa Bio Inc.). Fluorescence intensity was measured with a micro plate reader (Tecan).

16. Bisulfite Sequencing

Genomic DNA (1 µg) from naive cell fractions, Muse-enriched cell fractions, or M-clusters from H-fibroblast fractions and H-MSC fractions was treated using CpGenome DNA modification kit (Chemicon). DNA was purified using a QIAquick column (Qiagen). The promoter regions of human Oct3/4 and Nanog genes were amplified by PCR and then the PCR products were subcloned into pCR2.1-TOPO. Up to 10 clones of each sample were verified by sequencing using M13 universal primers, so that the methylation in each promoter region was detected. Primers described in Shimazaki T et al., EMBO J, 12:4489-4498, 1993 were used for PCR amplification.

17. M-Cluster Formation Directly from Human Bone Marrow Aspirates

Three human bone marrow aspirates from healthy donors were purchased from ALLCELLS. Mononuclear cell fractions were collected using the Lymphoprep Tube (Axis-Shield PoC AS) and subjected to MC culture directly (without trypsin incubation) or after 8 hr-LTT as described above. M-clusters were counted on day 7.

18. MACS Sorting

Figure 5:
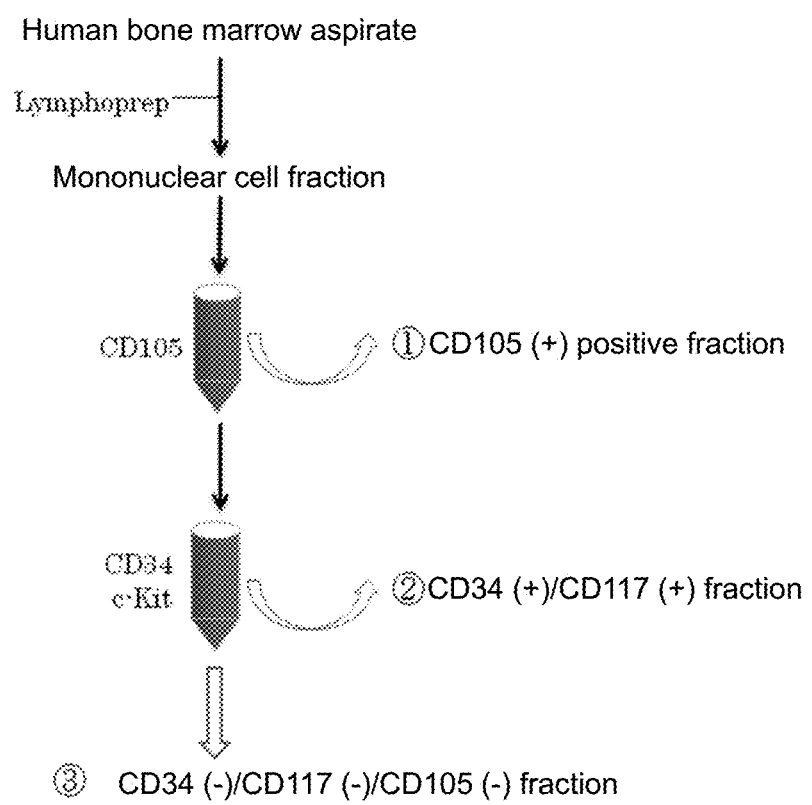
FIG. 5 shows protocols for MACS sorting.

Mononuclear cell fractions from human bone marrow aspirates of three healthy donors (ALLCELLS) were first reacted with microbeads-conjugated anti-CD105 antibody and sorted using MS Columns (Miltenyi Biotech). CD105 (+) cells were collected as Fraction 1 (mesenchymal cell population). CD105(−) cells were incubated with a mixture of anti-CD34 and anti-CD117 antibodies conjugated to microbeads and sorted again to obtain CD34(+)/CD117(+) cells (Fraction 2 corresponding to a hematopoietic stem cell population) and CD105(−)/CD34(−)/CD117(−) cells (Fraction 3, the rest of the cell populations) (FIG. 5). The thus collected samples were subjected to 8 hr-LTT and then the formation of M-clusters was determined.

19. Flow Cytometry and Cell Sorting

Cells were incubated with phycoerythrin-labeled antibodies against CD11c, CD29, CD34, CD44, CD45, CD49f, CD54, CD71, CD90, CD105, CD166, CD271 or vWF (Becton Dickinson) or with anti-SSEA-3 antibodies (Millipore). In the case of labeling with the anti-SSEA-3 antibody, cells were further incubated with FITC-conjugated anti-rat IgM antibodies. Calcium and magnesium-free 0.02 M PBS supplemented with 2 mM EDTA and 0.5% bovine serum albumin was used as the FACS antibody diluents. Data were acquired and analyzed using FACSCalibur (Becton Dickinson) and the CellQuest software or using FACSAria and the DIA software. For cell sorting, cells were incubated with anti-SSEA-3 antibody in the FACS antibody diluents and sorted by FACSAria (Becton Dickinson) using a low stream speed and in the 4-way purity sorting mode.

20. Statistical Analysis

Data are expressed with average±SEM. Data were compared via paired comparison according to the Bonferroni method using ANOVA.

Results

A. Stress Conditions for H-Fibroblast Fractions and H-MSC Fractions

Examples of the results of exposure of H-fibroblast fractions and H-MSC fractions to stress conditions are shown in Table 1(below).

After exposing the cells to stress conditions and vortexing, Trypan Blue staining was used to count the number of live cells, from which the survival rate was calculated. The surviving cells were collected and grown in MC culture for 7 days. Stress conditions 2) resulted in a large number of dead cells and low efficiency for collecting surviving cells. It was therefore not possible to accurately determine the number of formed M-clusters, and the number of M-clusters for stress conditions 2) is thus denoted as ND (not determined) in Table 1.

Among the 6 stress conditions tested, the 16 hr-trypsin incubation was most effective for H-fibroblast fractions and the 8 hr-trypsin incubation for H-MSC fractions. When this experiment was repeated using two strains of H-fibroblast fractions and four strains of H-MSC fractions, the same trend was observed. M-clusters could not be recognized in the negative control using human peripheral mononuclear cells. Examples of typical observed values are shown in Table 1.

TABLE 1

Survival rates after exposure to stress conditions and M-cluster formation in MC culture in H-fibroblasts, H-MSCs and human peripheral mononuclear cells.

| | | Start cell number | Survival after stress (%) | Cell cluster formation in MC culture (>25 µm) (% to survived cells) |
|---|---|---|---|---|
| | H-fibroblast-1 | | | |
| 1 | Non-serum | 30,000 | 75 | 7 |
| 2 | HBSS | 2,000,000 | 6 | ND |
| 3 | 10% FBS + LowO2 | 30,000 | 99 | 8 |
| 4 | Tryp 3 × 1 hr | 2,000,000 | 0.3 | 6 |
| 5 | LTT 8 hr | 2,000,000 | 1 | 15 |
| 6 | LTT 16 hr | 500,000 | 5 | 20 |
| | H-MSC-1 | | | |
| 1 | Non-serum | 30,000 | 44 | 5 |
| 2 | HBSS | 2,000,000 | 2 | ND |
| 3 | 10% FBS + LowO2 | 300,000 | 99 | 8 |
| 4 | Tryp 3 × 1 hr | 380,000 | 0.9 | 9 |
| 5 | LTT 8 hr | 380,000 | 10 | 21 |
| 6 | LTT 16 hr | 500,000 | 3 | 14 |
| | Human peripheral mononuclear cells | | | |
| 5 | LTT 8 hr | 300,000 | 2 | 0 |
| 6 | LTT 16 hr | 300,000 | 1 | 0 |

ND (not determined): M-clusters could not be calculated accurately, because the final fraction contained a large number of dead cells and efficiency for collecting surviving cells was low.

Figure 6A:
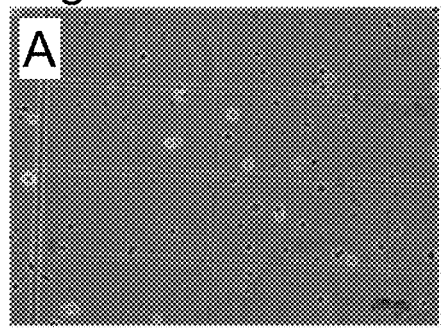
FIGS. 6A and 6B show photos (stained images) showing the removal of dead cells when human fibroblast (H-fibroblast) fractions were subjected to 16-hr-long trypsin incubation (FIG. 6A), 3 minutes of vortexing at 1800 rpm-2200 rpm/minute (FIG. 6B), and then trypan blue staining.
Figure 6B:
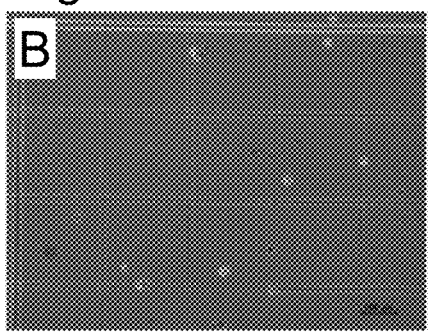

Among the 6 stress conditions tested, the 16 hr-trypsin incubation (H-fibroblast fractions) and the 8 hr-trypsin incubation (H-MSC fractions) were the most effective for the formation of M-clusters. A series of procedures including 16 hr- or 8 hr-trypsin incubation followed by vortexing at 1800-2200 rpm/min for 3 min and centrifugation at 2000 rpm for 15 min was termed "Long-Term Trypsin incubation (LTT)" and used for the enrichment of Muse cells. Collection efficiency of live cells after vortexing ranged from approximately 70% to 80% (FIGS. 6A and 6B).

B. Criteria for M-Clusters

Figure 7A:
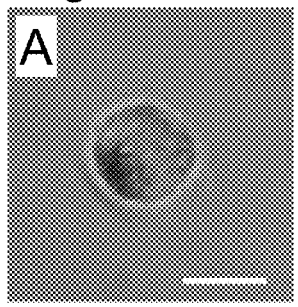
Figure 7B:
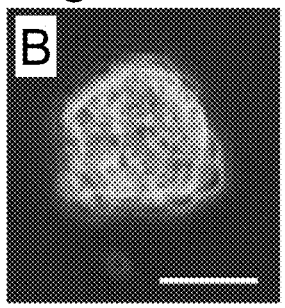
Figure 7C:
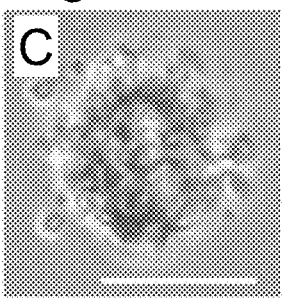
Figure 7D:
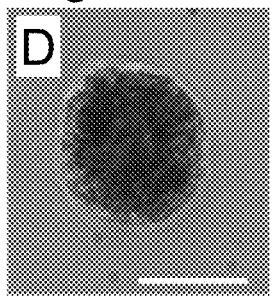
Figure 7E:
Figure 7G:
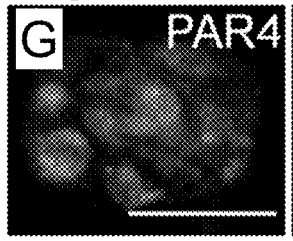

In the Examples, criteria for M-clusters were established. The average diameter of single cells in Muse-enriched cell fractions both from H-fibroblast fractions and H-MSC fractions was 10-13 μm (FIG. 7A). When these cells were transferred to MC culture, the cells started to divide. The size of the individual cells became smaller after cell division, and the gradually forming multicellular clusters comprised cells of 8-10 μm in diameter (FIGS. 8E and 8F). The size and appearance of the cells were similar to those of human ES cells subjected to MC culture (FIGS. 7B and 7C). On day 7, most of the multicellular clusters became larger than 25 μm, having a diameter of 100-150 μm. The cell clusters had an appearance very similar to cell clusters formed by ES cells. Cell clusters larger than 25 μm were collected using D25 μm filters (FIG. 7C) and then analyzed (up to 100 M-clusters each from H-fibroblast fractions and H-MSC fractions) by immunocytochemistry. Most of M-clusters were positive for the pluripotency markers Nanog, Oct3/4, Sox2, PAR4 and SSEA-3 and also positive for alkaline phosphatase staining (FIGS. 7E-7G). Pluripotency markers could be detected or not detected in cell clusters smaller than 25 μm, but their localization was sometimes atypical and the appearance of the cells was more similar to that of cells in Muse-enriched cell fractions.

Based on these findings, only multicellular clusters larger than 25 μm in diameter were counted as M-clusters.

C. Analysis of Cell Clusters Generated from Human Mesenchymal Cell Fractions

Figure 9A:
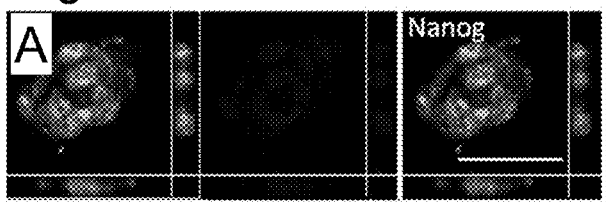
FIGS. 9A, 9B, 9C, 9D, 9E and 9F show photos showing the characteristics of cell clusters from Muse-enriched cell fraction from H-fibroblasts and human MSCs (H-MSCs).
Figure 9B:
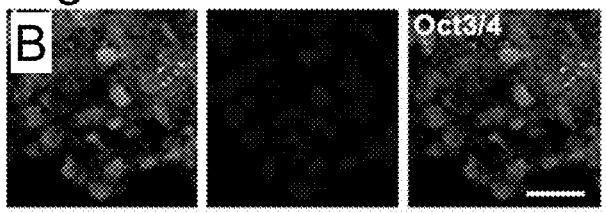
Figure 9C:
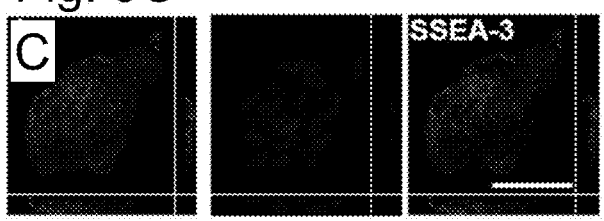
Figure 9D:
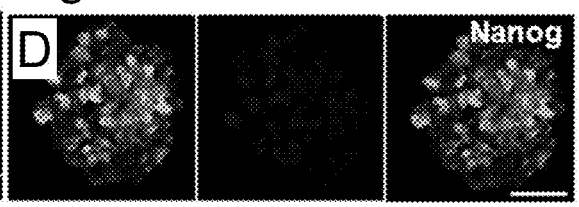
Figure 9E:
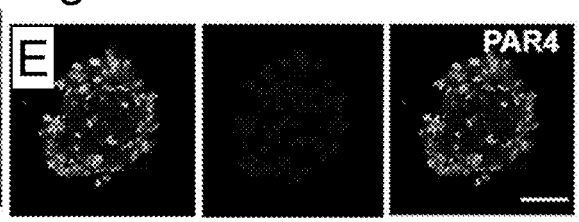
Figure 9F:
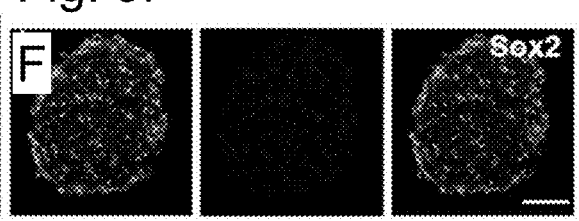
Figures 10A, 10B, 10C:
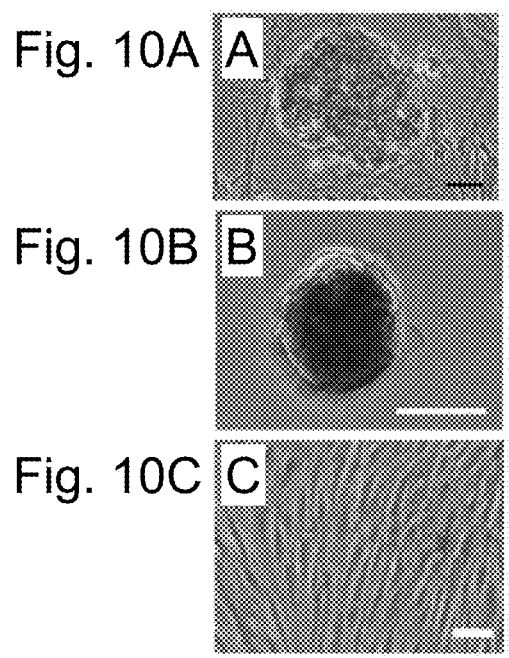
FIGS. 10A, 10B and 10C show photos showing the characteristics of cell clusters formed from Muse-enriched cell fractions of H-fibroblasts and human MSCs.

It is well known that dormant tissue stem cells are activated when the tissue is exposed to stress, burdens or damages. In the Examples, H-MSC fractions and H-fibroblast fractions were exposed to stress conditions by various methods. Specifically, the stress conditions tested were: treatment with non-serum medium; treatment with Hanks' Balanced Salt Solution (HBSS); treatment with low $O_2$ concentration; and long-term trypsin incubation (LTT) for a total of 3, 8, or 16 hours. Cells that had survived the stress conditions were collected and then suspended in methylcellulose (MC)-containing medium (referred to as MC culture), followed by 7 days of MC culture at a density of 8000 cells/mL (FIG. 8D). Each condition gave rise to cell clusters with sizes up to 150 μm in diameter (FIGS. 8E and F). FIG. 8C shows MC culture of H-fibroblast-1 fractions on day 0, FIG. 8D shows MC culture of the same on day 7. Formation of the highest number of cell clusters were observed in H-fibroblast fractions subjected to 16-hr LTT and in H-MSC fractions subjected to 8-hr LTT. FIGS. 8E and F show cell clusters (M-clusters) formed from H-fibroblast-1 fractions. FIG. 8E shows MC culture on day 7 and FIG. 8F shows suspension culture of single cells on day 10. Cell clusters were sorted using filters with different pore-sizes according to their size, so that immunocytochemical analysis was performed. The cell clusters with a diameter larger than 25 μm contained cells positive for the pluripotent stem cell markers Nanog, Oct3/4, SSEA-3, PAR-4 and Sox2 (FIGS. 9A-9F) and positive for alkaline phosphatase staining (FIGS. 10 A-10C). Electron microscopy revealed that cell clusters generated from H-fibroblast fractions and H-MSC fractions had the same characteristics as clusters formed by ES cells. The cells showed a similar nucleus/cytoplasm ratio, fewer organelles, and presence one or two big nucleoli in the nucleus (FIGS. 11 A-11C).

Cells capable of forming cell clusters positive for pluripotency markers and alkaline phosphatase staining by suspension culture were found from the H-MSC fractions and H-fibroblast fractions of a living body. The present inventors named these cells "Muse cells" (multilineage differentiating stress enduring cells). Cell populations formed from H-fibroblast fractions subjected to 16 hr-LTT and H-MSC fractions subjected to 8 hr-LTT are referred to as "Muse-enriched cell fractions (Muse-enriched cell populations)." Single cells obtained from the cell populations were subjected to suspension culture. Formation of M-cluster was observed in 9%-10% of Muse-enriched cell fractions. This indicates that the muse-enriched cell fractions contained about 9%-10% Muse cells.

Figure 12:
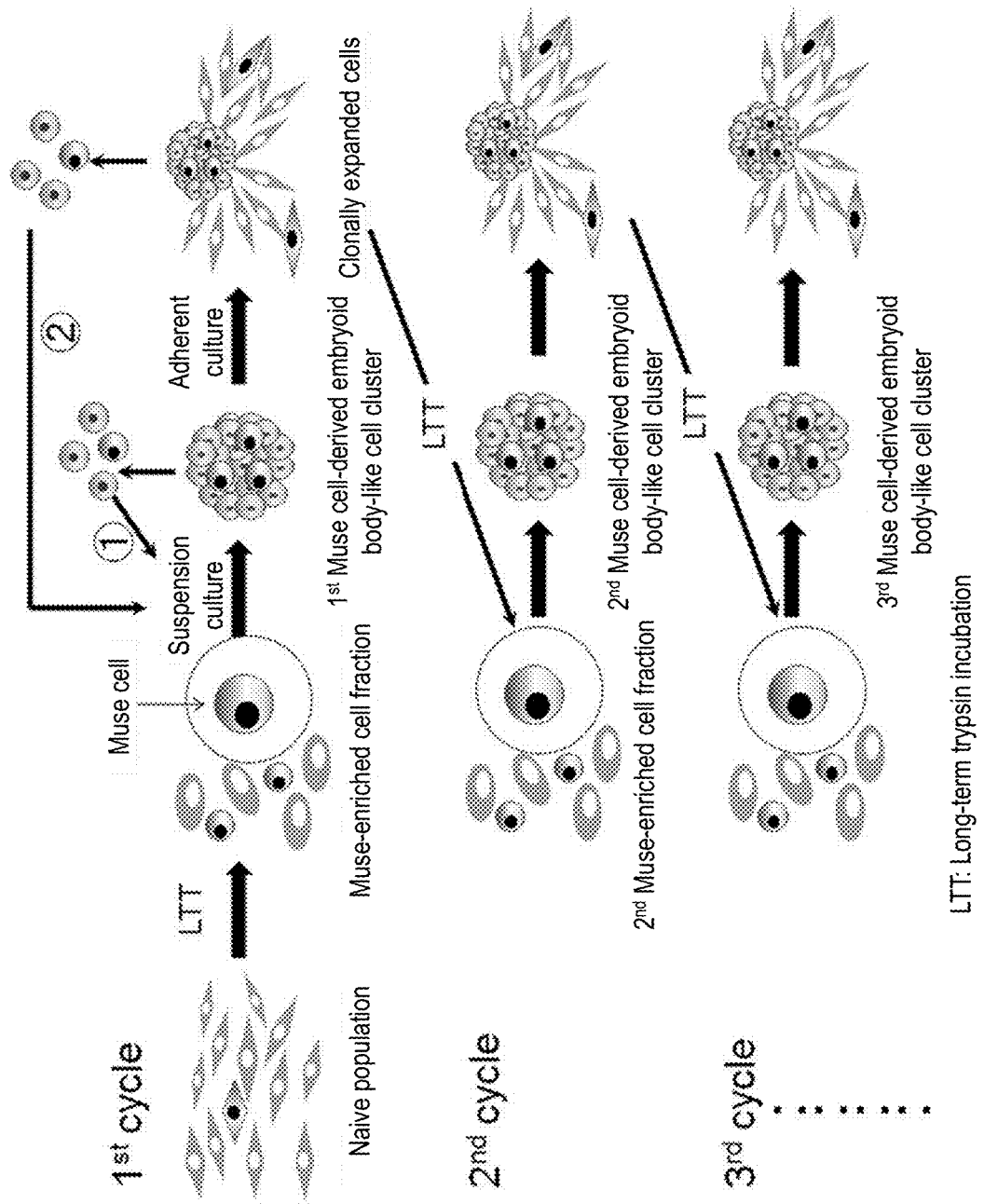
FIG. 12 demonstrates the clonality and self-renewal of M-clusters. Specifically.
Figure 13:
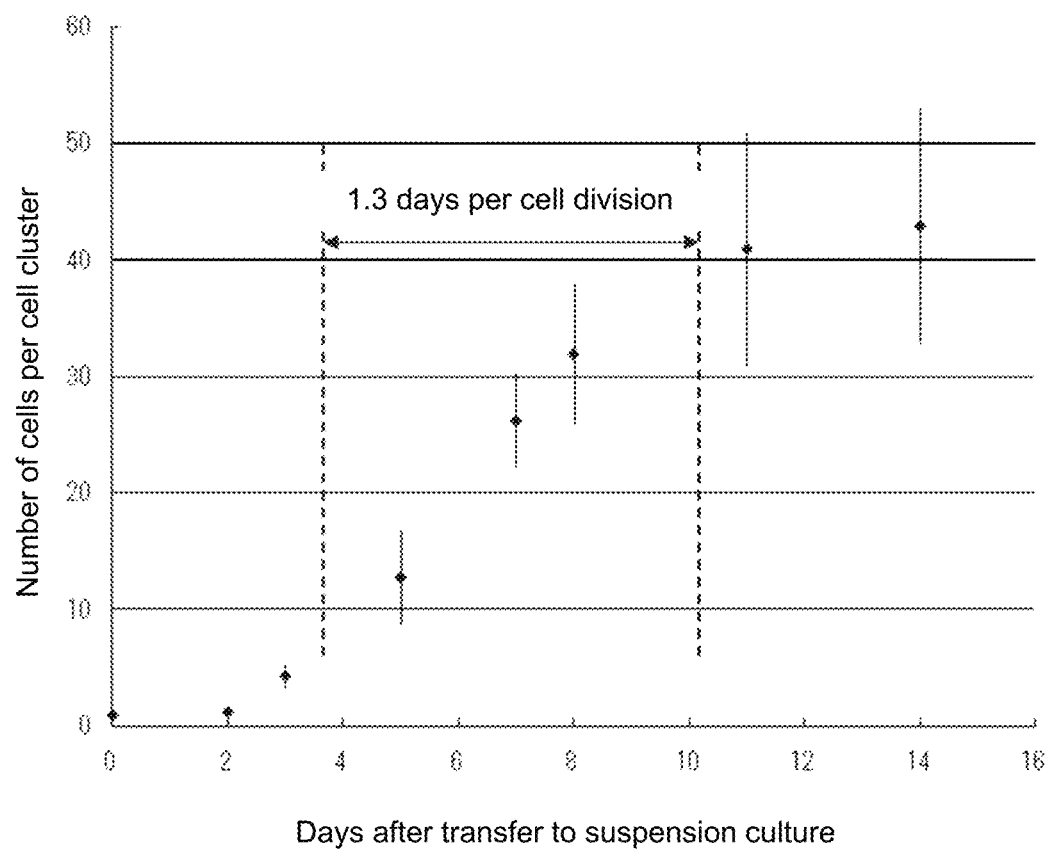
FIG. 13 shows the growth rate of Muse cells in suspension culture.

The growth of Muse cells isolated was examined. Cells began to divide after 1-2 days in MC culture and kept dividing at a rate of approximately 1.3 days/cell division until day 10 (FIG. 13). However, cell growth gradually slowed down by days 11-12 and seized by around day 14, with cell clusters that reached a maximum size of 150 μm in diameter. When the formed M-clusters were directly dissociated into single cells by a 5-min trypsin incubation and returned to single-cell suspension culture, the cells remained alive but divided very slowly (5-7 days/cell division) or sometimes not at all (FIG. 12 (1); circle 1 in the figure). Thus, once their proliferation has been limited (or once their growth rate has been lowered), Muse cells do not re-accelerate their proliferation as long as they are maintained in suspension culture. However, transfer of single M-clusters to adherent culture reinitiated cell proliferation. After 5-7 days, when relatively small-scale cell populations, at a stage of 3,000 to 5,000 cells, were dissociated by 5 minutes of trypsin incubation and subjected to MC culture, 40% of the cells formed new cell clusters (FIG. 12 (2); circle 2 in the figure). When the clonally expanded cell populations were allowed to reach a scale of about $5\text{-}10\times10^4$ cells and then subjected to LTT to produce Muse cells ($2^{nd}$ cycle) again, nearly 10% of these cells formed M-clusters (FIG. 12). This culture cycle was repeated five times, consisting of LTT-suspension culture-adherent culture, so that every cell generation showed the similar behavior and frequency of M-cluster formation. The $5^{th}$ generation M-clusters (at the $5^{th}$ cycle) were still positive for pluripotency markers and alkaline phosphatase staining.

Figure 14:
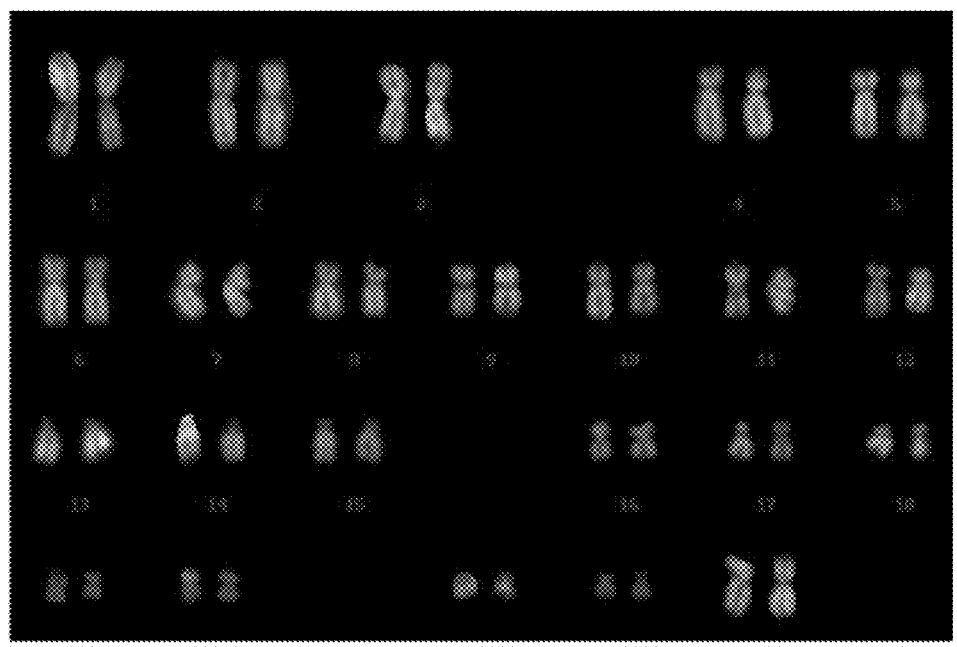
FIG. 14 shows a normal karyotype of cells clonally expanded from a single M-cluster (H-fibroblast-1-derived, $1^{st}$ generation (cycle)).

To confirm that these phenomena were not due to abnormal cells that had undergone mutation or the like, karyotypes of cells were determined. The karyotypes of most cells clonally expanded from M-clusters were normal and did not show detectable chromosomal abnormalities (FIG. 14). These results demonstrate that the phenomena resulted from normal cells.

These results demonstrate the capacity of Muse cells for self-renewal and clonal expansion. Muse cells grow through the series of cycle, "Muse cells-M-cluster-clonal expansion." It might be possible to obtain large numbers of Muse cells from mesenchymal cell fractions.

D. Differentiation of M-Cluster into the Three Germ Layers

Figure 16:
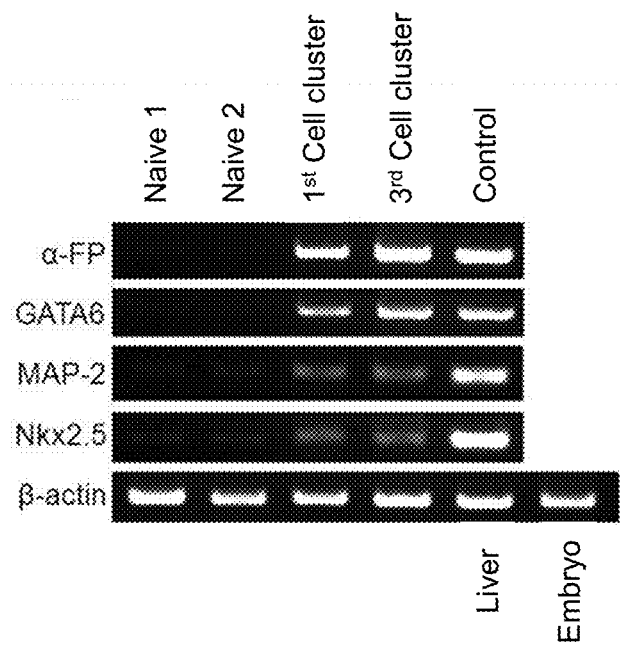
FIG. 16 shows the results of RT-PCR analysis for α-fetoprotein (α-FP) expression, GATA6 expression, MAP-2 expression, and Nkx2.5 expression in cell populations prepared by culturing a naive cell fraction, and $1^{st}$-generation and $3^{rd}$-generation M-clusters from H-fibroblasts on gelatin so as to induce spontaneous differentiation. As positive controls, human fetus liver was used for α-FP and whole human embryos were used for GATA6, MAP-2, and Nkx2.5.

To confirm differentiation ability, single M-clusters were transferred onto gelatin-coated dishes and analyzed for differentiation. On day 7, α-smooth muscle actin (mesodermal marker), desmin (mesodermal marker), neurofilament-M (ectodermal marker), α-fetoprotein (endodermal marker), or cytokeratin-7 (endodermal marker) were detected (FIGS. 15 A-15C). RT-PCR confirmed that $1^{st}$ and $3^{rd}$ generation M-clusters ($1^{st}$ to $3^{rd}$ cycles) expressed α-fetoprotein and GATA6 (endodermal marker), microtubule-associated protein-2 (MAP-2) (ectodermal marker), and Nkx2.5 (mesodermal marker) while no differentiation was observed in naive H-fibroblasts or MSC fractions cultured on gelatin-coated dishes (FIG. 16).

Figure 17:
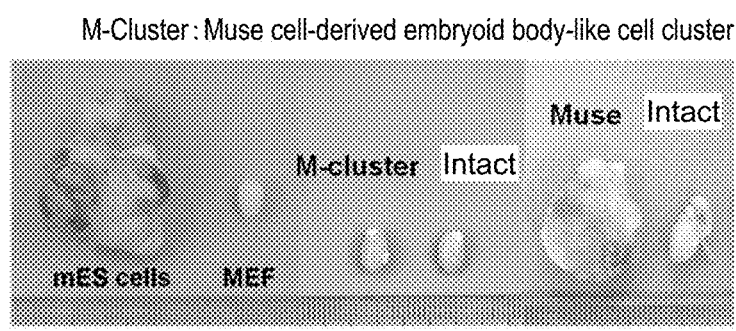
FIG. 17 show the testis of immunodeficient mice to which a Muse-enriched cell fraction was administered.

Muse-enriched cell fractions, M-clusters, or ES cells were injected into the testes of immunodeficient mice, so as to confirm teratoma formation (FIG. 17). Histological examination of the testes revealed that within 8 weeks all mice injected with ES cells developed teratomas. However, remaining transplanted human cells and differentiation into various cell species were detected in the testes of 10 out of 13 mice injected with Muse-enriched cell fractions and 10 out of 11 mice injected with M-clusters as shown in FIG. 17. Teratoma formation was never detected until at least 6 months in groups to which Muse cell-enriched cell fractions or M-clusters had been transplanted.

These data suggest that H-fibroblast fraction-, and H-MSC fraction-derived Muse cells, and M-clusters are capable of differentiating into the 3 germ layers both in vitro and in vivo.

E. Quantitative PCR

Figure 18:
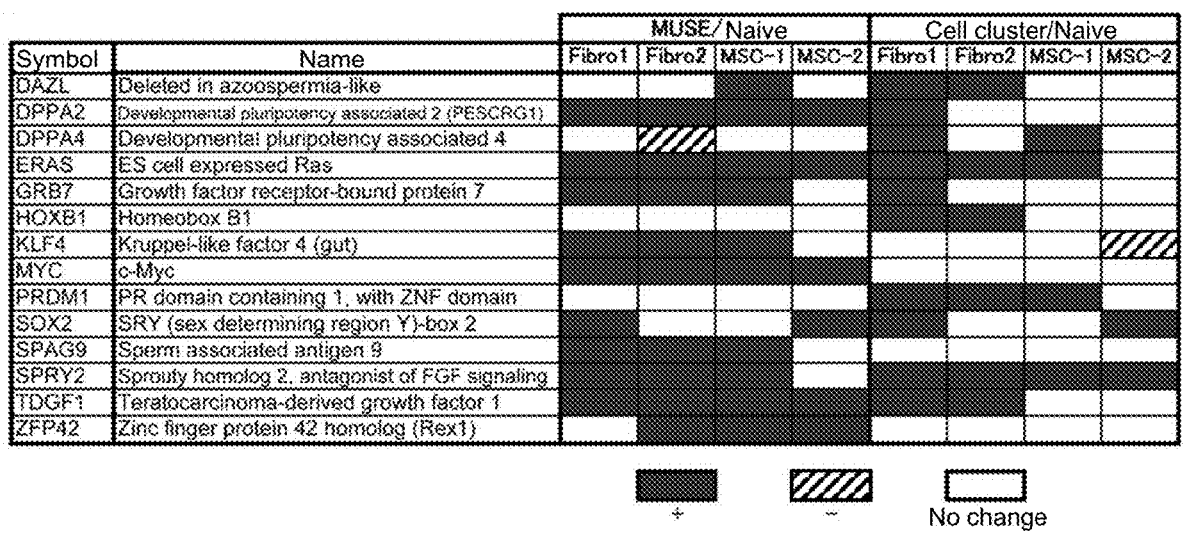
FIG. 18 shows the results of quantitative PCR for factors involved in pluripotency and undifferentiated cell states of H-fibroblasts (Fibro-1 and Fibro-2) and H-MSCs (MSC-1 and MSC-2) (No. 2). Each pattern given in a column in FIG. 18 indicates the result of comparing the gene expression level in Muse-enriched cell fractions or M-clusters (day 7) with the same in naive cell fractions. A white pattern indicates that the ratio of the gene expression level in the Muse-enriched cell fractions or the M-clusters to the same in naive cell fractions is greater than ⅓ (1:3) but is lower than 3 (3:1). A gray pattern indicates that the ratio of the gene expression level in the Muse-enriched cell fractions or the M-clusters to the same in naive cell fractions is greater than 3 (3:1). A pattern of oblique lines indicates that the ratio of the gene expression level in the Muse-enriched cell fractions or the M-clusters to the same in naive cell fractions is lower than ⅓ (1:3).

Expression of markers relating to pluripotency and differentiation state is shown in FIG. 18. The expression levels of Nanog were not so high in Muse-enriched cell fractions and cell clusters, compared with naive cells. Some pluripotent stem cells did not express Nanog at high levels (Chou Y F et al., Cell 135, 449-461 (2008)); Bui H T et al., Development. 135(23):3935-3945 (2008)). Similar to Nanog, Oct-4 was expressed at a low level in reprogramming somatic cells compared with mouse ES cells, as determined by Q-PCR (Bui H T et al., Development. 135 (23): 3935-3945 (2008)). Therefore, the expression levels of Nanog and other pluripotency markers are not so important for pluripotency.

F. Gene Expression in Muse-Enriched Cell Fractions and M-Clusters

It was found by using quantitative PCR that some markers for pluripotency and an undifferentiated cell state were up-regulated to various degrees in both Muse-enriched cell fractions and M-clusters. Muse-enriched cell fractions merely contained 9%-10% Muse cells as described above. However, compared to naive cell fractions, the genes showed tendency of higher-degree or moderate up-regulation in Muse-enriched cell fractions: Rex1 (ZFP42), Sox2, KLF-4, c-Myc, DPPA2 (developmental pluripotency associated 2), ERAS, GRB7 (growth factor receptor-bound protein 7), SPAG9 (sperm associated antigen 9), and TDGF1 (teratocarcinoma-derived growth factor 1). The genes showed tendency of higher degree or moderate up-regulation in M-clusters were: DAZL (azoospermia-like), DDX4 (VASA), DPPA4 (developmental pluripotency associated 4), Stella, Hoxb1, PRDM1, and SPRY2 (sprouty homolog 2) (FIG. 18) compared with naive cells.

Overall gene expression in H-fibroblast fraction- and H-MSC fraction-derived naive cell fractions, Muse-enriched cells fractions, and M-clusters was compared with that in a human peripheral mononuclear cell fraction as a control. As a result, fluctuations in expression patterns of some genes were observed in naive cell fractions, Muse-enriched cells fractions, and M-clusters (FIG. 18).

Figure 19:
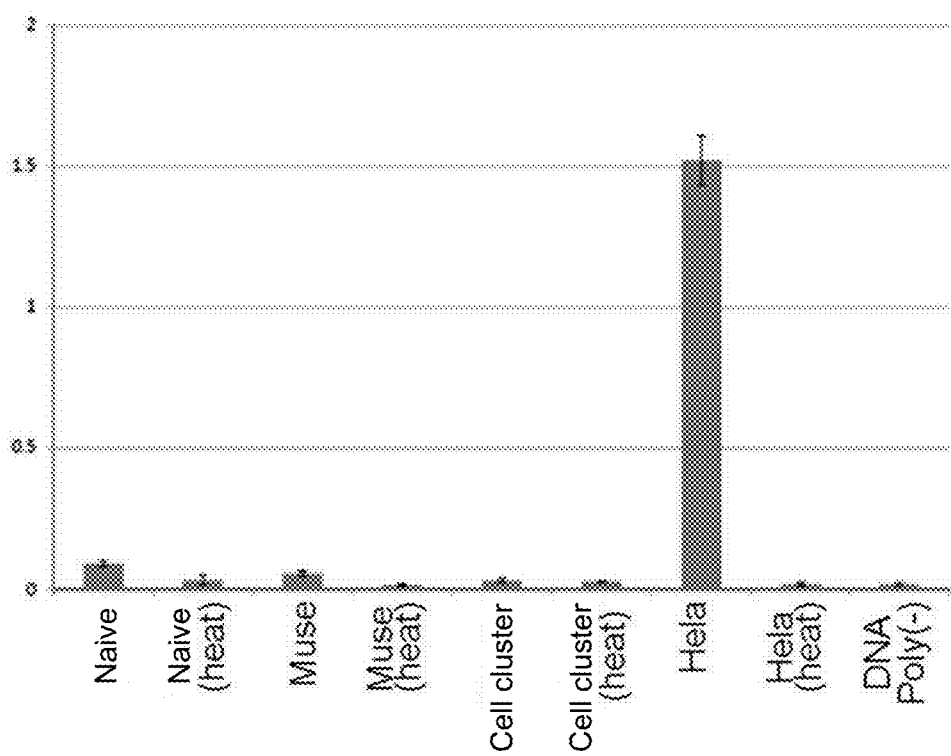
FIG. 19 shows the telomerase activity of H-MSC-derived naive cell fractions (Naive), Muse-enriched cell fractions (Muse), and M-clusters (formed in suspension day 7). Heat-inactivated samples (Heat) were used as negative controls.

Muse-enriched cell fractions and M-clusters showed low telomerase activity, suggesting that telomerase activity is not strongly related to the proliferation activity of Muse cells (FIG. 19).

G. DNA Microarray Analysis of Global Gene Expression

Figure 20:
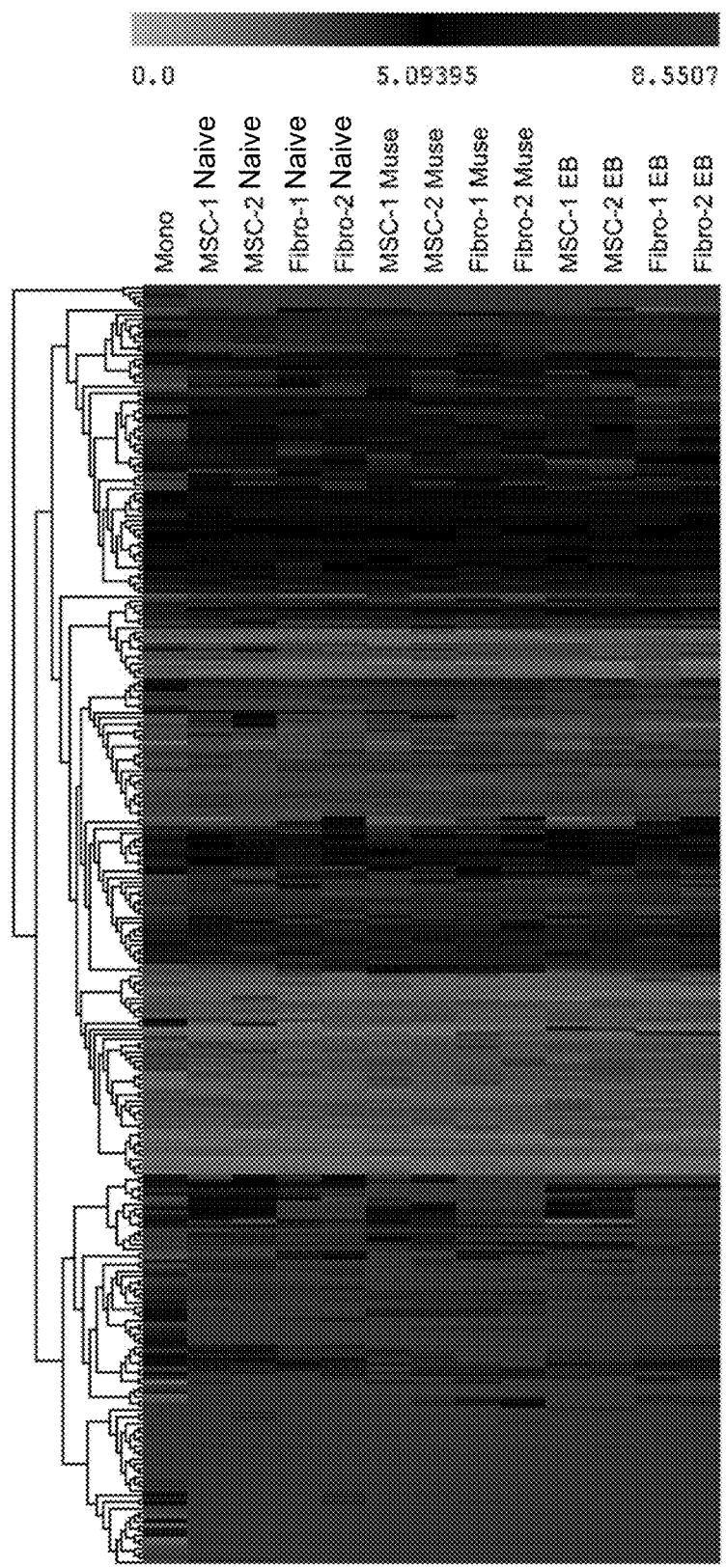
FIG. 20 shows the results of DNA microarray analysis for H-fibroblast- and H-MSC-derived naive cell fractions (referred to as "naive"), Muse-enriched cell fractions (referred to as "Muse"), and M-clusters (referred to as "EB").

Pearson correlation analysis of 108 probes was performed for human peripheral blood mononuclear cells (as negative control), naive cell fractions, and the Muse-enriched cell fractions and M-clusters from H-fibroblast fractions and H-MSC fractions (FIG. 20).

Also, odorant receptors and chemokine receptors expressed were picked up by DNA microarray analysis.

H. Muse Cells Exist In Vivo

Figure 21A:
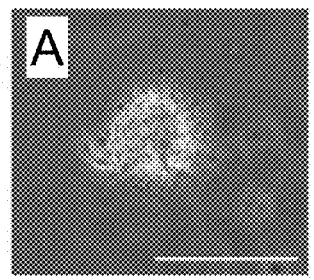
FIGS. 21A and 21B show photos showing embryoid body-like cell clusters formed by MC culture of Muse cells directly collected as SSEA-3/CD105 double positive cells from a mononuclear cell component of human bone marrow aspirate.
Figure 21B:
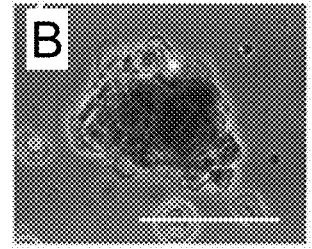
Figure 22:
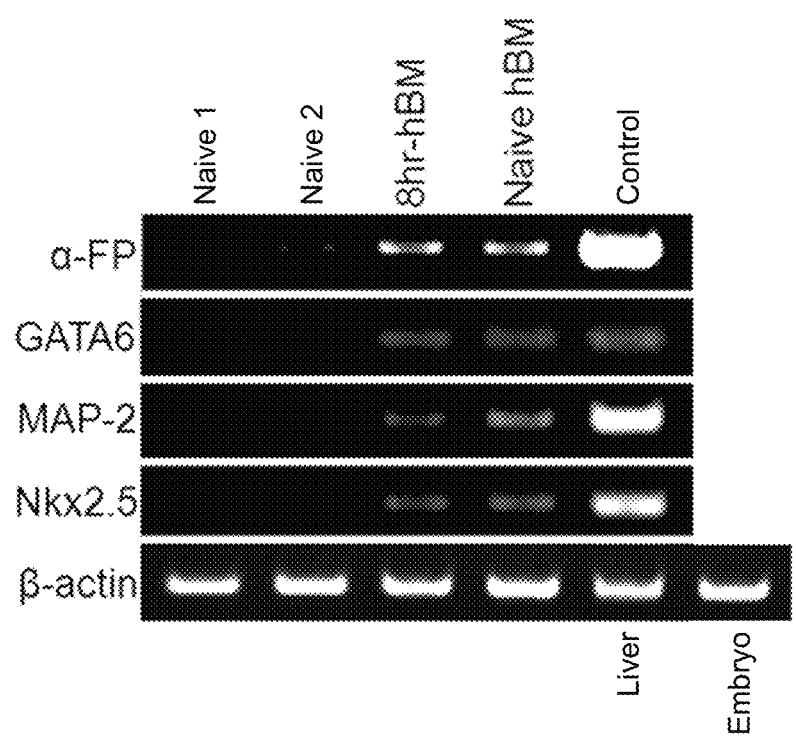
FIG. 22 shows the results of RT-PCR analysis for α-fetoprotein (α-FP), GATA6, MAP-2, and Nkx2.5 in cell fractions prepared by culturing on gelatin M-clusters formed from naive H-MSC-1 (naive 1), naive H-MSC-2 (naive 2) (both fractions were negative controls), and human bone marrow-derived mononuclear cell fractions (8 hr-hBM) subjected to 8 hours of trypsin incubation or human bone marrow-derived mononuclear cell fractions (naive hBM) not subjected to trypsin incubation, so as to induce spontaneous differentiation thereof.

The experiments described so far were performed with stable cultured cells, which may have acquired characteristics that differ from cells in situ when they are obtained from an adult body and then cultured. Hence, a possibility that Muse cells or M-clusters are artifact products cannot be denied. Therefore, we attempted to directly obtain M-clusters from a human body; that is, human bone marrow cells without culture. The mononuclear cell fractions were isolated from human bone marrow aspirates and either cultured directly on MC (naive hBM-MC) or subjected to 8 hr-LTT prior to MC culture (8 hr-hBM-MC; the survival rate of mononuclear cells after LTT was about 3.5%). After 7 days, the cultures were tested for M-cluster formation. 8 hr-hBM-MC formed M-clusters at a frequency of about 0.3%, approximately 75 times higher than that of naive hBM-MC (about 0.004%) (FIG. 21A). The M-clusters were positive for alkaline phosphatase staining (FIG. 21B). RT-PCR of cells clonally expanded from single M-clusters both from naive hBM-MC and 8 hr-hBM-MC showed expression of α-fetoprotein, GATA6, MAP-2 and Nkx2.5 (FIG. 22). These results prove that Muse cells exist in vivo in human bone marrow, that they can be enriched by 8 hr-LTT and that they can form M-clusters. It was also confirmed that, among many cell types in bone marrow, the majority of Muse cells belong to the CD105(+) mesenchymal cell fractions.

As described above, Naive hBM-MC formed M-clusters at an extremely low frequency of about 0.004% in mononuclear cell fractions directly isolated from the human bone marrow aspirate. Since it is conceivable that culturing cells changes the composition of the cell population, cells in stable culture may have a different propensity to form M-clusters compared with naive mononuclear cells isolated from the bone marrow. To confirm this possibility, a human bone marrow aspirate was cultured to collect primary MSCs and then the cells were directly subjected to MC culture. This protocol resulted in a much higher frequency of M-cluster formation of about 0.2%. When these primary MSCs were further cultured, to the $2^{nd}$ and $5^{th}$ subculture, the frequency of M-cluster formation increased by about 0.5% and about 1.0%, respectively, with respect to naive cell fractions. Consistent with this finding, about 1.2% of naive H-fibroblast fractions and H-MSC fractions formed M-clusters. These results suggest that Muse cells have high stress tolerance and can endure in vitro culture environment such as subculture procedures. Stable subcultured cell fractions thus showed a higher frequency of M-cluster formation than mononuclear cell fractions isolated directly from the bone marrow aspirate.

I. MACS Sorting

Bone marrow contains many cell types of mononuclear cells including MSCs, hematopoietic lineage cells, and endothelial cells. To determine which fraction contains the Muse cells, mononuclear cell fractions were isolated from a human bone marrow aspirate and then directly subjected to MACS sorting using antibodies against CD34, CD117 (markers for hematopoietic cells) and CD105 (marker for MSCs) (FIG. 5). The fractions were then treated with 8 hr-LTT, and the cells were grown in MC culture for 7 days. Almost no M-clusters were detected in the CD34+/CD117+ fraction, but the CD34−/CD117−/CD105+ fraction contained 50 times more cell clusters than the CD34−/CD117−/

CD105− fraction. This result suggests that the majority of Muse cells belong to the CD105(+) mesenchymal cell fraction.

The three fractions from mononuclear cells from bone marrow contained the following percentages of total cells: Fraction 1 (CD105+ fraction): 1.8%; Fraction 2 (CD34+/CD117+ fraction): 8.5%; and Fraction 3 (CD34−/CD117−/CD105− fraction): 89.7%. The frequencies of cell cluster formation in Fractions 1, 2, and 3 were 0.5%, 0% and 0.01%, respectively. The formation of cell clusters in Fraction 1 was thus about 50 times higher than that in Fraction 3.

J. FACS sorting

As an example, FACS sorting was performed using SSEA-3 as a marker.

For both H-fibroblasts and H-MSCs, SSEA-3(+) and SSEA-3(−) cells were separated by FACS sorting and subjected to single-cell suspension culture. Approximately 50%-60% of the SSEA-3(+) cells generated M-clusters, while no M-clusters were formed from SSEA-3(−) cells.

Collection of SSEA-3 (+) Cells from the Adult Human Skin

It was attempted to directly isolate Muse cells from adult human skin without incubation of cultured cells or formation of M-clusters.

Human skin from healthy donors (n=3) was obtained from BIOPREDIC International. The epidermis and fat tissues were carefully removed to separate the dermis, and the dermis was incubated with Collagenase/Dispase in α-MEM containing 10% FBS for 36 hrs at 37° C. Cells were collected by filtering digested dermis, and were subjected to centrifugation at 1500 rpm for 20 min, washed with α-MEM and incubated with 0.25% trypsin-HBSS for 5 min. Cells were further washed with FACS buffer, and incubated with SSEA-3 for collecting SSEA-3 (+) cells by cell sorting using FACS. From about 7 cm$^2$ of the skin tissue, $1.3\pm0.3\times10^4$ single cells could be finally collected. SSEA-3(+) cells accounted for 1.7±0.2% of these collected single cells.

21.0±1.7% of SSEA-3(+) cells formed M-clusters within 7 days of single-cell suspension culture by limiting dilution. The M-clusters were positive for ALP staining, and RT-PCR showed that cells expanded from a single M-cluster on gelatin-coated dishes expressed MAP-2, Brachyury, Nkx2.5, GATA6, and α-fetoprotein. These findings suggest that adult human dermis contains cells with the same properties as those of Muse cells as in the case of adult human bone marrow aspirates.

Human adult dermis contains several types of stem or progenitor cells, such as SKPs (skin-derived progenitor cells), NCSCs (neural crest stem cells), melanoblasts (MBs), perivascular cells (PCs), endothelial progenitors (EPs) and adipose-derived stem cells (ADSCs). To rule out a possibility that Muse cells are identical to one of these known stem cells, Muse cells were analyzed for expression of Snail (markers for SKPs), Slug (markers for SKPs), Sox10 (markers for NCSCs), CD271 (markers for NCSCs), Tyrp1 (markers for MBs), Dct (markers for MBs), CD117 (markers for MBs), CD146 (markers for PCs and ADSCs), NG2 (markers for PCs), CD34 (markers for EPs and ADSCs), and von Willebrand Factor (markers for EPs). None of these markers were detected in SSEA-3(+) cells by FACS or RT-PCR analysis (FIG. 33 and FIGS. 34A-34F), suggesting that Muse cells differ from these stem or progenitor cells known to be present in adult human dermis.

Figure 35A:
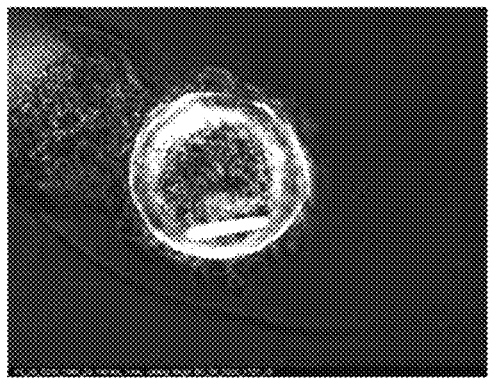
FIGS. 35A and 35B show that a Muse cell phagocytized ferrite.
Figure 35B:
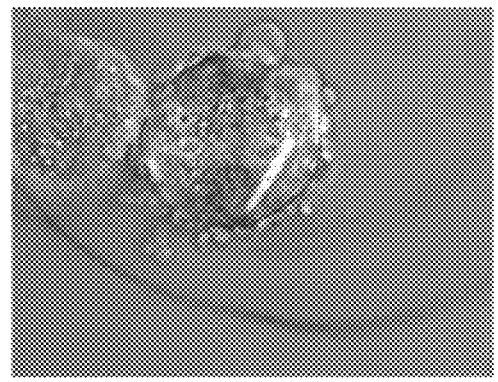
Figure 37A:
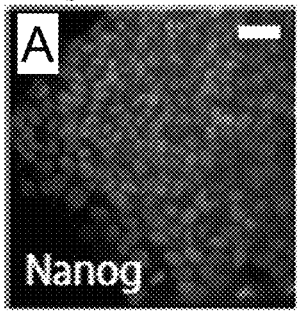
FIGS. 37A, 37B, 37C and 37D show photos showing the results of immunohistochemical analysis of Muse cell-derived iPS cells for Nonog (A), Oct3/4 (B), Sox2 (C), and Tra-1-81 (D).
Figure 37B:
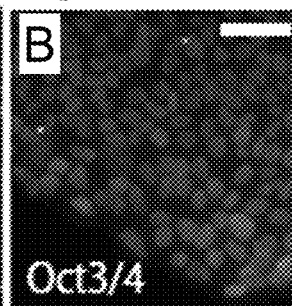
Figure 37C:
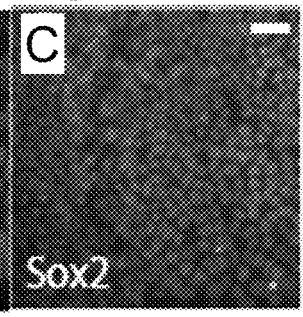
Figure 37D:
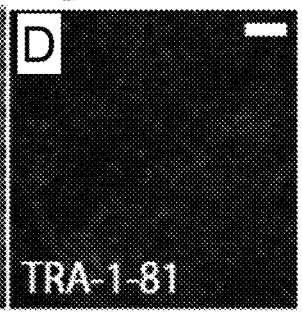

Phagocytic activity of Muse cells was determined using ferrite particles. Muse cells easily incorporated ferrite particles, suggesting that Muse cells have high phagocytic activity (FIGS. 35A and 35B).

K. Characteristic Features of Muse Cells

Figure 23:
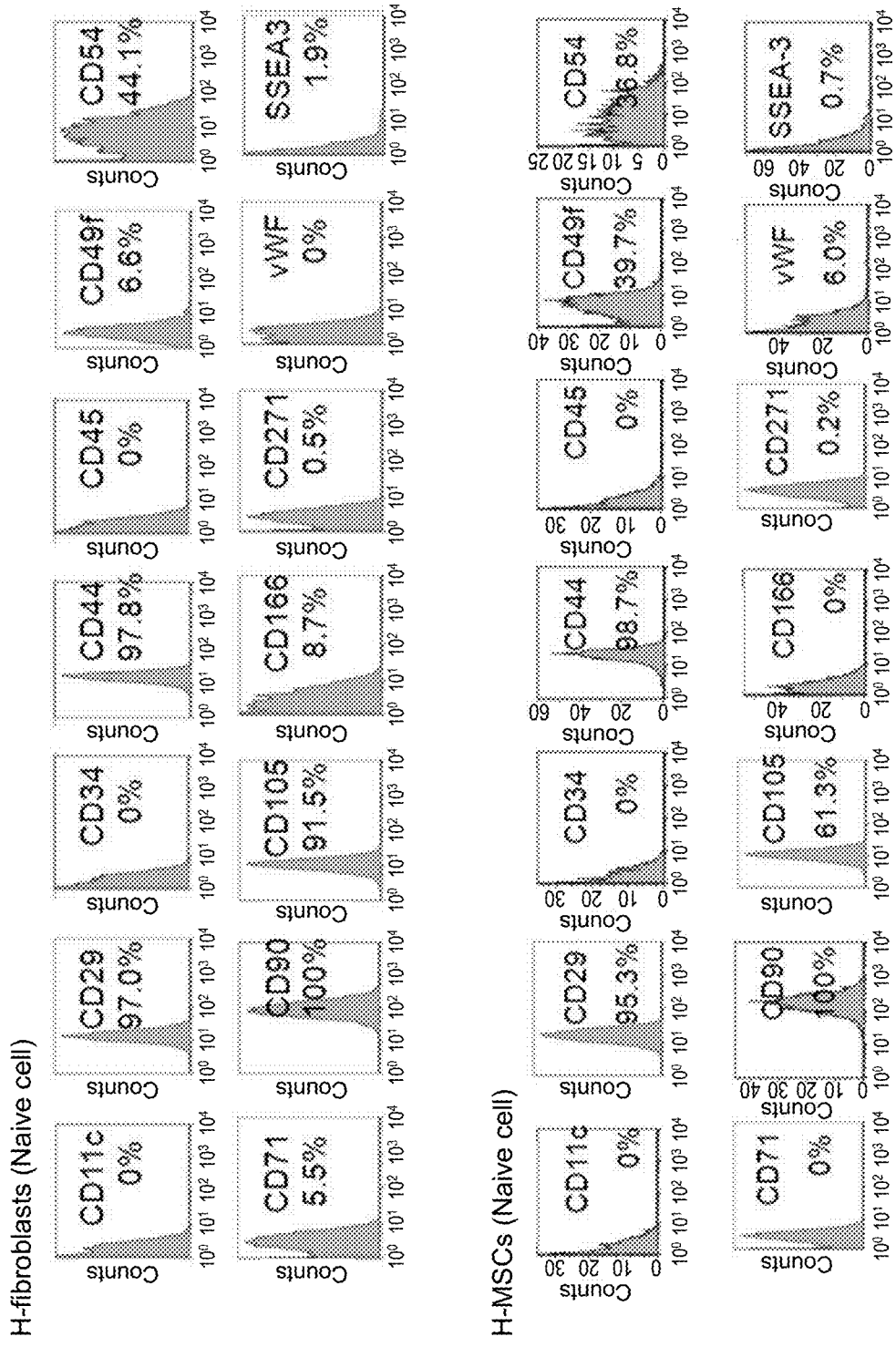
FIG. 23 shows the results of FACS analysis for H-fibroblasts (naive cells) and H-MSCs (naive cells).

FACS analysis revealed that naive H-fibroblast fractions and H-MSC fractions contained fractions positive for CD44, CD49f, CD54, CD90, and CD105 expressed in mesenchymal cells, but were negative for CD11c, CD34, CD45, CD71, CD166, CD271, and von Willebrand (vWF) factors. Both naive H-fibroblasts and H-MSCs contained about 0.7%-1.9% SSEA-3 (+) fractions (negative for CD44 and CD54) (FIG. 23).

Figure 24A:
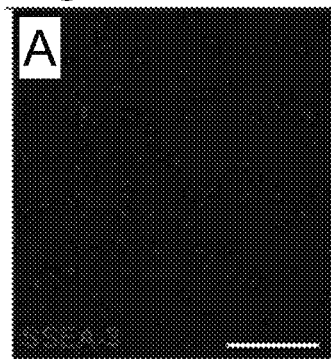
FIGS. 24A and 24B show photos showing: a stained image of SSEA-3 (+) cells (left in 24A) in naive cells; and a stained image of SSEA-3 (+) cells (right in 24B) that clonally expanded from single M-clusters from SSEA-3 (+) cells collected by FACS sorting. Each bar in this figure indicates 100 µm.
Figure 24B:
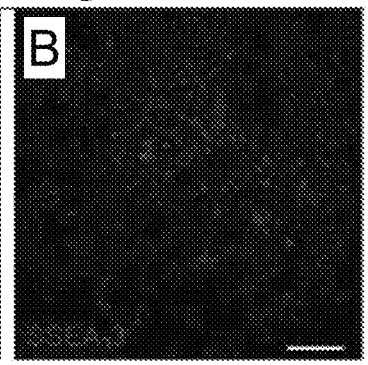
Figure 25:
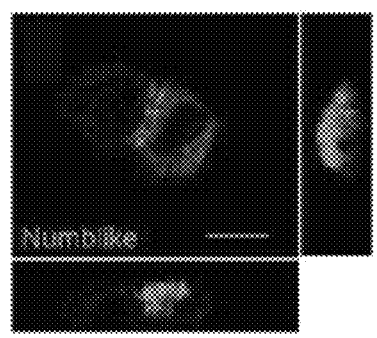
FIG. 25 shows photos of stained images showing the localization of Numb-like (green) that is a factor involved in asymmetric division during cell division of Muse cells (H-fibroblasts). Each bar in this figure indicates 100 µm.

SSEA-3 is one of the known markers for pluripotency. In naive H-fibroblast fractions and H-MCS fractions, the frequency of M-cluster formation (about 1.2%) and the frequency of Muse-enriched cell fraction formation (9%-10%) were similar to the relevant percentage of SSEA-3(+) cells (naive cell fraction: about 0.7%-0.9%; and Muse-enriched cell fraction: 7%-8.3%). Such percentage of SSEA-3(+) cells may indicate a state of Muse cells. Immunohistochemical analysis revealed that the percentage (number) of SSEA-3(+) cells in naive H-fibroblast fractions and H-MSC fractions was less than 1%. SSEA-3(+) cells were then sorted from Muse-enriched cell fractions derived from H-fibroblast fractions and H-MSC fractions and then subjected to single-cell suspension culture. As a result, 50%-60% of the SSEA-3(+) cells generated M-clusters. This result is about 6-7 times higher than that of M-cluster formation in Muse cell-enriched cell fractions and about 60 times higher than that of M-cluster formation in naive cell fractions. Meanwhile, M-cluster formation was not observed in SSEA-3 (−) cell fractions. Of note, in clonally expanded cells (3000 to 5000 cells) from a single cell cluster derived from a FACS-sorted SSEA-3(+) cell fractions, about 45% of the cells were SSEA-3(+) (FIGS. 24A and 24B). This finding suggested that asymmetric cell division is involved in M-cluster formation and that this can also be said in clonal expansion of a single M-cluster. Actually Numblike (known to be involved in asymmetric cell division) exists in only one of the two daughter cells after cell division (FIG. 25). These results suggest that asymmetric cell division is involved in the growth of Muse cells.

Figure 26A:
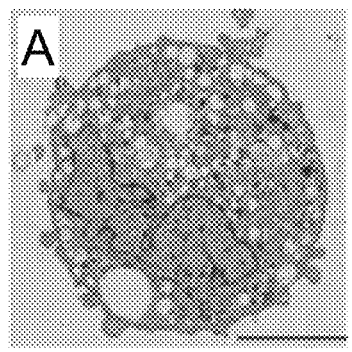
FIGS. 26A and 26B show electron micrographs showing H-fibroblast-derived SSEA-3 (−) cells (FIG. 26A) and SSEA-3 (+) cells (FIG. 26B). Each bar in this figure indicates 5 µm.
Figure 26B:
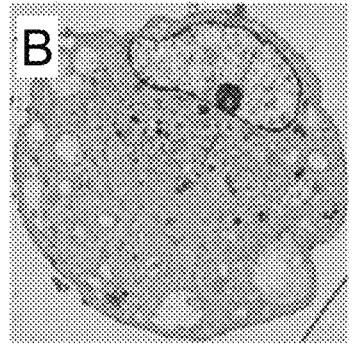

Electron microscopy revealed the presence of nuclear deformities and vacuoles in the cytoplasm in SSEA-3 (−) cells from H-fibroblast fractions and H-MSC fractions sorted after LTT, indicating cell damage. Electron microscopy did not reveal clearly recognizable morphological differences between SSEA-3 (−) and SSEA-3(+) cells (FIGS. 26A and 26B).

The importance of SSEA-3 (+) cells was also demonstrated in the transplantation experiments. When SSEA-3 (−) cell fractions were transplanted, very small number of cells were positive for the tissue markers compared to SSEA-3 (+) cell fraction transplantation.

Figure 27A:
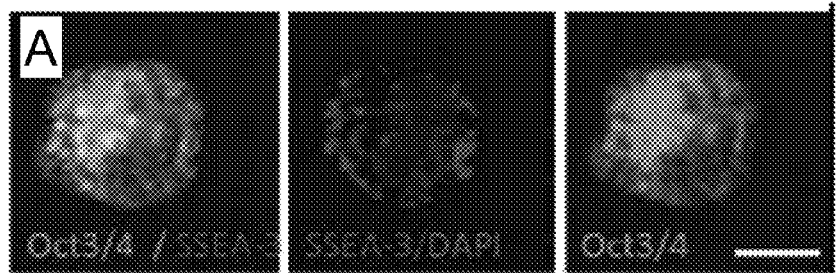
FIGS. 27A, 27B and 27C show photos of stained images showing Oct3/4 (green) (FIG. 27A), Sox2 (green) (FIG. 27B), and SSEA-3 (red) (FIG. 27C) in H-fibroblast-derived Muse cells.
Figure 27B:
Figure 27C:
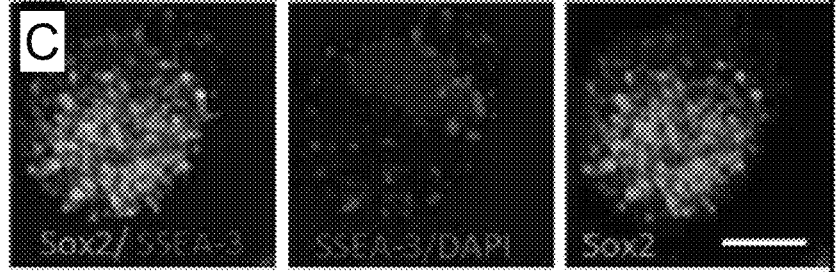

The majority of SSEA-3(+) cells in Muse-enriched cell fractions expressed both Oct3/4 and Sox2, which were detected in the cytoplasm (FIGS. 27A and 27C), and a very small number of cells expressed in the nucleus (FIG. 27B). This result indicates that SSEA-3 can be a good marker for Muse cells. In contrast, in cells in M-clusters, Oct3/4 and Sox2 predominantly localized to the nucleus (FIGS. 9B and 9F). It is possible that this difference in the intracellular localization of the two markers reflects a difference in the cell status.

The possibility remains that Muse cells are artificially induced by LTT. As described above, the majority of Muse cells exist in the bone marrow's CD105(+) cell fraction. Furthermore, SSEA-3(+) cells also showed Muse cell properties. We therefore attempted to directly obtain Muse cells from adult human bone marrow aspirates by isolating them as SSEA-3/CD105 double-positive cells. Double-positive cells, which constituted 0.025% to 0.05% of bone marrow-derived mononuclear cells, were directly subjected to single-cell suspension culture without LTT. After 7 days, 11.4%±1.2% of the cells (corresponding to 0.003% to 0.005% of the mononuclear cells) formed M-clusters, which were ALP(+). Single M-clusters were then again expanded by adherent culture to 3000 cells and subsequently subjected to single-cell suspension culture. Of these cells, 33.5%±3.1% cells formed $2^{nd}$ generation M-clusters, and RT-PCR of the cells that expanded from a single M-cluster on gelatin-coated dishes indicated the expression of α-feto-protein, GATA6, MAP-2, and Nkx2.5, suggesting that cells with properties consistent with those of Muse cells reside in adult human bone marrow.

As described above, non-stem cells were removed by exposure to stress conditions, so that stem cells could be enriched. Muse cells could be efficiently collected by LTT and the following sorting of SSEA-3 (+) cells. Muse cells expressed pluripotency markers, were positive for alkaline phosphatase staining, and formed M-clusters capable of differentiating into ectodermal, mesodermal, and endodermal cells. Also, Muse cells have no characteristics relating to tumorigenic proliferation and no telomerase activity, as revealed by measurement of the growth rate. This suggests that Muse cells have a multi-layered safety system that prevents a burst in proliferation. Such non-tumorigenic property of Muse cells was also confirmed by an experiment wherein Muse cells were injected into mouse testes. This property is convenient for maintaining the balance of bio-functions. Absence of such property may destroy a living body due to abnormal growth or dysplasia, resulting in tumorigenesis or teratoma formation.

The pluripotency of Muse cells did not become obvious in an adherent culture system, but was observed in suspension culture.

In general, it is thought that Muse cells are in a dormant state, but are activated in response to signals related to an acute crisis or to continued stressful conditions such as a severe injury, starvation, or ischemia. Upon activation, Muse cells may contribute to tissue regeneration, intercellular interactions, and thus tissue organization.

Example 2

Characterization of Muse Cells Isolated Using SSEA-3

In Example 1, SSEA-3 (+) cells were isolated from H-fibroblast and H-MSC by FACS sorting (Example 1, J). Examination in Example 1 revealed that SSEA-3 (+) cell fractions obtained by FACS had the properties of pluripotent stem cells; that is, they were Muse cells. Furthermore, in vitro differentiation ability and in vivo differentiation ability were examined using isolated SSEA-3 (+) cells and then Muse-derived iPS cells were established.

1. Examination of In Vivo Differentiation Ability by Transplantation of Cells into Damaged tissues SSEA-3 (+) Muse cells labeled with GFP (green fluorescent protein)-lentivirus were isolated and then transplanted via intravenous injection into immunodeficient mice (NOG mice) with damaged spinal cord (Crush injury of spinal cord), damaged liver (intraperitoneal injection of $CCl_4$, fulminant hepatitis model), or damaged gastrocnemius (muscle) (cardiotoxin injection). Human skin cell-derived Muse cells were labeled with GFP (green fluorescent protein)-lentivirus (Hayase M et al., J Cereb Blood Flow Metab. 29(8): 1409-20, 2009) and then it was confirmed using GFP that M-clusters were derived from the labeled cells. Crush injury of spinal cord was performed at the level of Th9 (Farooque M et al., Acta Neuropathol., 100; 13-22, 2000) for NOG mice. Cardiotoxin was injected into the gastrocnemius (muscle) of the NOG mice to induce muscle degeneration. Carbon tetrachloride was administered to NOG mice by peritoneal injection to induce liver degeneration. $1\times10^5$ Muse cells were transplanted by intravenous injection 2 days after for the muscle and liver and 7 days after for the spinal cord. Six mice were used for each condition. Intact mice that received intravenous injection of GFP-labeled MEC fraction were used as controls. At 3 or 4 weeks after transplantation, mice were fixed with 4% paraformaldehyde and then subjected to immunohistochemical analysis and confocal laser microscopic observation.

Figure 29:
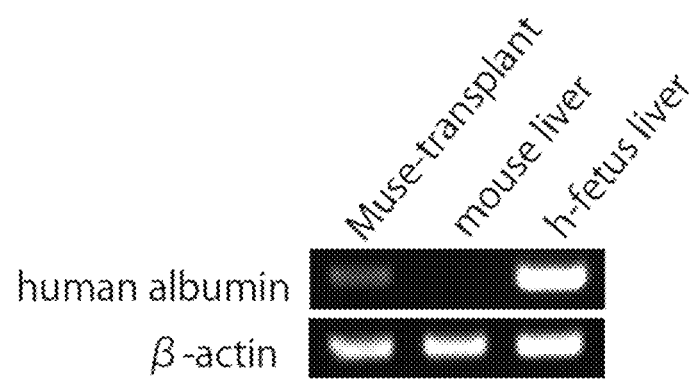
FIG. 29 shows photos showing the expression of human albumin in the liver into which SSEA-3 (+) Muse cells were transplanted, as examined by RT-PCR.
Figure 30:
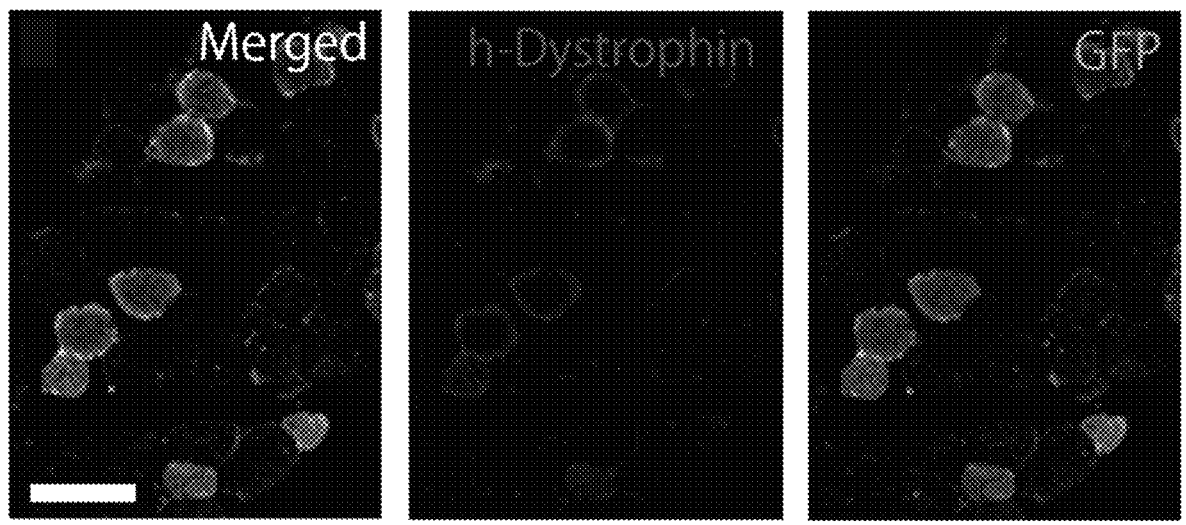
FIG. 30 shows photos showing the differentiation of GFP-labeled SSEA-3 (+) Muse cell fractions in damaged tissue of severely immunodeficient mice (Nog mice). Specifically, the photos show GFP (+) cells of muscle (3 weeks later) expressing human dystrophin (red) in the damaged mice skeletal muscle.

After 4 weeks, in mice with spinal cord injury, it was found that: cells positive for GFP and human Golgi complex expressed neurofilaments (FIGS. 28A and 28B); and that in mice with liver damage, cells positive for GFP and human Golgi complex (in regenerated liver) expressed human albumin (FIG. 28C). RT-PCR further confirmed the expression of human albumin in Muse cell-transplanted NOG mice liver (FIG. 29). GFP(+)cells injected into the regenerating muscle and at 3 weeks expressed human dystrophin (FIG. 30). In contrast to these results, transplantation of SSEA-3 (−) human dermal fibroblast fractions resulted in a significantly smaller number of integrated cells and fewer cells that were positive for the respective tissue markers. These findings suggest that Muse cells have an ability to integrate into damaged tissues and also to differentiate in vivo into ectodermal-, endodermal-, and mesodermal-lineage cells.

2. Differentiation of Expanded Cells Derived from M-Cluster Generated from Single Muse Cells It was examined whether an induction system is effective for regulation of differentiation of Muse cells. Single SSEA-3(+)-Muse cell-derived M-clusters were transferred individually to adherent culture for expansion. Expanded cells derived from a single Muse cell were collected, divided into four fractions, and then each subjected to neural, osteocytes, adipocytes and hepatocyte inductions (n=5).

For neural induction, cells at a density of $1.0\times10^5$ cells/ml were cultured in NEUROBASA1 medium (Gibco) supplied with B-27 Supplement in poly-HEMA coated dish and cultured for 7 days for sphere formation. For differentiation, spheres were transferred onto poly-L-Lysin-coated glass, and incubated in 2% FBS supplied with 25 ng/ml FGF and 25 ng/ml BDNF for 10 days.

For osteocyte induction, cells at a density of $4.2\times10^3$ cells/cm² were incubated with osteocyte induction medium of Human Mesenchymal Stem Cell Functional Identification Kit (R&D Systems, SC-006) for 14 days.

For adipocyte induction, cells at a density of $2.1\times10^4$ cells/cm² were incubated with adipocytes induction medium of the human mesenchymal stem cell functional identification kit (R&D Systems) and incubated for 14 days.

For hepatocyte induction, cells at a density of $2.0\times10^4$ cells/cm² were incubated with DMEM (+10% FBS, 10×ITS (GIBCO) supplied with 10 nM dexamethasone and 100 ng/ml HGF, 50 ng/ml FGF4) on collagen-coated dish for 14 days.

Figure 31A:
FIGS. 31A, 31B, 31C, 31D, 31E, 31F, 31G, 31H, 31I and 31J show photos showing the differentiation of cells grown from M-clusters formed from single Muse cells.
Figure 31B:
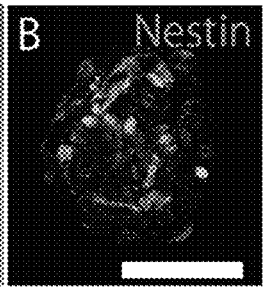
Figure 31C:
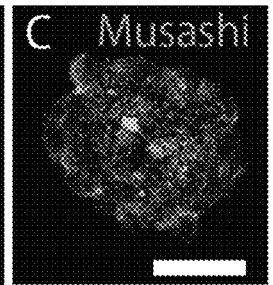
Figure 31D:
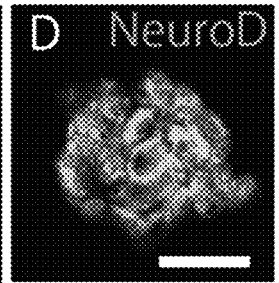
Figure 31E:
Figure 31F:
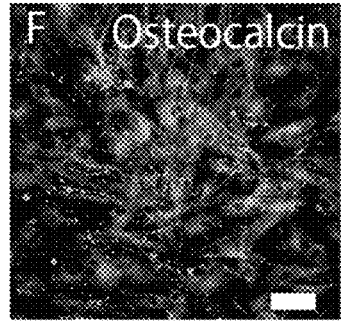
Figure 31G:
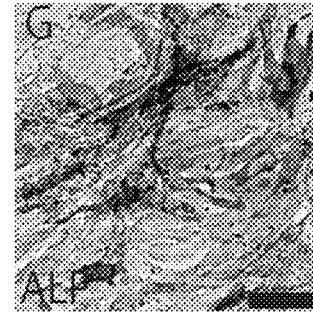

Neural induction generated spheres containing cells positive for neural stem cell markers nestin, Musashi and NeuroD (FIGS. 31A-D), which further differentiated into MAP-2- or GFAP-positive cells when cultured in differentiation medium (FIG. 31E; 89±5.7% positive either for MAP-2 or GFAP). Osteocyte induction produced cells positive for osteocalcin (97±3.5%) and alkaline phosphatase (FIGS.

Figure 31H:
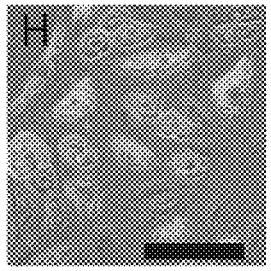
Figure 31I:
Figure 31J:
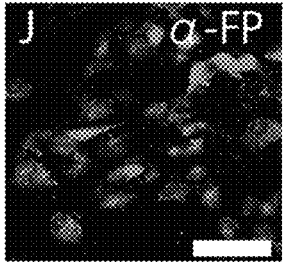
Figure 32:
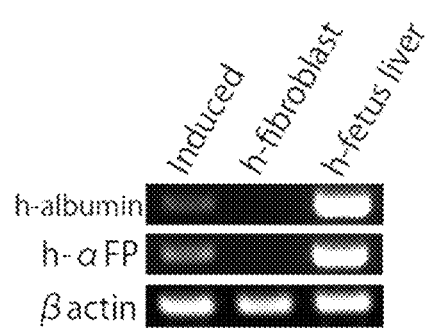
FIG. 32 shows photos showing the expression of human albumin and human α-fetoprotein in cells induced by hepatocyte induction from Muse cells, as examined by RT-PCR. h-fibroblast is negative control and h-fetus liver is positive control.
Figure 33:
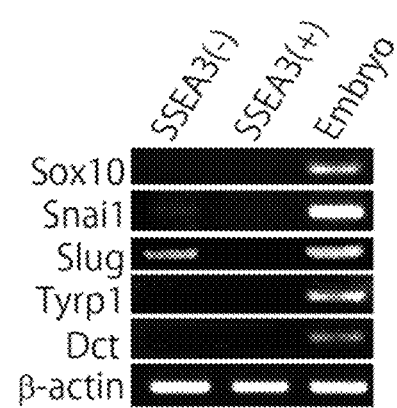
FIG. 33 shows photos showing the expression of Sox10, Snail1, Slug, Tyrp1, and Dct in SSEA-3 (+) Muse cells obtained from H-fibroblasts, as examined by RT-PCR. "Embryo" is positive control.

31F-G). Adipocyte differentiation produced cells with lipid droplets that stained with oil red (90±4.9%) (FIGS. 31H-I). Hepatocyte induction generated cells positive for human α-fetoprotein (FIG. 31J; 87±7.6%), and RT-PCR confirmed the expression of human albumin and α-fetoprotein (FIG. 32). These results demonstrate that Muse cells can be regulated (via induction) to differentiate into cells of three lineages with very high efficiency.

3. Establishment of Muse-Derived iPS Cells (Muse-iPSC)

iPS cells are prepared by introduction of Oct3/4 gene, Sox2 gene, Klf4 gene, c-Myc gene, Nanog gene, and Lin28 gene, for example. Muse cells have properties analogous to iPS cells in that they express pluripotency markers and can differentiate into ectodermal, mesodermal, and endodermal cells. It was examined if Muse cells could be good materials for iPS cells.

A method employed for this purpose is as follows.

Four factors (Nanog, Oct3/4, KLF4, and c-Myc) were introduced into SSEA-3(+) cells and SSEA-3 (−) cells from H-fibroblast fractions using retroviral vectors according to the description of Takahashi et al., Cell, 131, 861-872 (2007) and then cultured. The method is specifically described as follows.

Establishment of Plasmid

The open reading frames of human Oct3/4, Sox2, Klf4, and c-Myc were inserted into the pMXs retroviral vectors (Cell Biolabs).

Infection with Retrovirus and Establishment of iPS Cells

PLAT-A cells were seeded at a density of $5\times10^6$ cells per 100-mm dish and then cultured overnight. On the next day, transfection was performed using Fugene HD. At 24 hours after transfection, medium exchange was performed. Supernatants were collected after 3 days and then filtered through a 0.45-μm filter. Polybrene (4 μg/ml) was then added. H-fibroblast fraction-derived SSEA-3(+) and (−) cells seeded at a density of $1\times10^5$ cells per 60-mm dish were infected with a virus solution. 24 hours later, the medium was exchanged with new medium containing no virus. Cells were removed using trypsin on day 4 after viral infection and then seeded on MEF (feeder cells) at a density of $3\times10^4$ cells. On the next day, the medium was exchanged with Primate ES medium supplemented with 4 ng/ml bFGF. After 2 days, medium exchange was performed once every other day. After 30 days, colonies were picked up and then seeded over a 24-well plate.

PCR Analysis

RNA was purified using an RNeasy mini kit (QIAGEN). RNA (500 ng) was reverse transcribed using SuperScriptII. Endogenous Oct, Sox2, Klf4, Myc, and Nanog primers, PCR conditions, and the like are as described in Takahashi et al., Cell, 131, 861-872 (2007).

In Vitro iPS Cell Differentiation iPS cells were collected using collagenase. Cell clusters were placed on dishes coated with Poly-HEMA and then cultured in DMEM/F12 medium containing 20% Knockout serum replacement (Invitrogen), 2 mM L-Glutamine, $1\times10^{-4}$M nonessential amino acid, $1\times10^{-4}$M 2-mercaptoethanol (Nacalai), and 0.5% Penicillin/Streptomycin. Medium was exchanged once every other day. 7 days later, embryoid bodies were seeded on gelatin-coated dishes, followed by 1 week of culture in the same medium.

Formation of Teratomas iPS cells in a 60-mm dish were treated with a Rock inhibitor, collected using Accutase (registered trademark) in a tube, subjected to centrifugation, and then suspended in PBS. These cells were injected into the testis of an NOG mouse (registered trademark) (Central Institute for Experimental Animals). After 12 weeks, the resultants were fixed with 4% paraformaldehyde. Paraffin sections were subjected to HE (Hematoxylin & Eosin) staining.

The following results were obtained.

Figure 38:
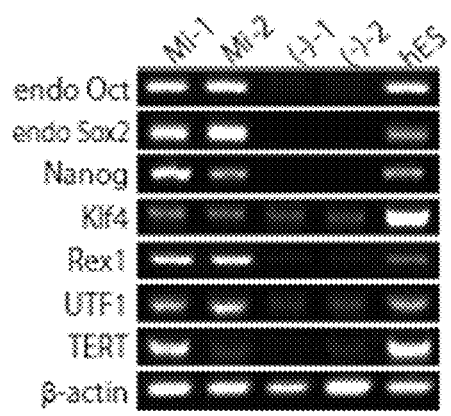
FIG. 38 shows photos showing the expression of pluripotency markers in colonies ((−)-1 and (−)-2) from Muse-derived iPS cells (Mi-1 and Mi-2) and SSEA-3 (−) cell-derived non-iPS colonies, as examined by RT-PCR.
Figure 39:
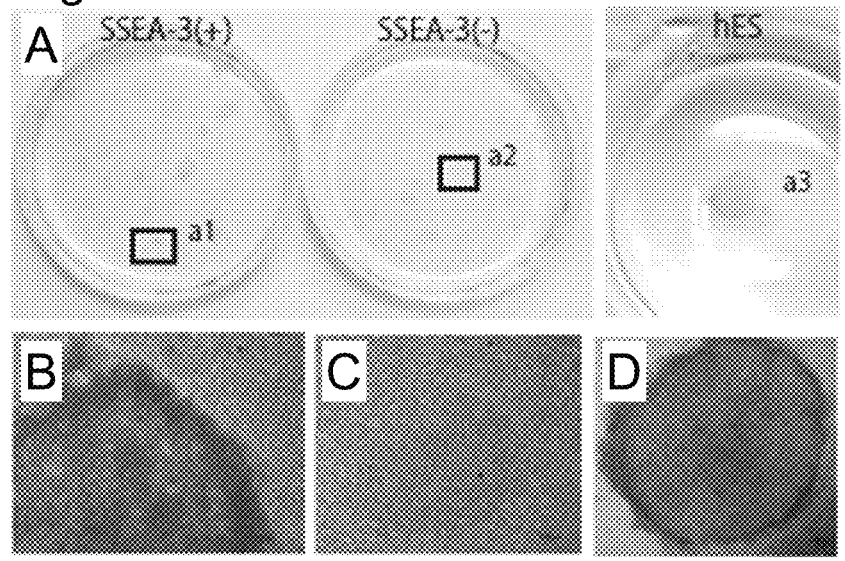
FIGS. 39A, 39B, 39C and 39D show photos showing the results of Tra-1-81 immunostaining of colonies formed by SSEA-3 (+) and (−) cells on day 30 after culturing on MEF feeder cells following introduction of Oct3/4, Sox2, Klf4, and c-Myc with retrovirus. Human ES cells were used as controls. Colonies (a1) from SSEA-3 (+) cells and human ES cells (a2) were positive for Tra-1-81, but all colonies from SSEA-3 (−) cells were negative for the same.

Four factors, Nanog, Oct3/4, KLF4 and c-Myc were introduced into H-fibroblast fraction-derived SSEA-3(+) and (−) cells using retroviral vectors according to the method described by Takahashi et al, Cell, 131, 861-872 (2007). Cells were seeded again on MEF after 5 days, and then cultured. Just before colony pickup; that is, on day 30 of culture on MEF, all the generated colonies in SSEA-3 (−) cells were non-ES cell-like colonies and none of them were positive for Tra-1-80 (ES cell marker as well as reliable iPS cell marker). In contrast, many SSEA-3(+) cells formed colonies about eightfold the number of colonies formed by SSEA-3(−) cell fractions, which were positive for Tra-1-80. Importantly, genes tightly related to pluripotency, such as Nanog and Sox2 were all negative in SSEA-3 (−) cells (all colonies and cells not forming colonies were collected) even immediately before colony pickup on day 30 on MEF, as determined by RT-PCR. Meanwhile, SSEA-3(+) cells showed up-regulation of endogenous Oct3/4, KLF4, and Rex1 and expressed Nanog and Sox2. As expected, SSEA-3(+) cells were subjected to colony pickup and then transferred onto new MEF (feeder cells), iPS cells could be successfully generated at efficiency about 30 times higher than that of naive H-fibroblast fraction cells. These iPS cells exhibited up-regulation or new appearance of Tra-1-60, Tra-a-80, Rex1, UTF-1, telomerase reverse transcriptase (TERT) and factors expressed in human ES cells, as revealed by immunocytochemistry, RT-PCR, and Q-PCR (FIGS. 36A-36F and FIG. 38). Furthermore, Nanog, Oct3/4, Sox 2, and TRA-1-81 were expressed in the thus obtained Muse cell-derived iPS cells (FIGS. 37A-37D). RT-PCR revealed that Nanog, Oct3/4, and Sox 2 were expressed in Muse cell-derived iPS cells, but not expressed in SSEA-3 (−) cell-derived colonies (FIG. 38).

Figure 40:
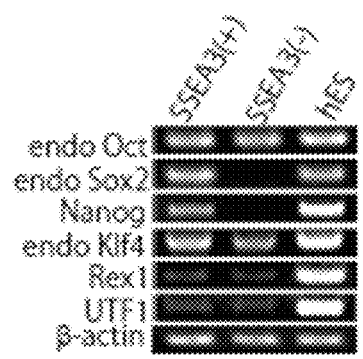
FIG. 40 shows photos showing the expression of pluripotency markers (endogenous Oct3/4 (endo Oct), endogenous Sox2 (endo Sox2), Nanog, endogenous Klf4 (endo Klf4), Rex1, and UTF1) for SSEA-3 (+) and (−) cells at a stage after 30 days of culture on MEF as in FIG. 39. In the SSEA-3 (−) cell fraction, no Sox2 and Nanog signals were observed.
Figure 42A:
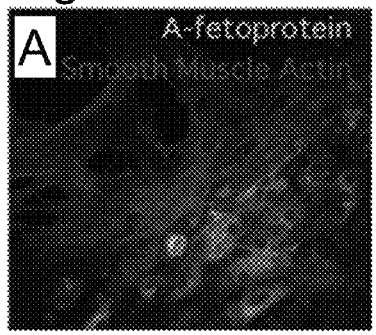
FIGS. 42A and 42B show photos showing in vitro differentiation of iPS cells induced from dermal fibroblast-derived Muse cells.
Figure 42B:
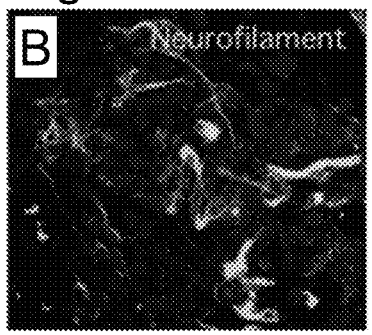
Figure 43:
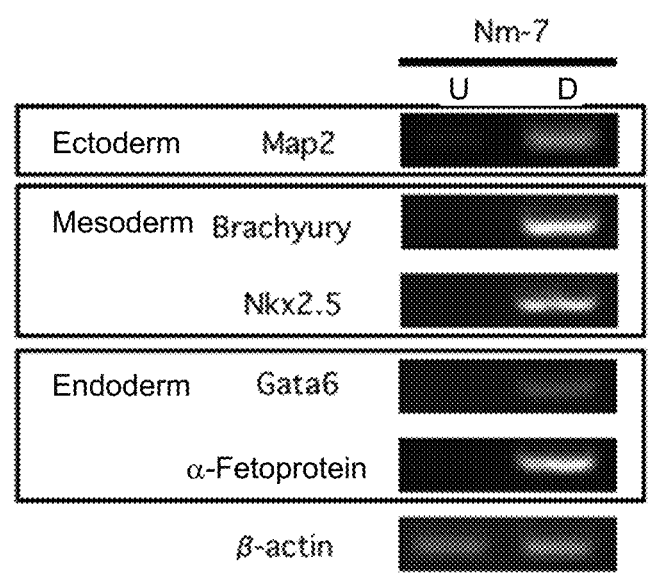
FIG. 43 shows the results of RT-PCR analysis for in vitro differentiation of iPS cells induced from dermal fibroblast-derived Muse cells.
Figure 44A:
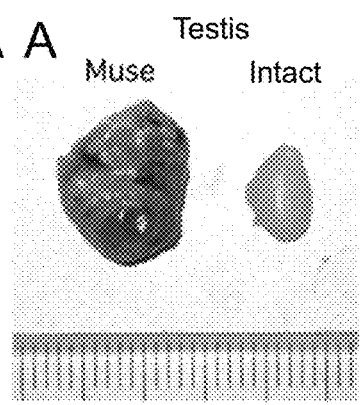
Figure 44B:
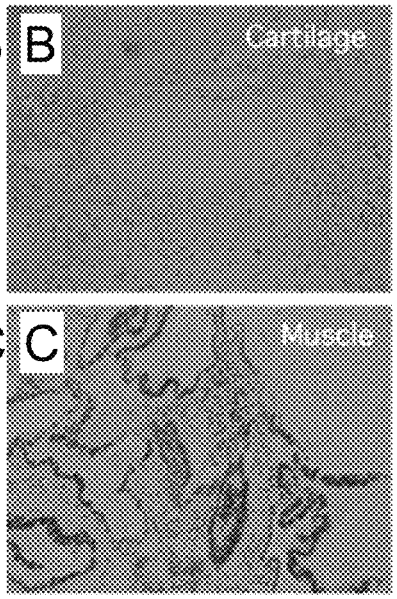
Figure 44C:
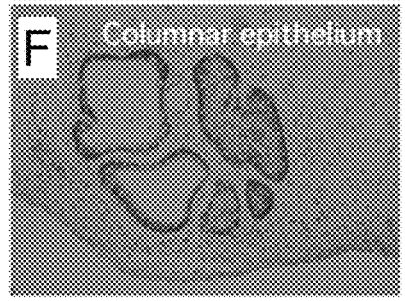
Figure 44D:
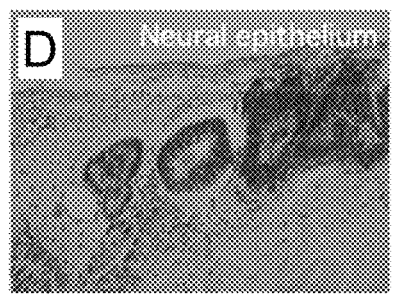
Figure 44E:
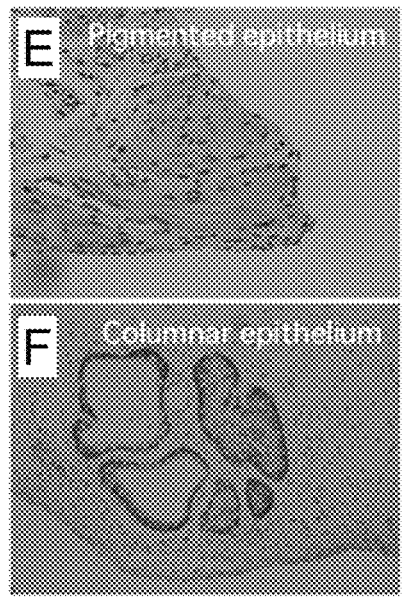

The efficiencies for transduction of Oct3/4 gene, Sox 2 gene, Klf4 gene, and c-Myc gene were almost identical for the SSEA-3(+) and SSEA-3(−) cell fractions. Transduced cells with above four factors were then transferred onto and cultured on mouse feeder cells at a density of $1\times10^5$ cells per dish. The generation of colonies were observed in both fractions, but SSEA-3(+) cell fractions formed seven times more colonies than the SSEA-3 (−) cells. Furthermore, in contrast to those derived from the SSEA-3(+) cell fractions, none of the colonies derived from the SSEA-3 (−) cell fractions were found to be positive for the human pluripotent stem cell marker TRA-1-81 even on day 30 of culture immediately before colony pickup (FIGS. 39A-39D). RT-PCR revealed that endogenous Sox2 and Nanog were only expressed in SSEA-3(+) cell-derived fractions but not in SSEA-3(−) cell fractions (FIG. 40).

All colonies generated from SSEA-3(+) and SSEA-3 (−) cell fractions were picked and passaged in individual wells to establish iPS cell lines. After 3 passages, all colonies exhibiting human ES cell-like morphology (flat colonies) were individually subjected to RT-PCR (FIGS. 41A and B). Colonies expressing all three factors (endogenous Oct3/4, endogenous Sox2 and Nanog) were counted iPS colonies. This analysis revealed that only colonies originating from SSEA-3(+)cells generated iPS cells and the efficiency was 0.03%, while none of the colonies originating from SSEA-3 (−) cells generated iPS cells (FIGS. 41C and D).

Furthermore, iPS cells established from Muse cells differentiated into ectodermal, mesodermal, and endodermal cells, and formed teratomas in mice testes (FIGS. 42A and 42B, FIG. 43 and FIGS. 44A-44F).

The proliferation activity of Muse cells was not so high in terms of growth rate and telomerase activity. Consistently, while Muse cells differentiated into triploblastic cells in the mice testes, they did not develop into teratomas. This may be reasonable because if Muse cells are maintained in adult human tissue such as in skin and bone marrow, their proliferation should be strictly regulated, otherwise they would easily develop into tumors in virtually every part of the body. Moreover, even pluripotent cells do not always show teratoma formation since epiblast stem cells cultured under certain conditions were demonstrated not to form teratomas in mice testes (Chou et al., Cell, 135, 449-461 (2008)). As Muse cells originally showed some of the characteristics of pluripotent cells such as pluripotency marker expression and their differentiation ability, it is suggested that Muse cells could easily become iPS cells solely by an elevation of proliferative activity and formed teratoma in the mice testes. The induction mechanism of iPS is not yet clarified, but procurement of tumorigenic proliferation in Muse cells among mesenchymal cell fraction might be one of the possibilities.

iPS cells could be established at efficiency of about 0.001% from naive human dermal fibroblast fractions. This agrees with the report of K. Takahashi et al., Cell 131, 861 (2007). Therefore, iPS cell preparation efficiency from SSEA-3 (+) cells was 30 times higher than that from naive fibroblasts. This suggests that Muse cells mainly contribute to iPS cell generation.

Immunohistochemical analysis and RT-PCR analysis of embryoid bodies that developed from Muse-derived iPS cells showed that cells differentiated into ectodermal cells expressing neurofilament and MAP-2, mesodermal cells expressing SMA, Brachyury and Nkx2.5, and endodermal cells expressing α-fetoprotein and GATA-6 in vitro. Furthermore, injection of Muse-derived iPS cells into testes of immunodeficient mice resulted in teratoma formation. In contrast, testes injected with M-clusters did not develop teratomas for up to 6 months, and most were not significantly larger than control testes that were injected with inactivated MEFs.

Figure 45:
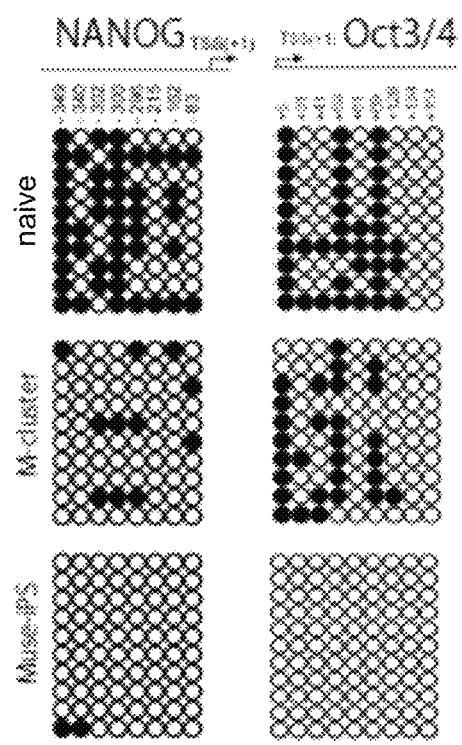
FIG. 45 shows the results of bisulfite (hydrogensulfite) sequencing in Muse cells for the Nanog gene and the Oct3/4 gene of naive state, M-clusters, and Muse-derived iPS cells. The numerical value in each column indicates the position of CpG downstream of the transcription start site (TSS). An open circle indicates unmethylated cytosine and a filled circle indicates methylated cytosine.

M-clusters and Muse-derived iPS cells were subjected to quantitative-PCR (Q-PCR). The results are shown in FIGS. 46 and 47. The expression patterns of genes related to cell cycle regulation differed substantially. Genes related to cell cycle progression were mostly down-regulated in M-clusters but up-regulated in Muse-derived iPS cells. Expression of genes related to pluripotency and an undifferentiated cell state were similar in M-clusters and Muse-derived iPS cells, but the expression levels of Nanog, Oct3/4 and Sox2 were much lower in M-clusters than in Muse-derived iPS cells. Furthermore, cytosine guanine dinucleotides (CpGs) in the promoter regions of Nanog and Oct3/4 genes were less methylated in Muse-derived iPS cells than in M-clusters, and the promoter region of Nanog gene showed a lower CpG methylation level in M-clusters than in naive SSEA-3 (−) cell fractions (FIG. 45). This result may partly explain the differences in the expression level of pluripotency markers between Muse cells and Muse-derived iPS cells.

Example 3

Pluripotent Stem Cell Derived from Fat Tissue of a Living Body Materials and Methods 1. Cell Materials Two cell materials were used. One is cell which is commercial available as a mesenchymal cell derived from human adipose tissue and the other is a mesenchymal cell established from the primary cultured cell of human subcutaneous adipose tissue by the present inventors. The commercial available cell was the Human Adipose-Derived Stem Cell (HADSC) purchased from Lonza (Lot. 7F4309, 7F4089 and 7F4205). Cells were cultured in Dulbecco's modified Eagle medium-High Glucose [DMEM, liquid (1×); Invitrogen Cat. 11965-092] 15% (vol/vol) FBS [ES cell grade; HyClone], 0.1 mg/mL Kanamycin sulfate [liquid (100×); Invitrogen Cat. 15160-054] at 37° C.

The mesenchymal cell derived from human subcutaneous adipose tissue (in the following text, they are called "established cells") was established using adipose tissue supplied by Tohoku University hospital, Japan using a partially modified method of Estes B T et al. et al. (Nat Protoc. 2010 Jul.: 5(7):1294-1311).

Firstly, subcutaneous adipose tissue obtained aseptically was cut out to pieces. Enzyme solution was prepared by adding 1 mg/mL colagenase Type I [100 mg; Worthington Biochemical Cat. LS004194], 1% (wt/vol) BSA [nacalai Cat. 15111-45] into Phosphate-Buffered Saline [PBS, magnesia chloride and calcium chloride free]. The cut adipose tissue and the enzyme solution were mixed in equal amount in an centrifuging tube and extracellular matrix was digested by reacting the mixture for two hours at 37° C. Two hours later, the mixture was centrifuged for 5 minutes at 300 g and liquid phase between precipitate and supernatant was aspirated and undigested extracellular matrix was removed from the precipitate and supernatant using 100 μl cell strainer. Then, DMEM [15% (vol/vol) FBS, 0.1 mg/mL kanamycin sulfate] was added and the solution was centrifuged for 5 minutes at 300 g and the supernatant was removed. The precipitate was suspended to be seeded. Twenty four hours later from the inoculation, culture medium was replaced.

For the commercially available cell and the established cell, culture medium was replaced every two days. When the cultured reached to 90% confluent, the cells were subcultured at the ratio of 1:2. For mouse ES cells, 15% (vol/vol) FBS [ES cell grade; HyClone], 0.1 mg/mL kanamycin sulfate [liquid (100×); Invitrogen Cat. 15160-054], 0.1 mM MEM Non-Essential Amino Acids Solution [NEAA, liquid 10 mM (100×); Invitrogen Cat. 11140-050], Sodium pyruvic acid solution 1 mM [SP, liquid 100 mM (100×); Invitrogen Cat. 11360-070], 1000 U/mL Leukemia Inhibitory Factor [LIF, ESGRO], 100 μM 2-mercaptoethanol was used and MEF (mouse embryonic feeder) treated with mytomycin was used as feeder cells. MEF prepared from a 12.5-day old C57BL/6 mouse fetus.

2. FACS

Figure 49A:
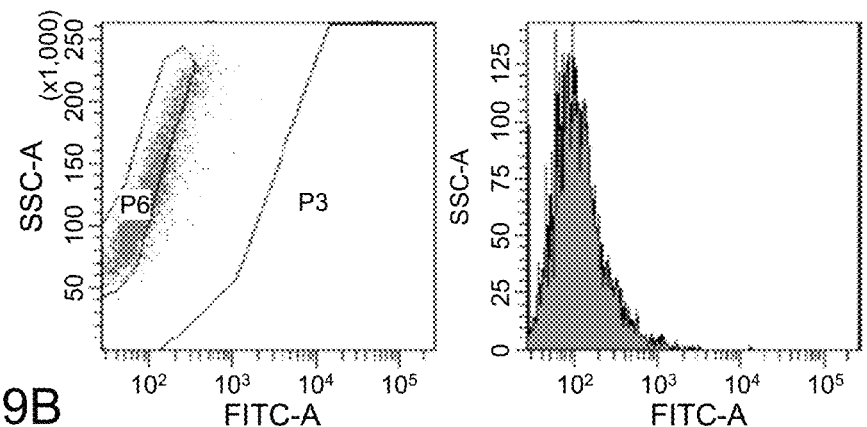
FIGS. 49A, 49B and 49C show the results of FACS analysis using anti-SSEA-3 antibody in human adipose tissue-derived mesenchymal stem cells. A: No stain, B: Second antibody only, C: SSEA-3 staining.
Figure 49B:
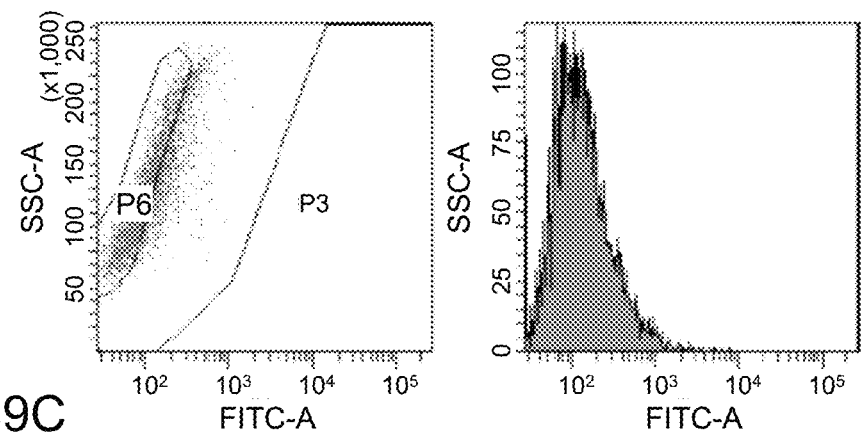
Figure 49C:
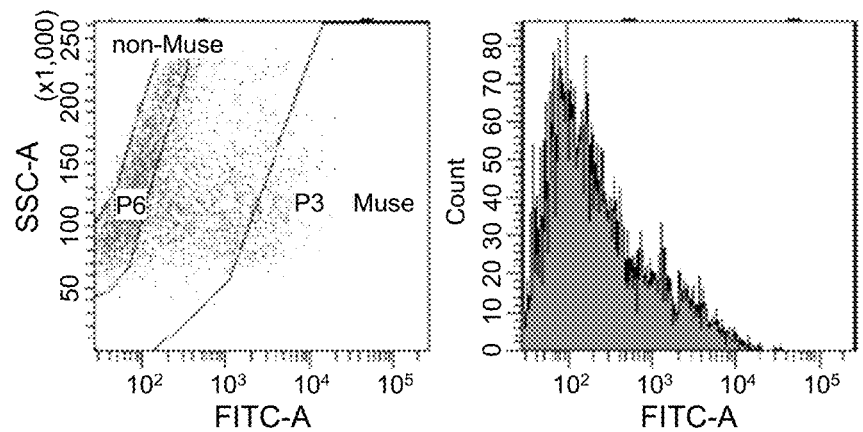

FACS analysis for the commercial available human mesenchymal cell derived from human adipose tissue and mesenchymal cell established from the primary cultured cell of human subcutaneous adipose tissue was carried out. Cells were used for FACS analysis when the culture reached to 100% confluent. Firstly, medium was removed from a dish and 3 mL of trypsin-EDTA was added to the dish and expanded to all cells. Then, the cells were incubated for 10 minutes at 37° C. Confirming that the cells were detached from the dish with certainty, 1 mL of FBS was added and put cells into single cell by pipetting. Then, cells were recovered and counted. Cells were suspended such that the cell density became one million cells per 100 μl. Cells were incubated with 10% inactivated human serum for 20 minutes on ice and FcR blocking was carried out. Then, the cells were incubated with anti-SSEA-3 antibody (1:50, Millipore) and FITC-labeled anti-rat IgM antibody (1:100, Jackson Immunoresearch) used as a primary antibody and a secondary antibody, respectively, to be stained. After the staining, analysis and sorting were carried out using Special Order Research Products FACS Arial I (Becton Dickinson). FIGS. 49A-49C show the results. Peaks of the sample to which the secondary antibody (FIG. 49B) only was added and the sample which was SSEA-3 stained (FIG. 49C) were adjusted such that the position of the peaks was the same with that of non-staining sample (FIG. 49A). Then, cell fraction showing almost the same FITC intensity as non-staining sample was recovered as non-Muse cells (P6 area in FIGS. 49A-49C) and cell fraction showing the stronger FITC intensity than the sample with the secondary antibody only was recovered as Muse cells (P3 area in FIGS. 49A-49C).

3. Single Cell Suspension Culture

Cells which were sorted by FACS using the expression of SSEA-3 as a marker from the commercial available human mesenchymal cell derived from human adipose tissue and mesenchymal cell established from the primary cultured cell of human subcutaneous adipose tissue were stained with trypan blue and living cells were counted. Limiting dilution was performed to adjust to 1 cell/well and cells were suspended in a MEM with 15% (vol/vol) FBS and seeded in 96 well dish coated with poly-HEMA. Suspension culture was carried out for 7 to 10 days and the formation rate of M-clusters was counted.

4. Differentiation of M-Cluster In Vitro

M-clusters which had been cultured for 7 to 10 days in the single cell suspension culture of 3. above were transferred to 24 well dish coated with 0.1% gelatin into which 300 μl of α MEM [15% (vol/vol) FBS)] was added such that number of M-clusters was adjusted to one M-cluster/well. Several hours later, 200 μl of culture medium was added. After one or two week—culture, cells were analyzed by immunocytohistochemistry and RT-PCR.

5. Immunocytohistochemistry

M-cluster obtained in 3. above was fixed by 4% (vol/vol) paraformaldehyde/0.01M PBS and embedded with O.C.T. compound to prepare frozen sections which was to be immunostained. M-cluster which differentiated on a cover glass coated with gelatin was also fixed by 4% (vol/vol) paraformaldehyde/0.01M PBS and used for immunostaining. Anti SSEA-3 antibody [1:50, Millipore], anti Nanog antibody [1:100, Millipore], anti Oct3/4 antibody [1:100, Santa Cruz], anti Sox2 antibody [1:1000, Millipore], anti PAR4 antibody (1:100, Santa Cruz), anti smooth muscle actin (SMA) antibody [1:100, Lab Vision, anti Neurofilament-M antibody [1:100, Millipore] and anti Cytokeratin 7 antibody (CK7) (1:100, Milllipore] were used and these primary antibodies were detected using FITC-, Alexa-488 or Alexa-568 labeled anti-rabbit IgG, anti mouse IgG or anti-mouse IgN [1:500, Molecular Probes].

6. RT-PCR

Total RNA was extracted from M-cluster differentiated in vitro by the method mentioned in 4. above using Nucleo Spin RNA Xs (Macherey-Nagel). cDNAs were obtained by reverse transcription using Super Script VILO cDNA Synthesis Kit (Invitrogen) to obtain cDNA from the total RNA. For PCR, Ex tag DNA polymerase (Takara Bio, Inc.) was used to examine the expression of α-fetoprotein (AFP, a marker for endoderm), GATA6 (a marker for endoderm), micro tubule-associated protein-2 (MAP-2) (a marker for ectoderm) and Nkx2.5 (a marker for mesoderm). FIG. 62 shows the sequence of the used primers. Human whole embryo, human fetus liver, human adult brain and human adult liver were used for control.

7. Transplantation of Cells to Testis of Immunodeficient Mice

SSEA-3 positive cells prepared using FACS as mentioned in 2. above were stained with trypan blue and living cells were counted. After counted, cells were suspended to $1.5 \times 10^5$ cells/pt and $1.5 \times 10^5$ cells were transplanted to one testis of 8-weeks old male CB17/Icr-Prkdc scid/CrlCrlj (SCID) mice. Mouse ES cells were transplanted as positive control and PBS was administered for negative control. Mice in SSEA-3 positive group were refluxed and fixed 4 months and 6 months after the transplantation and mice in mouse ES cell transplantation group and PBS administration group were refluxed and fixed 2 months after the transplantation.

8. Study for the Self-Renewal Ability

Figure 60:
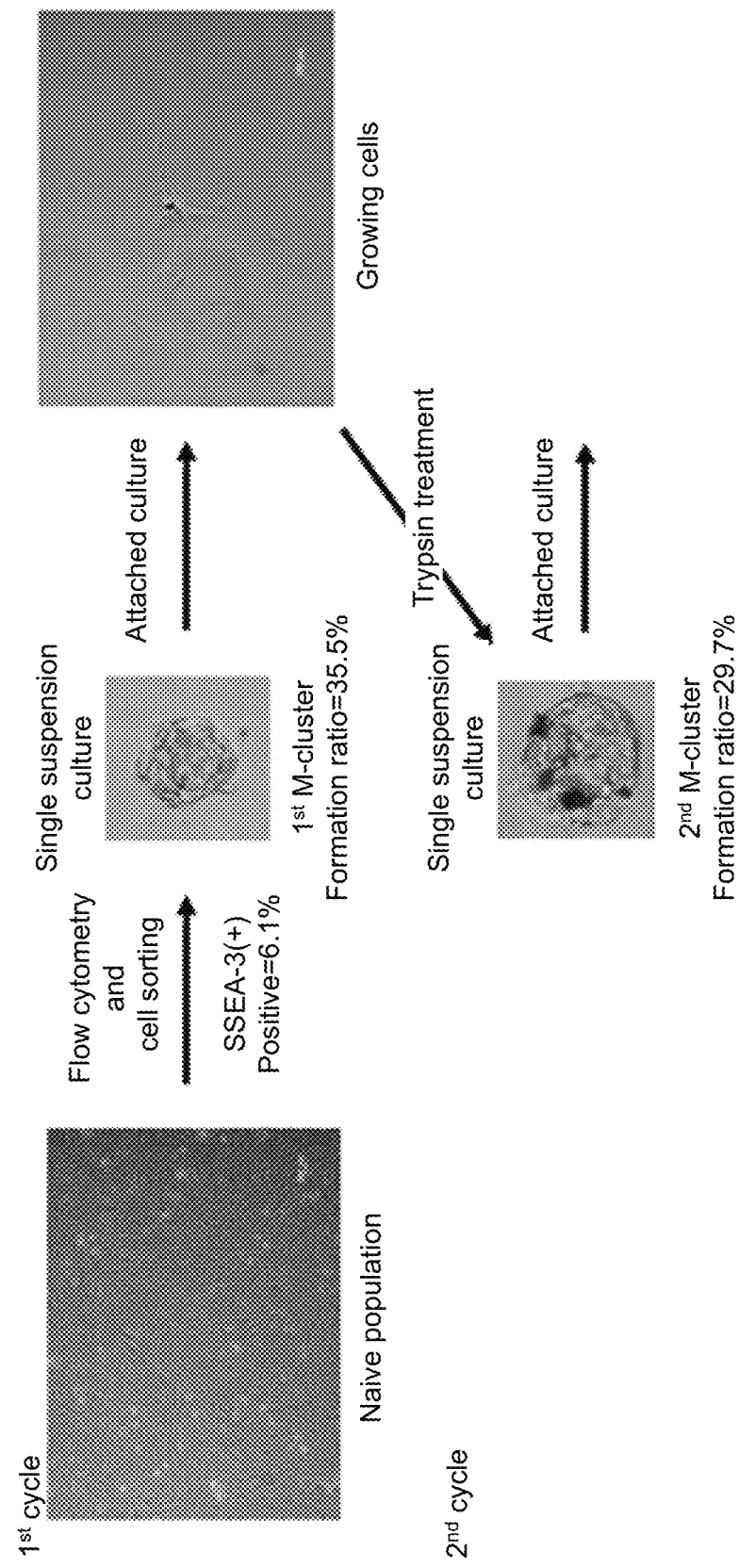
FIG. 60 is a diagram which shows human adipose-derived stem cell (HADSC)-derived Muse cell has self-renewal ability.

First generation of M-cluster which was obtained by the single cell suspension culture of SSEA-3 positive cells prepared using FACS as mentioned in 2. above was subjected to attached culture in a dish coated with 0.1% gelatin and containing 300 μl of a MEM [15% (vol/vol) FBS] to grow cells. Growing cells were detached by adding trypsin-EDTA and cells were subjected to the single suspension culture again to form 2nd generation of M-cluster. FIG. 60 shows the summary of the method.

Results

Figure 51A:
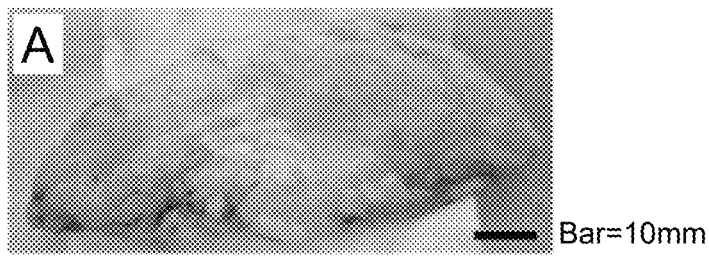
FIGS. 51A and 51B show the morphology of human subcutaneous adipose tissue (A) and the established mesenchymal cell derived from human subcutaneous adipose tissue (B).
Figure 51B:
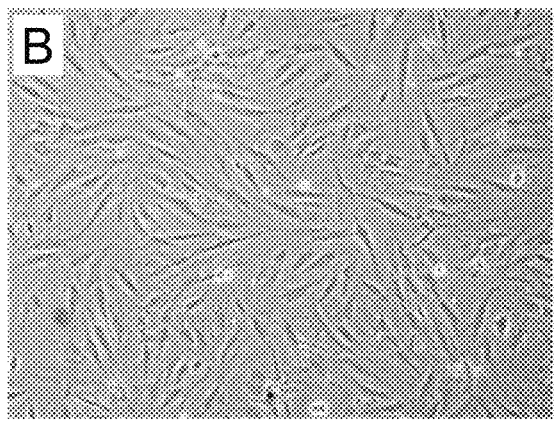

In the present example, 2 sources, one is cell which is commercially available as human adipose derived mesenchymal cell and the other was mesenchymal cell established by the present inventors from subcutaneous adipose tissue. Using the method of the present example, cells were collected from human subcutaneous adipose tissue the volume of which was 15.4 cm³ (FIG. 51A) and were cultured for 16 days. As human adipose tissue derived mesenchymal cells (FIG. 51B), $1.96 \times 10^7$ cells were established.

Figure 52A:
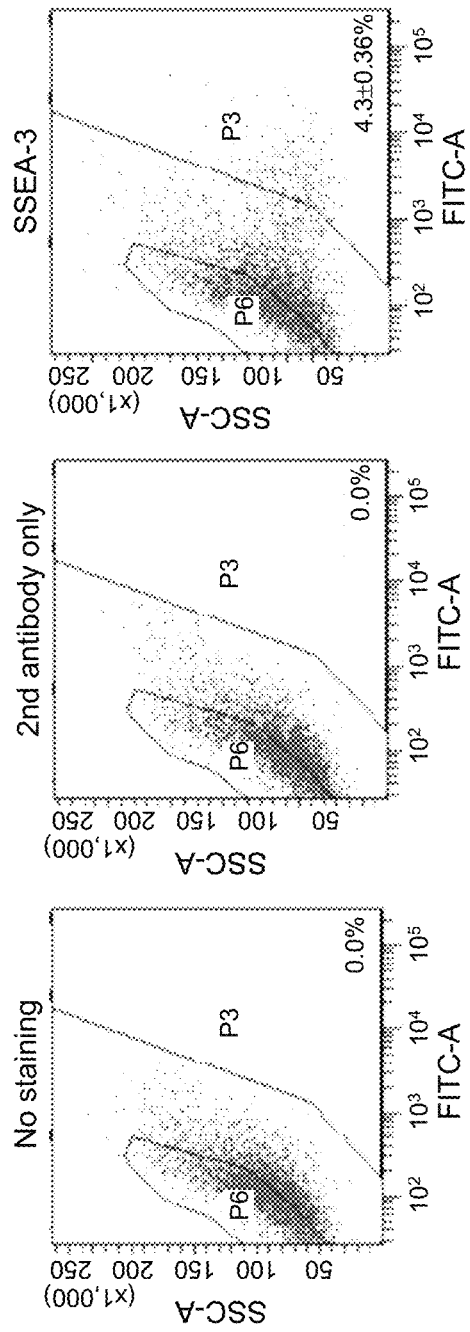
FIGS. 52A and 52B show the expression of SSEA-3 on commercially available human adipose-derived stem cell (HADSC) (A) and the established mesenchymal cell derived from human subcutaneous adipose tissue (B).
Figure 52B:
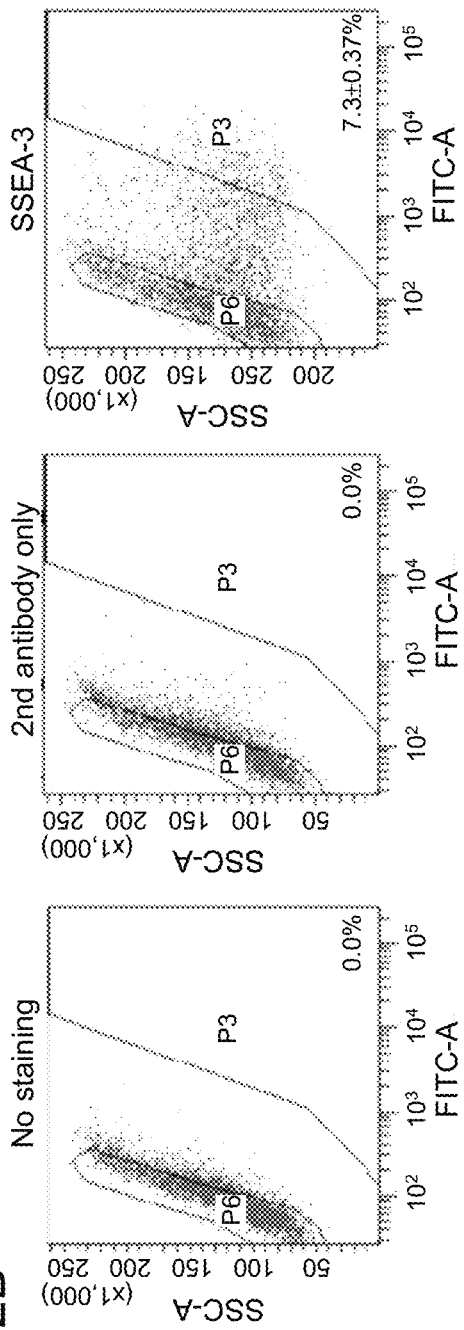

FACS analysis revealed that Muse cells which can be separated using SSEA-3 as a marker are present in each cell fraction source. For commercially available cells, 4.3±0.36% Muse cells are contained in the cell fraction and 7.3±0.37% Muse cells are contained in the cells established from the primary culture of the adipose tissue (FIGS. 52A and 52B). FIG. 52A shows the expression of SSEA-3 in commercially available human adipose-derived stem cell (HADSC) and FIG. 52B shows the expression of SSEA-3 in the established cell.

Figure 53A:
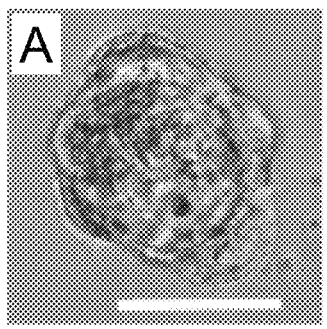
FIGS. 53A and 53B are photographs which show the morphology of Muse cell-derived embryoid body (EB)-like cell cluster (M-cluster).
Figure 53B:
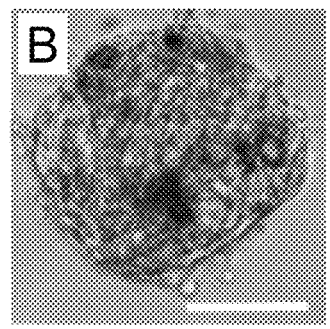

Muse cell forms M-cluster (Muse cell-derived embryoid body (EB)-like cell cluster) which is similar to embryoid body from a human ES cell from a single cell by suspension culture. Thus, Muse cell positive for SSEA-3 and non-Muse cell negative for SSEA-3 were collected and subjected to suspension culture. As a result, it was confirmed that M-cluster was formed from single Muse cell only. From SSEA-3 positive cell isolated from commercially available HADSC, 65 to 66% cells were formed M-cluster and 44.2% cells formed M-cluster from SSEA-3 positive cells isolated from established cell. FIGS. 53A and 53B show the morphology of M-cluster. FIG. 53A shows the morphology of M-cluster obtained from commercially available HADSC and FIG. 53B shows the morphology of established cell.

Figure 54:
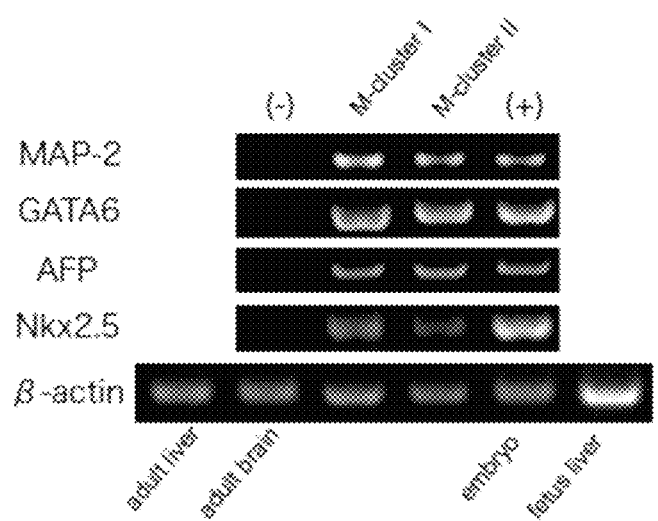
FIG. 54 is the results of RT-PCT which shows the differentiation of M-cluster. In the figure, "M-cluster I" indicates the differentiation of M-cluster obtained from commercially available human adipose-derived stem cell (HADSC) and "M-cluster II" indicates the differentiation of M-cluster obtained from the subcutaneous adipose tissue-derived mesenchymal cells.

Further, the expression of microtubule-associated protein-2 (MAP-2) (a marker for ectoderm), GATA6 (a marker for endoderm), α-fetoprotein (AFP, a marker for endoderm), and Nkx2.5 (a marker for mesoderm) was confirmed for in vitro culture of the formed M-cluster in a dish coated with gelatin by RT-PCR. The expression shows the spontaneous differentiation into cells of three germ layers (tridermic cells) (FIG. 54). In FIG. 54, M-cluster I shows the differentiation of M-cluster obtained from commercially available HADSC and M-cluster shows the differentiation of M-cluster obtained from the established cells.

Further, in immunostaining using antibodies against Neuro filament-M (NF, ectodermal nerve), Cytokeratin 7 (CK7, endodermal biliary tree) and Smooth muscle Actin (SMA, mesodermal smooth muscle), it was proved that M-cluster differentiated into cells of three germ layers. In FIGS. 55A-55C, the oval objects are nucleus stained by DAPI and elongated objects are cells which are stained with anti-NF antibody, anti-CK7 antibody and anti-SMA antibody.

Figure 56:
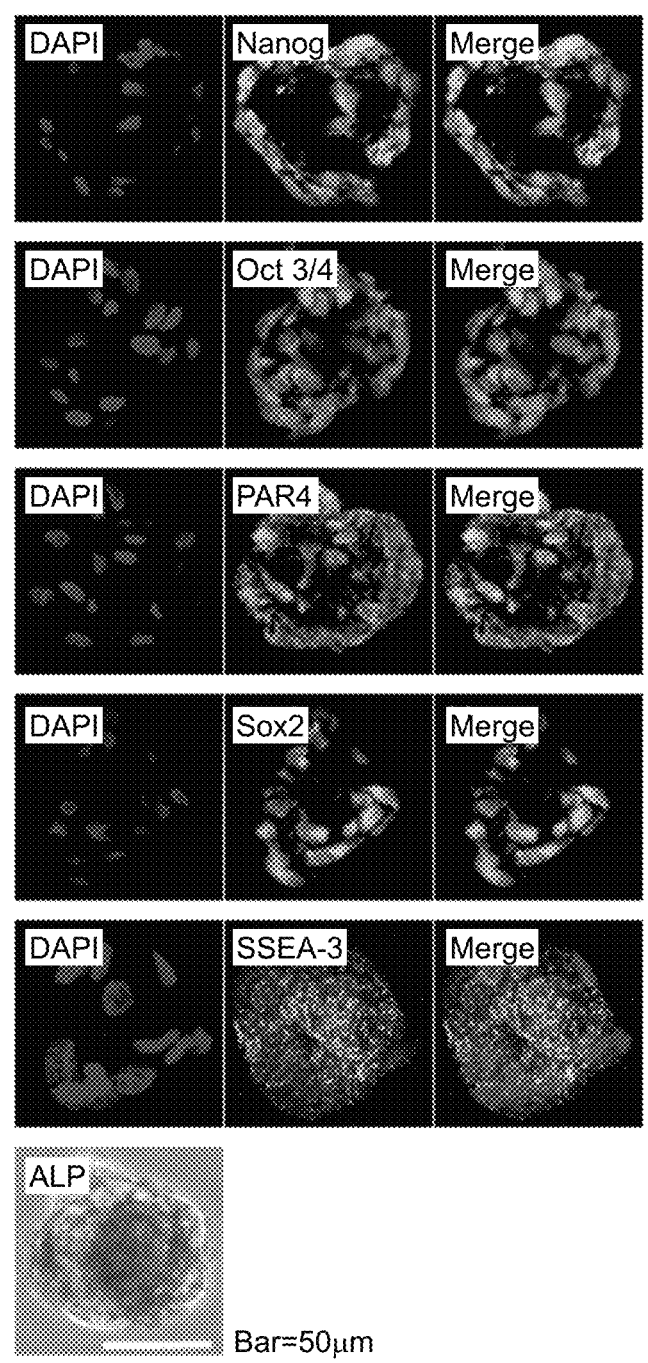
FIG. 56 is a photograph which shows the expression of pluripotent cell markers of M-cluster formed from human adipose-derived stem cell (HADSC).

It was further confirmed that M-cluster expressed pluripotent markers such as Nanog, Oct3/4, PAR4, Sox2, SSEA-3 and alkaline phosphatase (ALP). These results proved that Muse cell isolated from HADSC has pluripotency and ability to differentiate into cells of three germ layers (FIG. 56). In FIG. 56, left side panels show nucleus which stained blue, central panels shows immunostained images stained with antibodies against Nanog, Oct3/4, PAR4, Sox2 and SSEA-3 from on high, respectively. Right side panels are merged images of DAPI stained images and immunostained images. The lowermost panel shows images stained with anti ALP antibody, which indicates the expression of ALP.

Figure 57A:
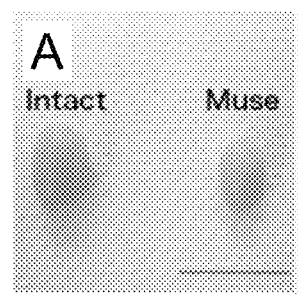
FIGS. 57A and 57B are photographs which show that Muse cell is non-tumorigenic (4 months after transplantation) In contrast, mouse ES cell formed teratoma by 8 weeks.
Figure 57B:
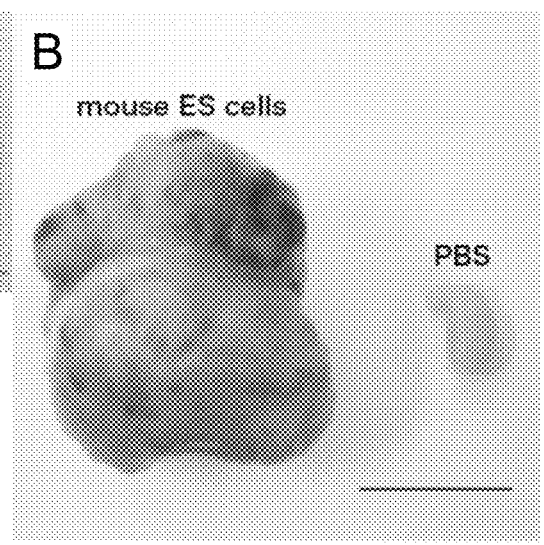
Figure 58A:
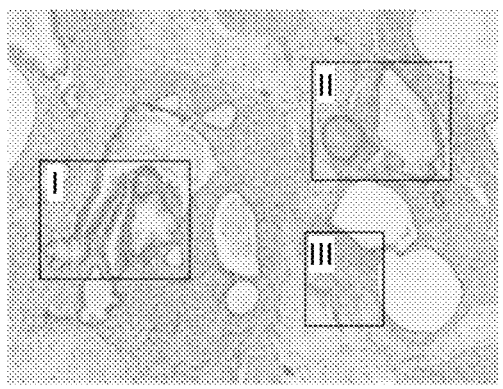
FIGS. 58A, 58B, 58C and 58D show photographs of HE staining of teratoma generated from Mouse ES cells. In the figure, I is intestinal epithelium (endoderm) (FIG. 58B), II is neuronal element (ectoderm)(FIG. 58C) and III is smooth muscle (mesoderm) (FIG. 58D).
Figure 58B:
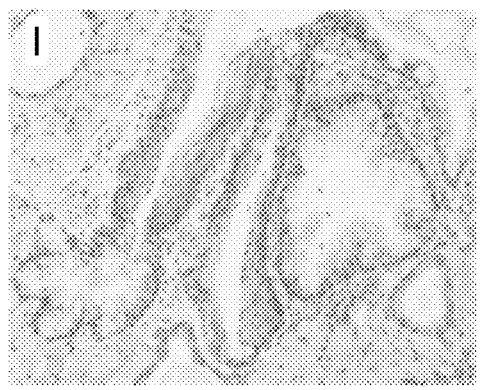
Figure 58C:
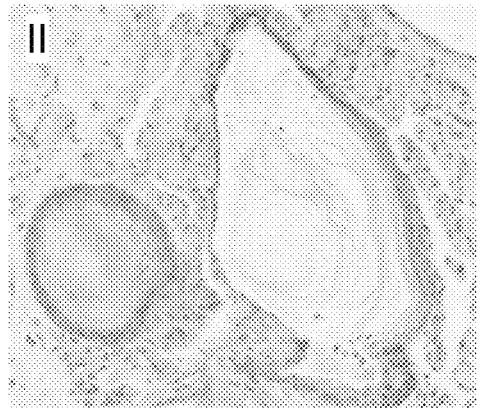
Figure 58D:
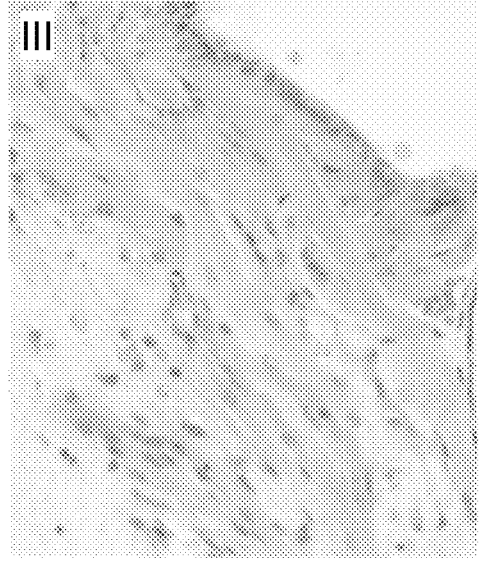

For the transplantation of cells into mouse testis, mouse ES cells formed teratoma in 8 weeks after the transplantation. While, Muse cells did not form teratoma for 4 months after the transplantation. This shows that Muse cells derived from commercially available HADSC and the established cells were not tumorigenic (FIGS. 57A and 57B). In FIGS. 57A and 57B, A shows the results of control (Intact) and the transplantation of Muse cells)(4 months), and B shows the results of the transplantation of mouse ES cells (8 weeks).

Further, it was confirmed by HE-stained image that mouse ES cells formed teratoma including tridermic cells (FIGS. 58A-58D). In FIGS. 58A-58D, I (FIG. 58B) shows intestinal epithelium (endoderm), II (FIG. 58C) shows neural elements (ectoderm) and III (FIG. 58D) shows smooth muscle (mesoderm). While, in testis to which Muse cells were transplanted, HE-stained image did not reveal the formation of tumor (FIGS. 59A and 59B).

Self-renewal ability was examined by the method mentioned in 8. above. The formation rate of the 1st generation M-cluster was 35.5% and the formation rate of the 2nd generation M-cluster was 29.7% (FIG. 60). These results show that the obtained Muse cells had self-renewal ability.

Example 4

Pluripotent Stem Cell Derived from Umbilical Cord

Figure 61B:
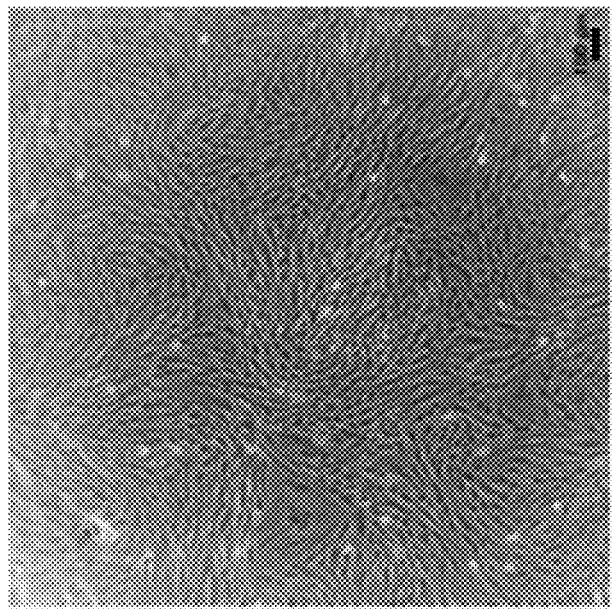
FIGS. 61A and 61B show the morphology of mesenchymal cells obtained from human umbilical cord.
Figure 61A:
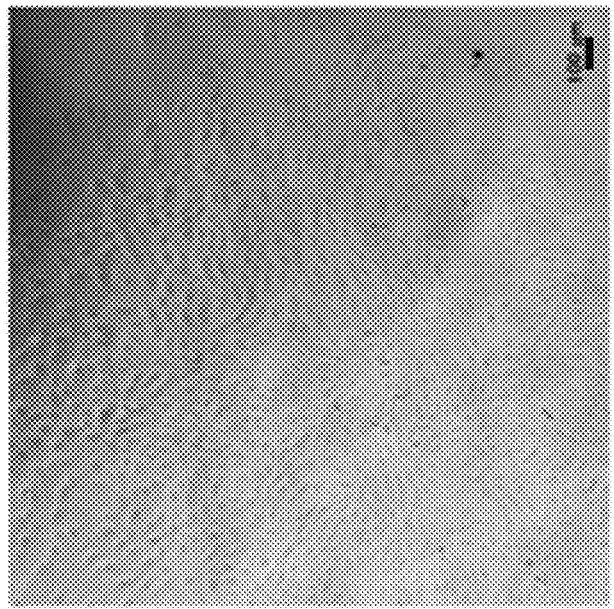
Figure 63:
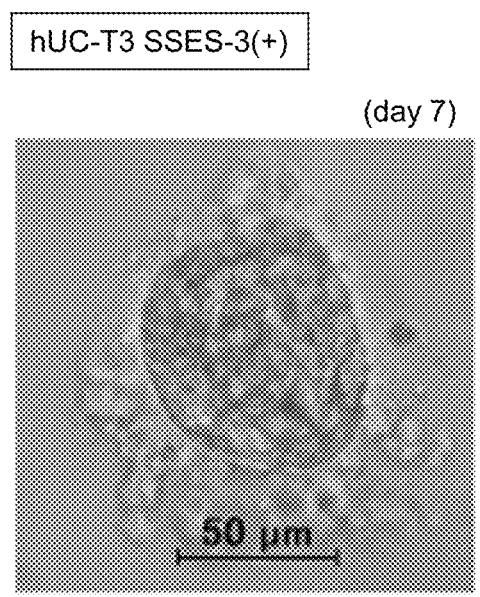
FIG. 63 the morphology of M-cluster formed from SSEA-3 (+) cell isolated from human umbilical cord.
Figure 64:
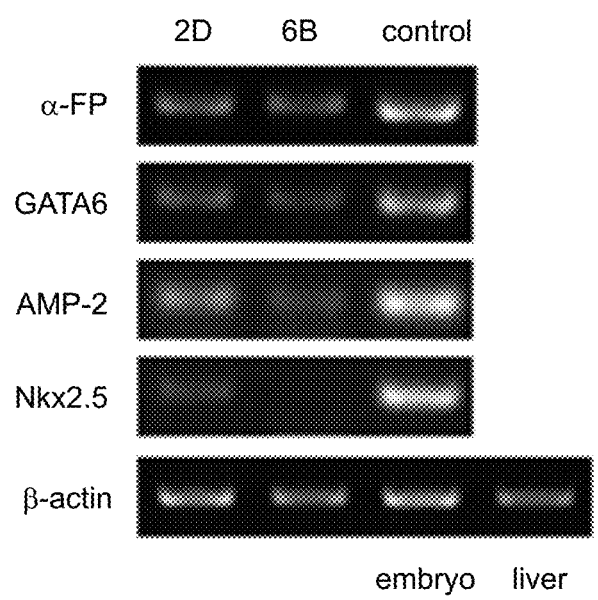
FIG. 64 shows the results of the RT-PCR analysis for alpha-fetoprotein (α-FP; endoderm), GATA6 (endoderm), MAP-2 (ectderm) and Nkx2.5 (mesoderm) of Muse cells isolated from umbilical cord.

Muse cells were isolated from human umbilical cord using SSEA-expression as a marker by the same method as mentioned in 1. to 3. of Example 3. Human umbilical cord was collected with the consent of a patient. Umbilical cord was disinfected and blood vessels and epidermis on the surface were removed and only inner mesenchymal tissue was collected. The collected tissue was cut into pieces. Mesenchymal cells were obtained by subjecting the cut tissue to attached culture. The obtained mesenchymal cells were subjected to FACS to collect Muse cells as SSEA-3 positive cells. The obtained cells were subjected to single cell suspension culture to form M-clusters and M-clusters were analyzed by RT-PCR and immunocytohistochemistry. FIGS. 61A and 61B show the morphology of mesenchymal cells obtained from human umbilical cord. FIG. 62 shows the expression of SSEA-3 on mesenchymal cells obtained from human umbilical cord. The mesenchaymal cells were obtained from human umbilical cord by the same method as mentioned in 2. of Example 3. FIG. 63 shows the morphology of M-cluster formed from SSEA-3(+) cell isolated from human umbilical cord. FIG. 64 shows the expression of alpha feto protein (AFP, a marker for endoderm), GATA6 (a marker for endoderm), micro tubule-associated protein-2 (MAP-2, a marker for ectoderm) and Nkx2.5 (a marker for mesoderm) in cells derived from a single SSEA-3(+) cell-derived cell cluster in gelatin culture.

Through examples 3 and 4, it was confirmed that Muse cells which are pluripotent cells are present in human adipose tissue derived mesenchymal cell and human umbilical cord-derived mesenchymal cell.

Muse cells express pluripotent markers and have ability to differentiate into tridermal cells from a single cell. Accordingly, human adipose tissue is prospective source of autologous cell transplantation therapy. Considering actual therapy, it is easier to collect adipose tissue from a recipient than to collect bone marrow or skin from the recipient. In the establish method of Muse cells of the present example, $1.9 \times 10^7$ cells were obtained as mesenchymal cells by 16-days culture of cells collected from human adipose tissue the volume of which was 15.4 cm$^3$. Provided that the positive rate for SSEA-3 is 5%, $9.8 \times 10^5$ cells among $1.9 \times 10^7$ cells from adipose tissue are estimated as Muse cells. Since sufficient number of cells can be prepared in short time from lower amount of tissue, it is extremely preferable for autologous transplantation therapy. Muse cells derived from human adipose tissue derived mesenchymal cells are cells from living body which is different from human ES cells and human iPS cells Thus, it is expected that Muse cells would solve the problems such as affection by gene introduction and risk for tumor formation which are confronted by other pluripotent cells.

The same thing can be said for Muse cells isolated from mesenchyamal cells derived from umbilical cord.

Example 5

Figure 65:
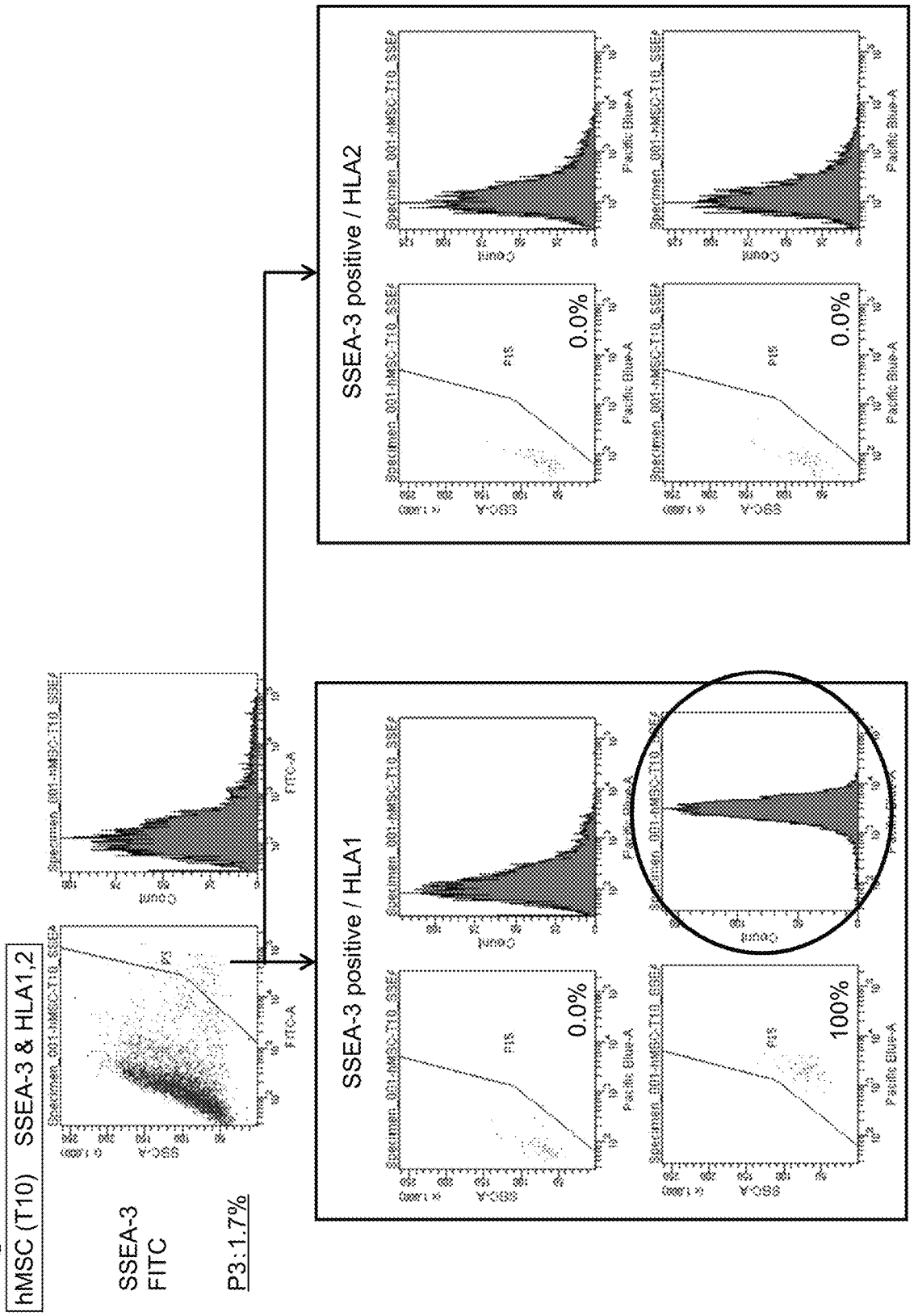
FIG. 65 shows the expression of HLA class I antigen but not HLA class II antigen of SSEA-3 positive cell which is derived from human bone marrow stroma cells.

Expression of HLA Class Antigens on SSEA Positive Cells Derived from Human Bone Marrow Stroma Cells and Human Dermal Fibroblasts; Analysis by Flowcytometry The expression of HLA class I antigen and HLA-class II antigen on SSEA-3 positive cells derived from human bone marrow stroma cells were confirmed by flowcytometry. FIG. 65 shows the results. As shown in FIG. 65, HLA 1 was positive for human bone marrow stroma cells, but HLA II was negative.

Figure 66:
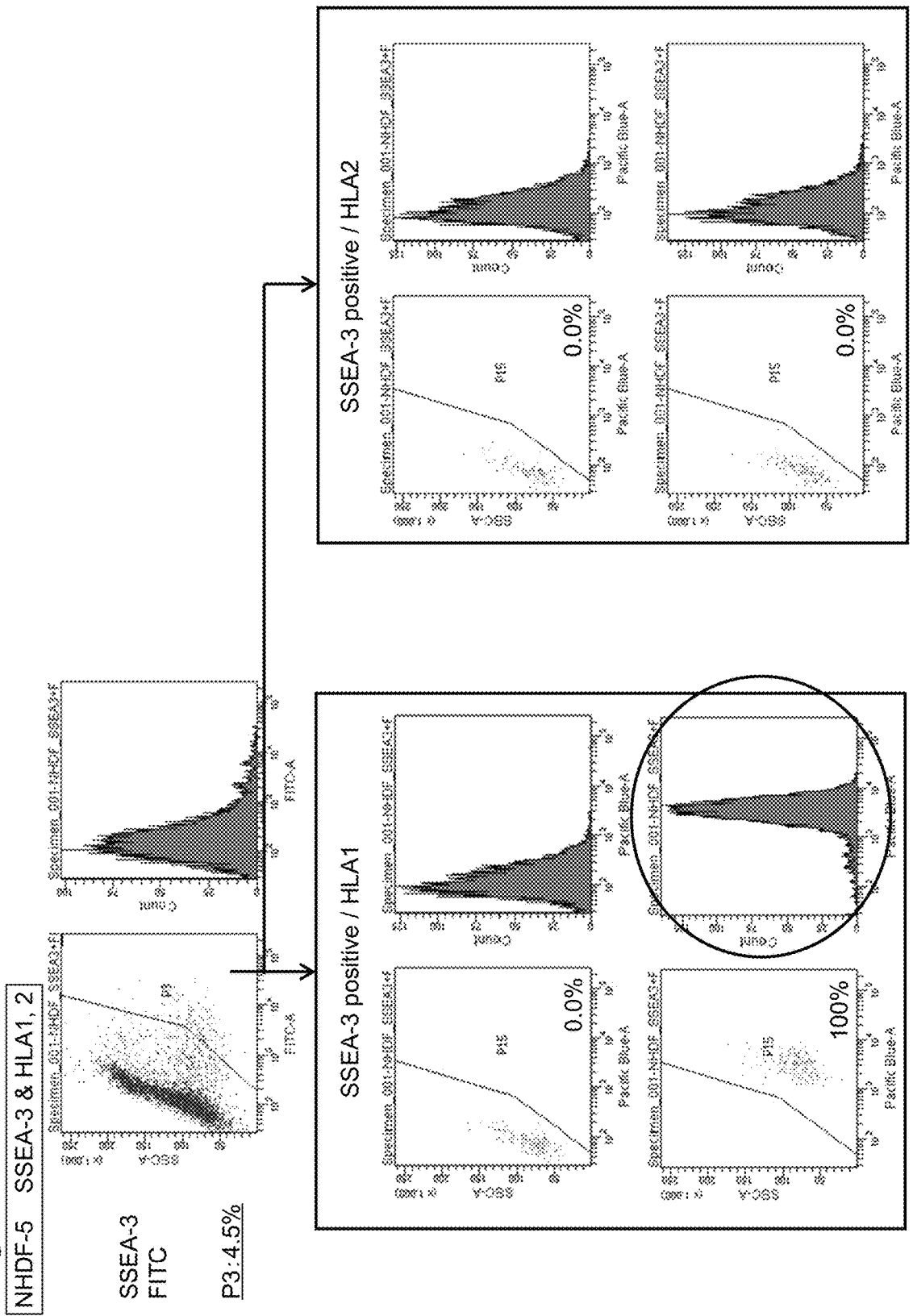
FIG. 66 shows the expression of HLA class I antigen but not HLA class II antigen of SSEA-3 positive cell which is derived from human dermal fibroblasts.

The expression of HLA class I antigen and HLA-class II antigen on SSEA-3 positive cells derived from dermal fibroblasts were also confirmed. FIG. 66 shows the results. As shown in FIG. 66, HLA 1 was positive for human dermal fibroblasts, but HLA II was negative.

Example 6

Expression of HLA Class Antigens on Muse Cells; Analysis by Immunocytochemistry

Figure 67:
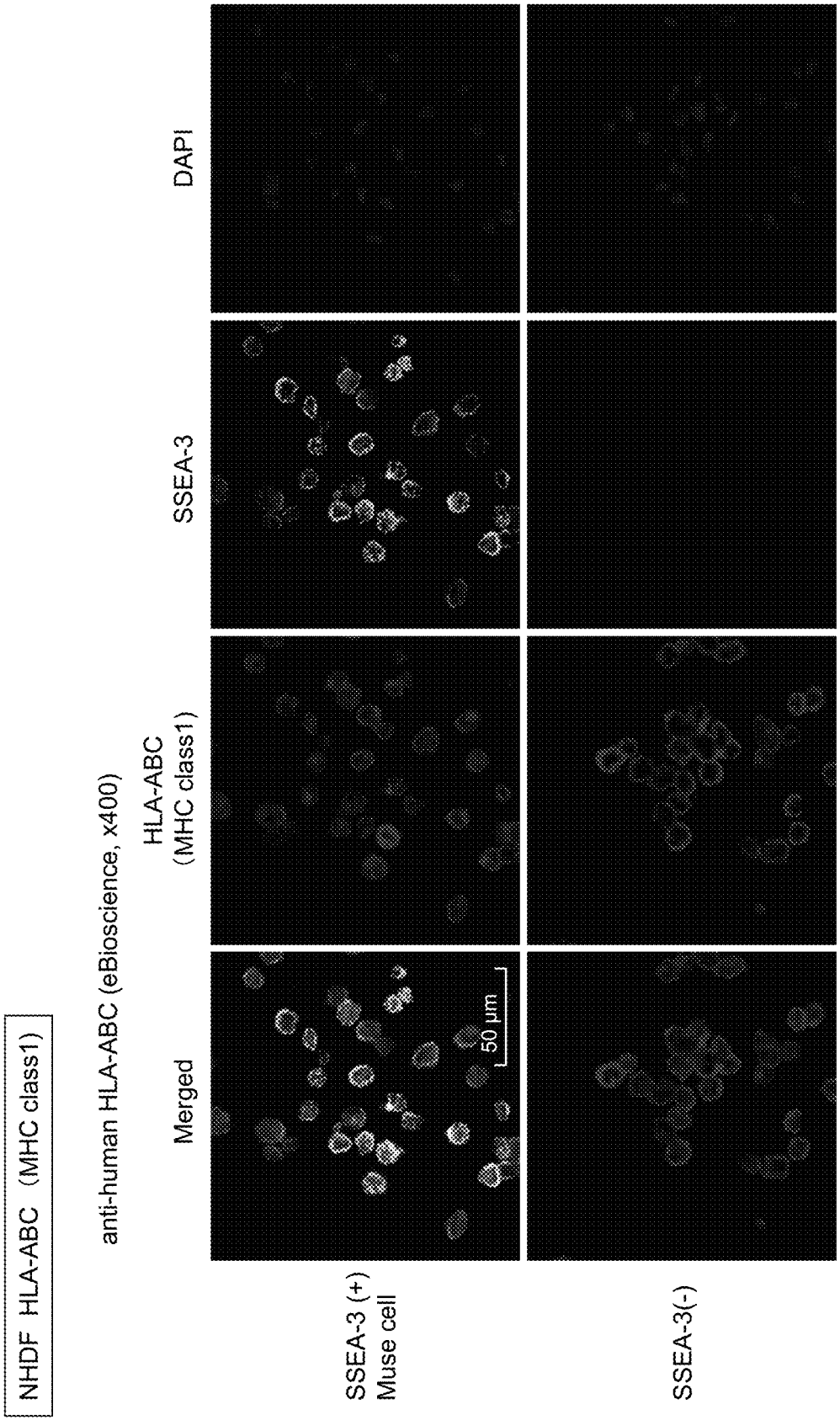
FIG. 67 shows the expression of HLA class I on Muse cells and non-Muse cells.

The expression of HLA class I antigen on Muse cells (SSEA-3 positive) and non Muse cells (SSEA-3 negative)

was examined by immunocytochemistry staining using anti-human HLA-ABC antibodies (eBioscience). Anti-mouse IgG antibody was used as a second antibody (labelled with Alexa568). FIG. 67 shows the results. As shown in FIG. 67, the expression of HLA class I antigens was observed on both of Muse cells (SSEA-3(+) cells) and non-Muse cells (SSEA-3(−) cells).

Figure 68:
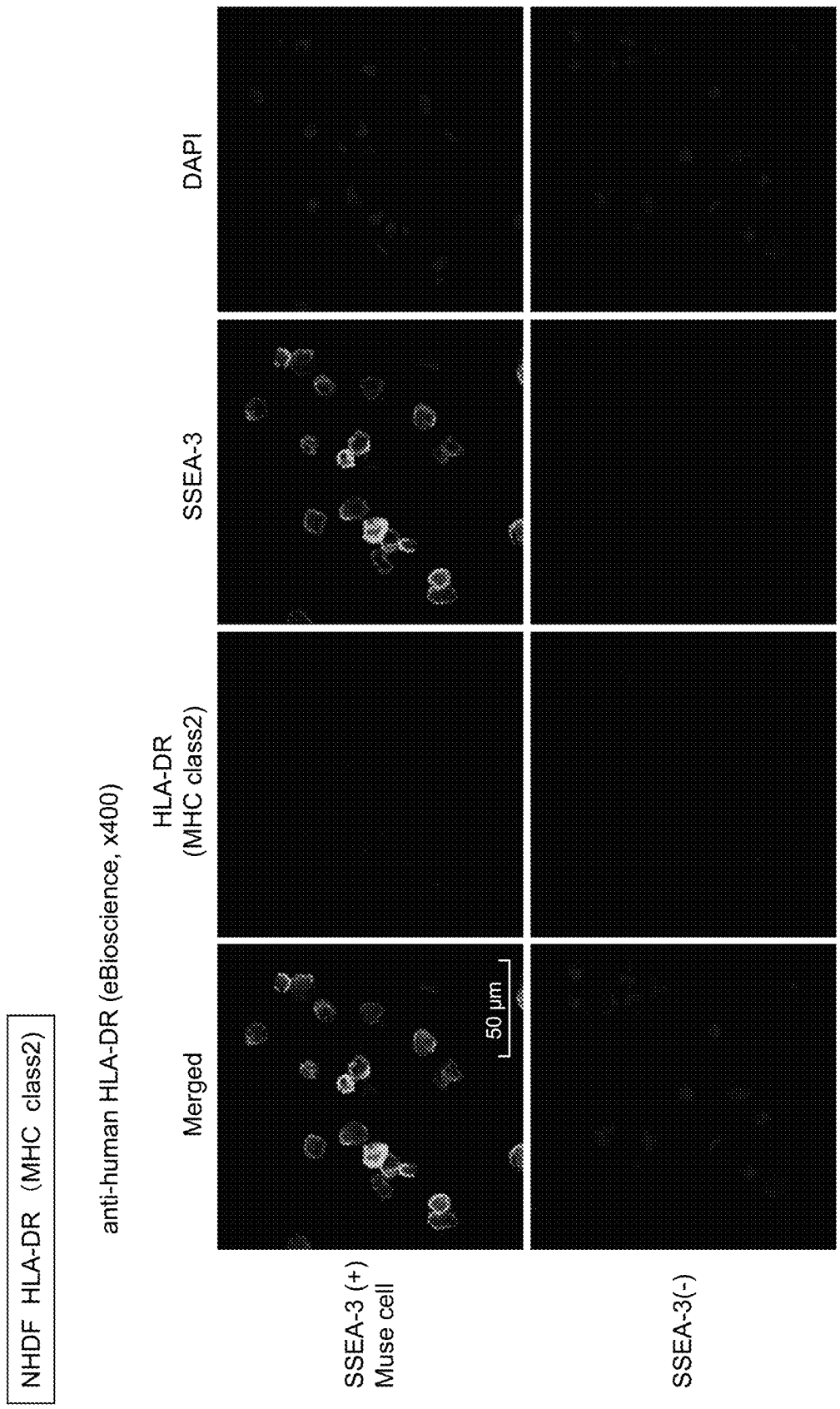
FIG. 68 shows no expression of HLA class II on Muse cells nor non-Muse cells.

The expression of HLA class II antigen on Muse cells (SSEA-3 positive) and non-Muse cells (SSEA-3 negative) was examined by immunocytochemistry staining using anti-human HLA-DR antibody (eBioscience). Anti-mouse IgG antibody was used as a second antibody (labelled with Alexa568). FIG. 68 shows the results. As shown in FIG. 67, the expression of HLA class II antigens was not observed on both of Muse cells and non-Muse cells.

Figure 69:
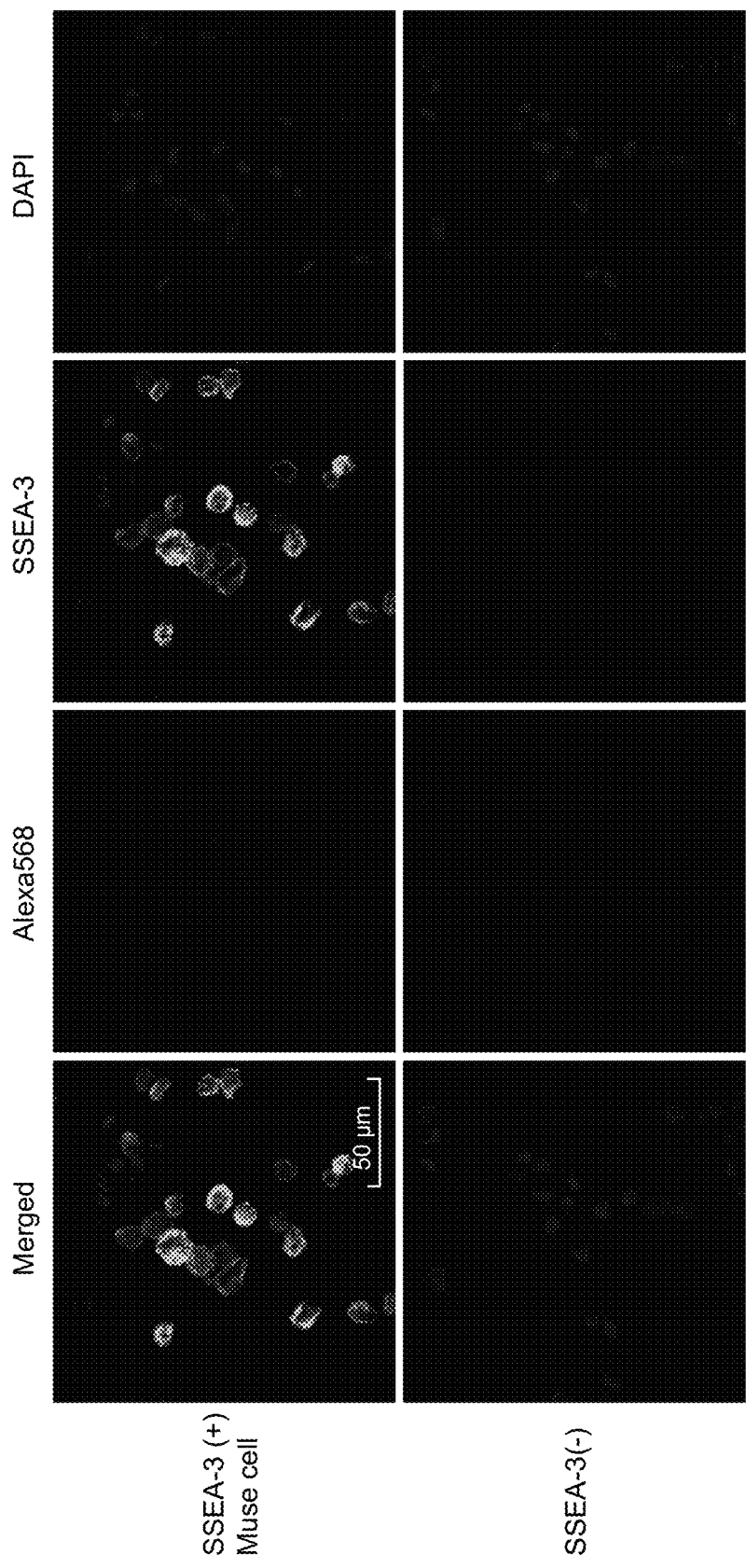
FIG. 69 shows no non-specific reaction of Muse cells and non-Muse cells to secondary antibody conjugated with Alexa568.

FIG. 69 shows the non-specific reaction in the above experiment. As shown in FIG. 69, the light emission by Alexa 568 was not observed. This result shows that there was no non-specific reaction of Alexa568.

Example 7

Study for Immune Suppression Effect of Muse Cells by Lymphocyte Stimulation Test The present inventors confirmed whether or not Muse cells had immune suppression effect by the tests for the induction of dendritic cells. More specifically, monocytes were isolated from human peripheral blood and co-cultured with Muse cells. Through this study, the inventors confirmed whether or not dendritic cells were induced from monocytes.

Muse cells and non-Muse cells were isolated from human fibroblasts using SSEA-3 Human monocytes were also used.

Regarding culture medium, a MEM (10% FBS, 2 mM L-glutamine, Kanamycin) was used for Muse cells and non-Muse cells isolated from human fibroblasts, RPMI-1640 (10% FBS) was used for induction of human monocytes into monocyte-derived dendritic cell (MoDC) progenitor cell and RPMI-1640 (10% FBS, 2 mM L-glutamine, 2 mM sodium pyruvate, 40 ng/mL GM-CSF, 20 ng/mL IL-4, Kanamycin) was used for induction of MoDC progenitor cell to dendritic cells.

Specific methods are as follows.

(1) Collection of Monocytes

Peripheral blood of healthy subject was collected and monocytes fraction only was isolated using Lymphoprep Tubes (Axis-Shield PoC AS). Then, the monocytes fraction was suspended in RPMI medium (10% FBS) and seeded in 10 cm dish. Next day, the dish was washed two times to remove unattached cells.

Figure 70:
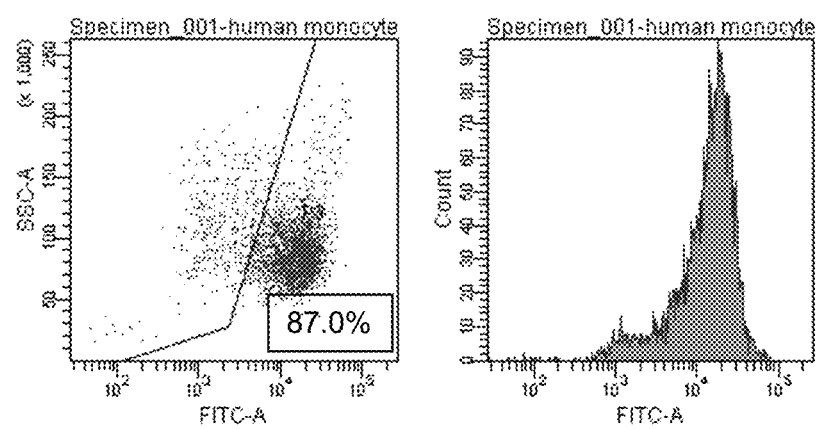
FIG. 70 shows the results of FACS analysis (CD14) of cells obtained from human peripheral blood for lymphocyte stimulation test.

Attached cells were detached from the dish using 0.25% trypsin/2 mM EDTA and stained with anti-human CD14 (a marker for human monocyte) to be analyzed by FACS. FIG. 70 shows the results. It was confirmed that more than about 90% cells were CD14 positive.

(2) Induction of Differentiation from Monocyte to MoDC Progenitor Cells

When monocytes are cultured in the presence of GM-CSF and IL-4 for several days, the cells differentiate into MoDC progenitor cells and then becomes mature dendritic cells by TNF-α.

Figure 71C:
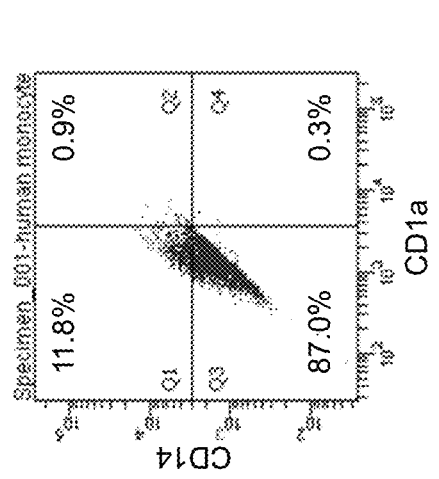
Figure 71D:
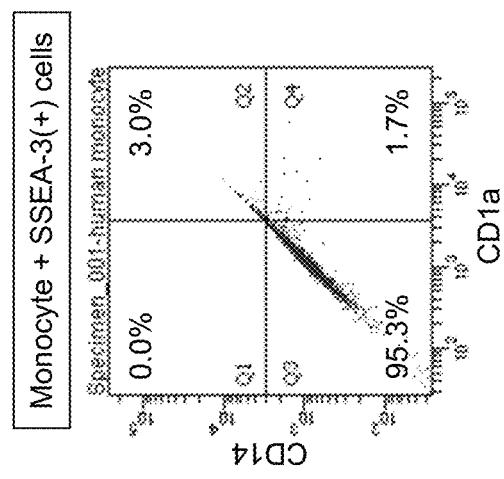
Figure 71E:
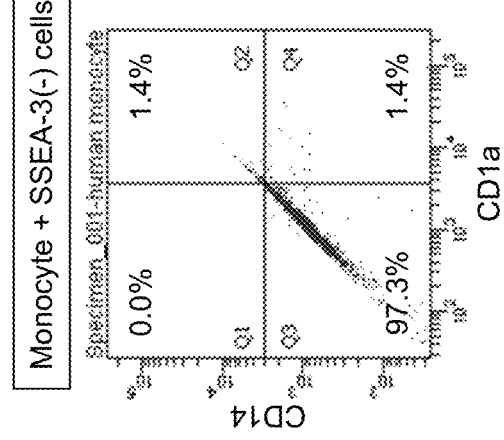
Figure 72:
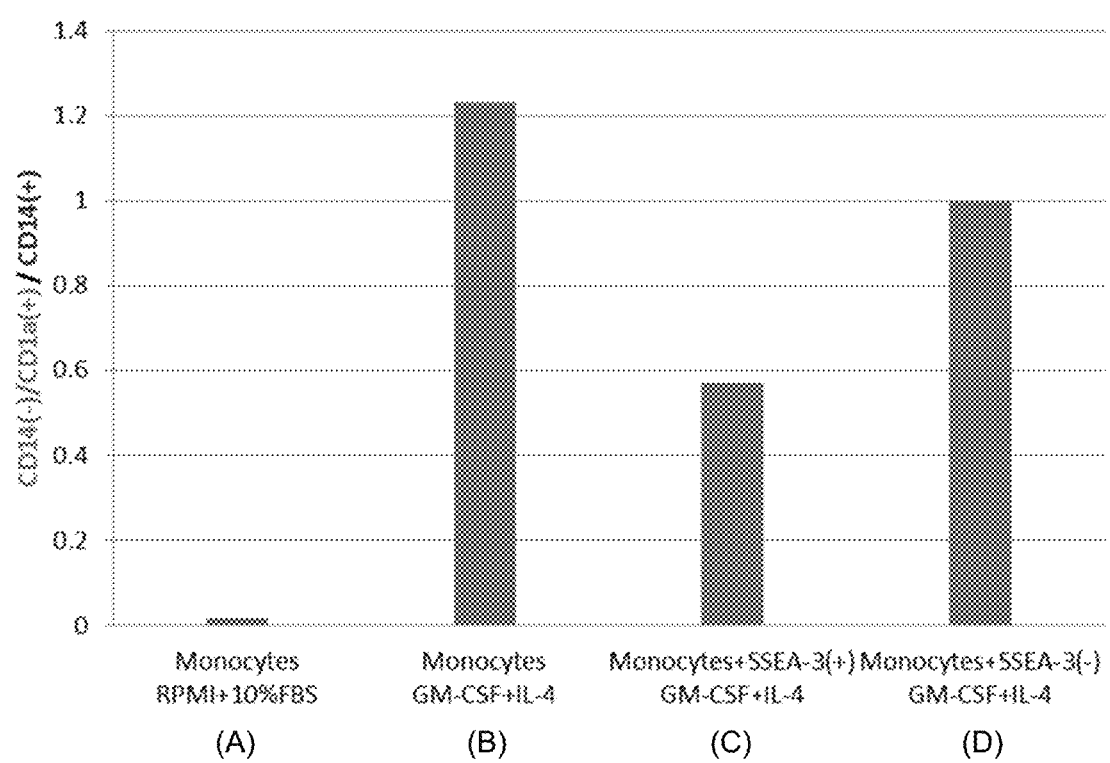
FIG. 72 shows the suppression of induction of differentiation from monocytes to monocyte-derived dendritic cell (MoDC) progenitor cells in the presence of Muse cells.

In the presence of Muse cells, in the presence of non-Muse cells, monocytes isolated as mentioned in (1) above were cultured. The medium used for the induction of the monocyte-derived dendritic cell (MoDC) progenitor cells by culturing monocytes was RPMI-1640 (10% FBS, 2 mM L-glutamine, 2 mM sodium pyruvate, 40 ng/mL GM-CSF, 20 ng/mL IL-4, Kanamycin). In the culture, conditions were changed for the absence or presence of cytokines and the absence or presence of co-culture with Muse cells or non-Muse cells. The specific conditions were (A) only monocytes (without cytokines) (Negative control), (B) only monocytes (with cytokines) (Positive control), (C) monocytes+Muse cells (SSEA-3(+) cells), and (D) monocytes+non Muse cells (SSEA-3(−) cells). The expression "monocytes+Muse cells" means co-culture of monocytes with Muse cells. Five days later, cells were detached using 0.25% trypsin/2 mM EDTA and stained with anti-CD1a (a marker for human MoDC progenitor cells) antibody and anti-CD14 antibody (a marker for human monocyte) to be analyzed by FACS. FIGS. 71A-71E show the results. FIGS. 71 A, B, C and D show the results of FACS analysis for conditions (A), (B), (C) and (D), respectively. In FIGS. 71A-71E, Q1 shows the presence of monocytes, Q2 shows the presence of halfway-differentiated cells, Q3 shows other cells, and Q4 shows MoDC progenitor cells (See FIG. 71 E). FIG. 72 shows the ratio of CD14 positive cells (monocytes) to CD1a positive cells (MoDC progenitor cells) after culture for each condition. As FIG. 72 shows, in case where monocytes were cultured in the absence of cytokines (condition (A)), MoDC progenitor cells were little. However, in case where monocytes were cultured in the presence of cytokines (condition (B)), MoDC progenitor cells were observed. When monocytes were co-cultured with non-Muse cells, the number of MoDC progenitor cells was smaller than condition (B). While, monocytes were co-cultured with Muse cells, induction of MoDC progenitor cells was significantly suppressed compared to condition (B). These results show that Muse cells suppressed induction of differentiation of MoDC progenitor cells from monocytes. Both of Muse cells and non-Muse cells suppressed induction of differentiation of MoDC progenitor cells. However, the induction by Muse cells was stronger.

(3) Induction of Differentiation from MoDC Progenitor Cells to Dendritic Cell

Figure 74:
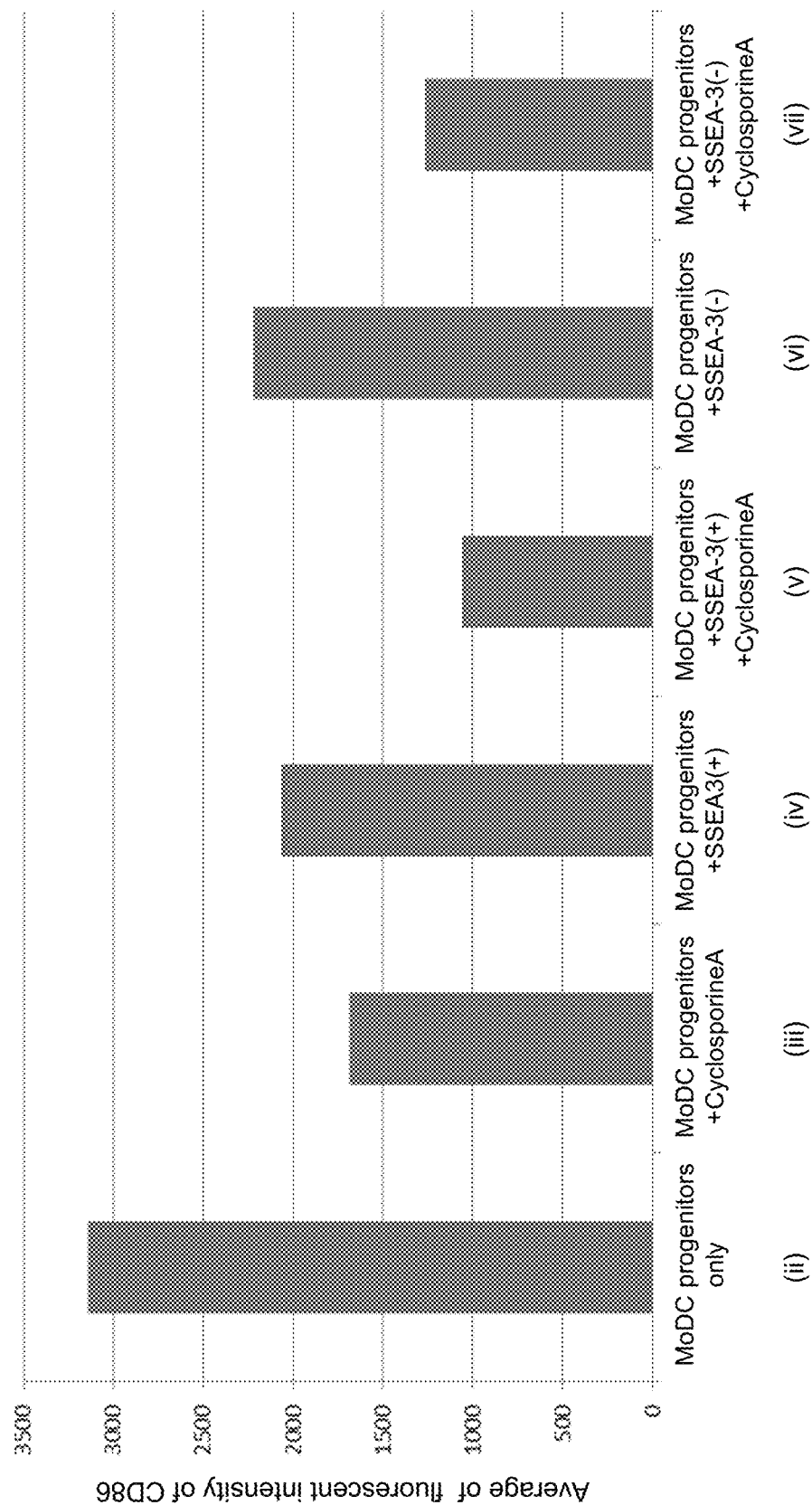
FIG. 74 shows the suppression of induction of differentiation from monocyte-derived dendritic cell (MoDC) progenitor cells to dendritic cells in the presence of Muse cells.

The monocyte-derived dendritic cell (MoDC) progenitor cells were induced by the culture of monocytes using RPMI-1640 (10% FBS, 2 mM L-glutamine, 2 mM sodium pyruvate, 40 ng/mL GM-CSF, 20 ng/mL IL-4, Kanamycin) of (2) above. Five days after monocyte culture started, 10 ng.mL human TNF-α was added to the culture medium. In the culture, conditions were changed for the absence or presence of cytokines and the absence or presence of co-culture with Muse cells or non-Muse cells. One µg/mL cyclosporine A instead of TNF-α was added to the culture medium as a control since cycloporine A inhibits the maturation of dendritic cells. Further, seven days after monocyte culture started (2 days after the TNF-α treatment), cells were stained with anti-human CD86, which expresses strongly on dendritic cell to be analyzed with FACS. FIGS. 73A-73G show the results. FIGS. 73A-73G ((i) to (vii)) shows the results under conditions (i) only MoDC progenitors (without cytokines), (ii) only MoDC progenitors (with cytokines), (iii) only MoDC progenitors (with cytokines+Cyclosporine A), (iv) MoDC progenitors+Muse cells (SSEA-3(+) cells), (v) MoDC progenitors+Muse cells (SSEA-3(+) cells+Cyclosporine A, (vi) MoDC progenitors+non-Muse cells (SSEA-3(−) cells) and (vii) MoDC progenitors+non-Muse cells (SSEA-3(−) cells+Cyclosprorine A), respectively. As the figure shows, the expression of CD86 reduces when Muse cells were co-cultured with MoDC progenitor cells. FIG. 74 shows the expression of CD86 after the culture for each condition (ii) to (vii). Each condition is (ii) MoDC progenitors only, (iii) MoDC progenitors+Cyclosporine A, (iv) MoDC progenitors+Muse cells (SSEA-3(+) cells), (v) MoDC progenitors+Muse cells (SSEA-3(+) cells)+Cyclosporine A, (vi) MoDC progenitors+non-Muse cells (SSEA-3(−) cells) and (vii) MoDC progenitors+non-Muse cells (SSEA-3(−) cells)+Cyclosporine A). As the figure shows, the expression of CD86 reduces when Muse cells were co-cultured with MoDC progenitor cells. These results show that Muse cells suppressed induction of differentiation of monocytes to monocyte-derived dendritic cell (MoDC) progenitor cells and MoDC progenitor cells to dendritic cells. Both of Muse cells and non-Muse cells suppressed induction of differentiation of monocytes and MoDC progenitor cells, the extent of suppression was stronger for Muse cells.

INDUSTRIAL APPLICABILITY

According to the present invention, pluripotent stem cells can be obtained from body tissue without using any germ cells or early embryos and without using an artificial induction operation such as foreign gene transfer or introduction of a specific compound. The pluripotent stem cells of the present invention can be efficiently prepared without using an artificial operation such as foreign gene transfer, so that they can be safely used when applied for treatment. Also, the pluripotent stem cells of the present invention can be used for regeneration medicine and treatment for dysfunctional tissue or the like, and they can be further used for research into cell division or tissue regeneration, for example.

All publications, patents, and patent applications cited in this specification are herein incorporated by reference in their entirety.

What is claimed is:

1. A method for preparing a cell fraction comprising 50% or more of multilineage-differentiating stress enduring cells (MUSE cells), comprising:
   exposing mesenchymal cells derived from bone marrow, adipose tissue, skin, umbilical cord or blood to cellular stress conditions selected from the group consisting of low-oxygen culture conditions, serum starvation culture conditions, and sugar starvation culture conditions;
   collecting survival cells;
   separating the collected cells using SSEA-3 antigen marker as an index; and
   recovering a cell fraction comprising 50% or more of MUSE cells,
   wherein the MUSE cells in the recovered fraction are characterized by:
   (i) SSEA-3(+) and CD105(+);
   (ii) no telomerase activity or low telomerase activity as low as that of human fibroblasts;
   (iii) the ability to differentiate into the three germ layers;
   (iv) exhibit a lack of tumorigenesis;
   (v) self-renewal capability; and
   (vi) CD117(−) and CD146(−).

2. The method of claim 1 wherein the cellular stress is low-oxygen culture conditions.

3. The method of claim 2 wherein the low-oxygen culture conditions comprise 1% oxygen.

4. The method of claim 3 wherein the mesenchymal cells exposed to stress conditions are derived from bone marrow.

5. The method of claim 3 wherein the mesenchymal cells exposed to stress conditions are derived from adipose tissue.

6. The method of claim 3 wherein the recovered cell fraction comprises 70% or more of MUSE cells.

7. The method of claim 3 wherein the recovered cell fraction comprises 90% or more of MUSE cells.

8. The method of claim 3 wherein the recovered cell fraction comprises 95% or more of MUSE cells.

* * * * *